United States Patent
Yasarla et al.

(10) Patent No.: US 9,751,781 B2
(45) Date of Patent: Sep. 5, 2017

(54) METHOD TO SEPARATE LIGNIN-RICH SOLID PHASE FROM ACIDIC BIOMASS SUSPENSION AT AN ACIDIC PH

(71) Applicant: The Research Foundation for The State University of New York, Binghamton, NY (US)

(72) Inventors: Lakshmi Rakesh Kumar Yasarla, Vijayawada (IN); Bandaru V. Ramarao, Fayetteveille, NY (US); Thomas Amidon, Jamesville, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 169 days.

(21) Appl. No.: 14/387,169

(22) PCT Filed: Mar. 15, 2013

(86) PCT No.: PCT/US2013/032238
§ 371 (c)(1),
(2) Date: Sep. 22, 2014

(87) PCT Pub. No.: WO2013/142352
PCT Pub. Date: Sep. 26, 2013

(65) Prior Publication Data
US 2015/0044733 A1 Feb. 12, 2015

Related U.S. Application Data

(60) Provisional application No. 61/613,196, filed on Mar. 20, 2012.

(51) Int. Cl.
| | | |
|---|---|---|
| *B01D 21/01* | (2006.01) | |
| *B01D 21/26* | (2006.01) | |
| *B09C 1/02* | (2006.01) | |
| *C02F 1/52* | (2006.01) | |
| *C07G 1/00* | (2011.01) | |
| *C08H 7/00* | (2011.01) | |
| *C08H 8/00* | (2010.01) | |
| *C12P 7/10* | (2006.01) | |
| *C12M 1/00* | (2006.01) | |
| *C13K 13/00* | (2006.01) | |
| *B01D 21/00* | (2006.01) | |
| *B01D 36/04* | (2006.01) | |
| *C02F 1/00* | (2006.01) | |
| *C02F 103/26* | (2006.01) | |

(52) U.S. Cl.
CPC ........ *C02F 1/5272* (2013.01); *B01D 21/0012* (2013.01); *B01D 21/01* (2013.01); *B01D 21/262* (2013.01); *B01D 36/045* (2013.01); *C07G 1/00* (2013.01); *C08H 6/00* (2013.01); *C08H 8/00* (2013.01); *C12M 45/04* (2013.01); *C12M 45/09* (2013.01); *C12P 7/10* (2013.01); *C13K 13/00* (2013.01); *C13K 13/002* (2013.01); *C02F 2001/007* (2013.01); *C02F 2103/26* (2013.01); *C12P 2203/00* (2013.01); *Y02E 50/16* (2013.01)

(58) Field of Classification Search
CPC .......... B01D 21/01; B01D 21/262; B09C 1/02
USPC .......... 134/13; 210/201, 202, 225, 725, 738; 435/105
IPC ........................ B01D 21/01,21/26; B09C 1/02
See application file for complete search history.

(56) References Cited

U.S. PATENT DOCUMENTS

| | | |
|---|---|---|
| 5,130,395 A | 7/1992 | Nguyen et al. |
| 5,312,484 A | 5/1994 | Kaliski |
| 5,328,880 A | 7/1994 | Lampert et al. |
| 5,344,619 A | 9/1994 | Larwick et al. |
| 5,352,444 A | 10/1994 | Cox et al. |
| 5,565,509 A | 10/1996 | Nguyen et al. |
| 5,584,394 A | 12/1996 | Behl et al. |
| 5,587,157 A | 12/1996 | Cox et al. |
| 5,589,164 A | 12/1996 | Cox et al. |
| 5,603,411 A | 2/1997 | Williams et al. |
| 5,614,602 A | 3/1997 | Connors et al. |
| 5,667,885 A | 9/1997 | Nguyen et al. |
| 5,688,315 A | 11/1997 | Behl et al. |
| 5,696,194 A | 12/1997 | Connors et al. |
| 5,707,533 A | 1/1998 | Connors et al. |
| 5,733,758 A | 3/1998 | Nguyen |
| 5,736,032 A | 4/1998 | Cox et al. |
| 5,888,806 A | 3/1999 | Nguyen |
| 6,020,422 A | 2/2000 | Connors et al. |
| 6,071,379 A | 6/2000 | Wong Shing et al. |

(Continued)

OTHER PUBLICATIONS

Shi, H. et al., Bioresource Technology, 2011, vol. 102, pp. 5177-5182.

(Continued)

*Primary Examiner* — Debbie K Ware
*Assistant Examiner* — Kailash C Srivastava
(74) *Attorney, Agent, or Firm* — Steven M. Hoffberg, Esq.; Ostrolenk Faber LLP

(57) ABSTRACT

A method of separating a lignin-rich solid phase from a solution suspension, by pretreating a lignocellulosic biomass with a pretreatment fluid having remove soluble components, colloidal material and primarily lignin containing particles; separating the pretreated lignocellulosic biomass from the pretreatment fluid with soluble components, colloidal material and primarily lignin containing particles; flocculating the separated pretreatment fluid with soluble components, colloidal material and primarily lignin containing particles using polyethylene oxide (i.e., PEO) or cationic Poly acrylamide (i.e., CPAM) as a flocculating agent; and filtering the flocculated separated pretreatment fluid with soluble components, colloidal material and primarily lignin containing particles to remove agglomerates.

23 Claims, 33 Drawing Sheets

(56) References Cited

U.S. PATENT DOCUMENTS

| | | |
|---|---|---|
| 6,074,473 A | 6/2000 | Nichols et al. |
| 6,074,856 A | 6/2000 | Wong et al. |
| 6,309,871 B1 | 10/2001 | Outtrup et al. |
| 6,361,989 B1 | 3/2002 | Svendsen et al. |
| 6,372,088 B1 | 4/2002 | Laivins et al. |
| 6,384,109 B1 | 5/2002 | Witecki, Jr. |
| 6,399,351 B1 | 6/2002 | Bj.o slashed.rnvad et al. |
| 6,414,080 B1 | 7/2002 | Loeffler et al. |
| 6,417,268 B1 | 7/2002 | Zhang et al. |
| 6,528,298 B1 | 3/2003 | Svendsen et al. |
| 6,566,114 B1 | 5/2003 | Kauppinen et al. |
| 6,623,948 B1 | 9/2003 | Outtrup et al. |
| 6,642,351 B1 | 11/2003 | Harlukowicz et al. |
| 6,663,780 B2 | 12/2003 | Heikkila et al. |
| 6,831,042 B2 | 12/2004 | Ristol et al. |
| 6,939,443 B2 | 9/2005 | Ryan et al. |
| 6,942,754 B2 | 9/2005 | Izumi et al. |
| 7,001,953 B2 | 2/2006 | Chen et al. |
| 7,109,005 B2 | 9/2006 | Eroma et al. |
| 7,183,093 B2 | 2/2007 | Kauppinen et al. |
| 7,258,732 B2 | 8/2007 | Nichols |
| 7,344,876 B2 | 3/2008 | Levine |
| 7,442,722 B2 | 10/2008 | Sui et al. |
| 7,476,272 B2 | 1/2009 | Defeo et al. |
| 7,514,007 B2 | 4/2009 | Chen et al. |
| 7,531,600 B1 | 5/2009 | Rey |
| 7,566,561 B2 | 7/2009 | Svendsen et al. |
| 7,585,652 B2 | 9/2009 | Foody et al. |
| 7,625,728 B2 | 12/2009 | Eroma et al. |
| 7,648,032 B2 | 1/2010 | Yuan et al. |
| 7,670,813 B2 | 3/2010 | Foody et al. |
| 7,727,746 B2 | 6/2010 | Foody et al. |
| 7,781,191 B2 | 8/2010 | Dunson, Jr. et al. |
| 7,807,419 B2 | 10/2010 | Hennessey et al. |
| 7,819,976 B2 | 10/2010 | Friend et al. |
| 7,846,705 B2 | 12/2010 | Kensch et al. |
| 7,910,338 B2 | 3/2011 | Hennessey et al. |
| 7,932,063 B2 | 4/2011 | Dunson, Jr. et al. |
| 7,960,153 B2 | 6/2011 | Czechowski et al. |
| 7,998,713 B2 | 8/2011 | Dunson, Jr. et al. |
| 8,021,516 B2 | 9/2011 | Chen et al. |
| 8,038,846 B2 | 10/2011 | Polverari et al. |
| 8,053,566 B2 | 11/2011 | Belanger et al. |
| 8,093,037 B2 | 1/2012 | Picataggio et al. |
| 8,105,398 B2 | 1/2012 | Morgan |
| 8,114,974 B2 | 2/2012 | Picataggio et al. |
| 8,187,860 B2 | 5/2012 | Franklin et al. |
| 8,202,709 B2 | 6/2012 | Tolan et al. |
| 8,222,010 B2 | 7/2012 | Franklin et al. |
| 8,227,236 B2 | 7/2012 | Picataggio et al. |
| 8,247,203 B2 | 8/2012 | Foody et al. |
| 8,263,368 B2 | 9/2012 | Svendsen et al. |
| 8,273,181 B2 | 9/2012 | Foody et al. |
| 8,287,732 B2 | 10/2012 | Chen et al. |
| 8,304,219 B2 | 11/2012 | Levine |
| 8,309,331 B2 | 11/2012 | Banerjee et al. |
| 8,318,461 B2 | 11/2012 | Tolan et al. |
| 8,338,139 B2 | 12/2012 | Lali et al. |
| 2002/0164731 A1 | 11/2002 | Eroma et al. |
| 2002/0195213 A1 | 12/2002 | Izumi et al. |
| 2003/0013172 A1 | 1/2003 | Gerendash |
| 2003/0022347 A1 | 1/2003 | Sjoholm et al. |
| 2003/0094252 A1 | 5/2003 | Sundar et al. |
| 2003/0203466 A1 | 10/2003 | Kauppinen et al. |
| 2003/0211958 A1 | 11/2003 | Svendsen et al. |
| 2004/0238133 A1 | 12/2004 | Lashofer et al. |
| 2005/0075497 A1 | 4/2005 | Utz et al. |
| 2005/0118130 A1 | 6/2005 | Utz et al. |
| 2005/0129643 A1 | 6/2005 | Lepilleur et al. |
| 2005/0148056 A1 | 7/2005 | Levine |
| 2005/0244934 A1 | 11/2005 | Foody et al. |
| 2006/0154352 A1 | 7/2006 | Foody et al. |
| 2006/0246563 A1 | 11/2006 | Eroma et al. |
| 2007/0031918 A1 | 2/2007 | Dunson, Jr. et al. |
| 2007/0031919 A1 | 2/2007 | Dunson, Jr. et al. |
| 2007/0031953 A1 | 2/2007 | Dunson, Jr. et al. |
| 2007/0037259 A1 | 2/2007 | Hennessey et al. |
| 2007/0072185 A1 | 3/2007 | Schnorr et al. |
| 2007/0175825 A1 | 8/2007 | Denney |
| 2007/0199903 A1 | 8/2007 | Denney |
| 2007/0207939 A1 | 9/2007 | Fenyvesi et al. |
| 2007/0218541 A1 | 9/2007 | Denney et al. |
| 2007/0221552 A1 | 9/2007 | Denney |
| 2007/0227971 A1 | 10/2007 | Denney |
| 2007/0241306 A1 | 10/2007 | Wehner et al. |
| 2008/0064064 A1 | 3/2008 | Kensch et al. |
| 2008/0102502 A1 | 5/2008 | Foody et al. |
| 2008/0193992 A1 | 8/2008 | Levine |
| 2008/0227161 A1 | 9/2008 | Levie et al. |
| 2008/0227182 A1 | 9/2008 | Anderson et al. |
| 2009/0004714 A1 | 1/2009 | Norholm et al. |
| 2009/0050134 A1 | 2/2009 | Friend et al. |
| 2009/0053777 A1 | 2/2009 | Hennessey et al. |
| 2009/0053800 A1 | 2/2009 | Friend et al. |
| 2009/0056201 A1 | 3/2009 | Morgan |
| 2009/0056707 A1 | 3/2009 | Foody et al. |
| 2009/0137438 A1 | 5/2009 | Lepilleur et al. |
| 2009/0170174 A1 | 7/2009 | Czechowski et al. |
| 2009/0209009 A1 | 8/2009 | Tolan et al. |
| 2009/0298149 A1 | 12/2009 | Wang et al. |
| 2009/0317864 A1 | 12/2009 | Svendsen et al. |
| 2009/0318571 A1 | 12/2009 | Utz et al. |
| 2010/0003733 A1 | 1/2010 | Foody et al. |
| 2010/0068768 A1 | 3/2010 | Tolan et al. |
| 2010/0071259 A1 | 3/2010 | Hu et al. |
| 2010/0075404 A1 | 3/2010 | Templeton |
| 2010/0189706 A1 | 7/2010 | Chang et al. |
| 2010/0196981 A1 | 8/2010 | Aharon et al. |
| 2010/0199548 A1 | 8/2010 | del Cardayre et al. |
| 2010/0221819 A1 | 9/2010 | Foody et al. |
| 2010/0279354 A1 | 11/2010 | de Crecy |
| 2010/0291653 A1 | 11/2010 | Ness et al. |
| 2010/0304420 A1 | 12/2010 | Gray |
| 2011/0039318 A1 | 2/2011 | Lehr |
| 2011/0117067 A1 | 5/2011 | Esteghlalian et al. |
| 2011/0129886 A1 | 6/2011 | Howard et al. |
| 2011/0146142 A1 | 6/2011 | Lee et al. |
| 2011/0165660 A1 | 7/2011 | Picataggio et al. |
| 2011/0165661 A1 | 7/2011 | Picataggio et al. |
| 2011/0183396 A1 | 7/2011 | Noda et al. |
| 2011/0195481 A1 | 8/2011 | Svendsen et al. |
| 2011/0201093 A1 | 8/2011 | Czechowski et al. |
| 2011/0224416 A1 | 9/2011 | Picataggio et al. |
| 2011/0229959 A1 | 9/2011 | Picataggio et al. |
| 2011/0250646 A1 | 10/2011 | Bazzana et al. |
| 2011/0275118 A1 | 11/2011 | De Crecy |
| 2011/0300585 A1 | 12/2011 | Banerjee et al. |
| 2011/0306100 A1 | 12/2011 | De Crecy |
| 2011/0306101 A1 | 12/2011 | De Crecy |
| 2012/0094340 A1 | 4/2012 | Morgan |
| 2012/0097194 A1 | 4/2012 | McDaniel et al. |
| 2012/0115192 A1 | 5/2012 | Lali et al. |
| 2012/0171732 A1 | 7/2012 | Norholm et al. |
| 2012/0184007 A1 | 7/2012 | Picataggio et al. |
| 2012/0184020 A1 | 7/2012 | Picataggio et al. |
| 2012/0282239 A1 | 11/2012 | Kensch |
| 2012/0282666 A1 | 11/2012 | Noda et al. |
| 2012/0283164 A1 | 11/2012 | Svendsen et al. |
| 2012/0322117 A1 | 12/2012 | Anton et al. |
| 2012/0329096 A1 | 12/2012 | Foody et al. |
| 2013/0032238 A1 | 2/2013 | Butler et al. |

OTHER PUBLICATIONS

Henrikki, Liimatainen, Acta Universitatis Ouluensis C Technica 334, Oulu University Press, Oulu, 2009.

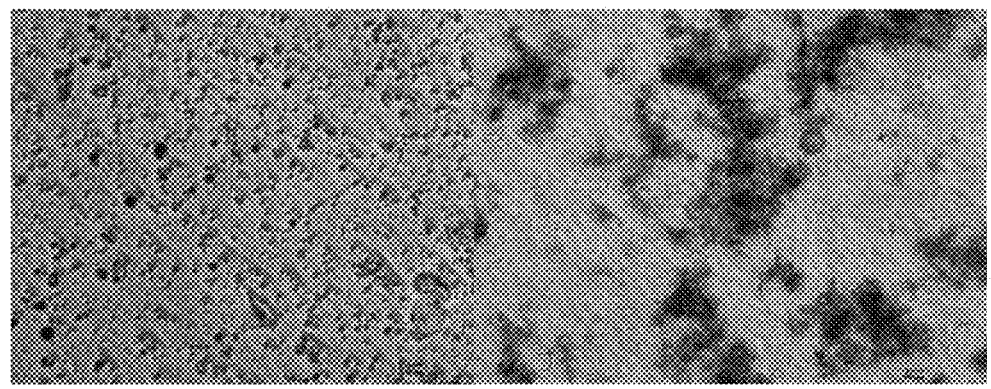
Fig. 11A Neat Extract    Fig. 11B pDADMAC
Fig. 11C Alum    Fig. 11D PEI
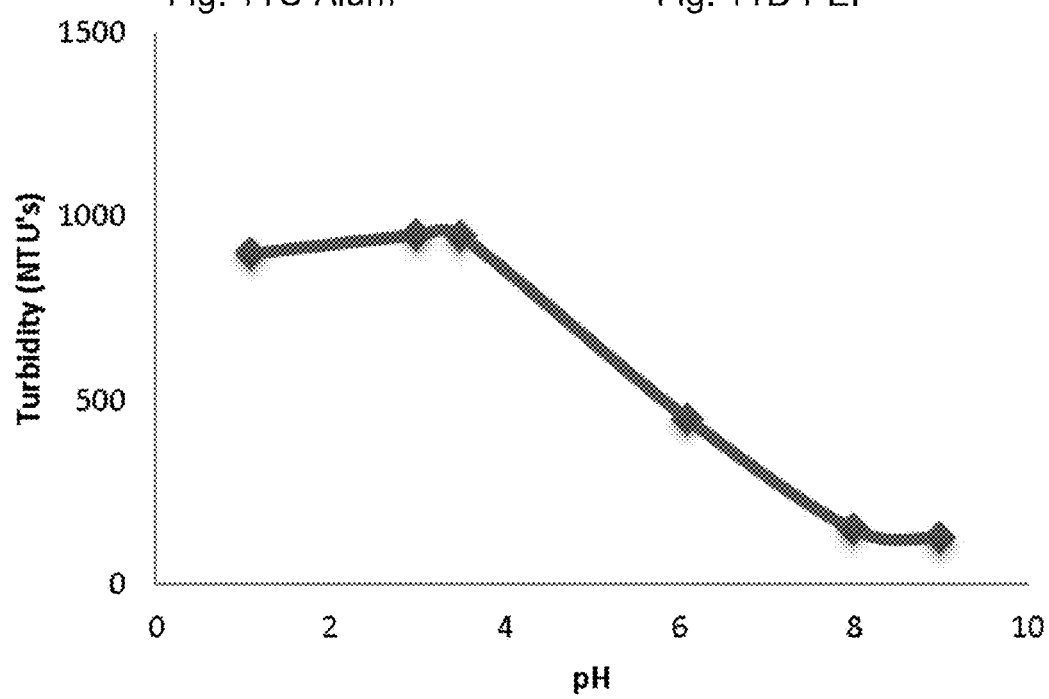
Fig. 12

METHOD TO SEPARATE LIGNIN-RICH SOLID PHASE FROM ACIDIC BIOMASS SUSPENSION AT AN ACIDIC PH

CROSS REFERENCE TO RELATED INVENTIONS

This application claims benefit of priority under 35 U.S.C. 365 of PCT/US2013/032238, filed Mar. 15, 2013, which claims benefit of U.S. Provisional Patent Application 61/613,196, filed Mar. 20, 2012, the entirety of which are expressly incorporated herein by reference.

STATEMENT OF GOVERNMENT SUPPORT

This invention was made with government support under DE-FG36-07GO87004 awarded by the U.S. Department of Energy. The government has certain rights in this invention.

FIELD OF THE INVENTION

This invention relates to field of biomass processing and separation of soluble components from suspended insoluble materials.

BACKGROUND OF THE INVENTION

Lignocellulosic materials such as wood are renewable and sustainable alternative resources for the production of fuels and plastics [47]. Accelerated industrial development around the globe has resulted in strong demand for petroleum as a fuel and also as a source for plastics and chemicals. Lignocellulosic feedstocks present an alternative to alleviate some of this pressure on petroleum resources in a particularly sustainable way. They present a significantly carbon neutral solution since biomass sequesters atmospheric carbon during its growth phase which is released during its combustion. Moreover, lignocellulosics present a source of fuels such as ethanol relieving the stress on corn, grain and such agricultural food sources. Societal awareness of such positive environmental benefits in addition to its obvious economic advantages has made the development and implementation of biobased energy from lignocellulosics imperative. Biomass processing is expected to occur in large biorefineries manufacturing a spectrum of fuel, chemical and material products in a scale efficient manner.

One class of biomass processes begins by hydrolyzing wood or the lignocellulosic raw material under different temperature and pressure conditions using dilute acid, hot water or mild alkaline solutions. The lignocellulosic hydrolyzates produced by this process consist of dissolved and colloidal oligomers of hemicelluloses, lignin and small quantities of extractives. The hemicelluloses in the hydrolyzates are transformed into biofuels or biobased plastic products by fermentation or other routes. Hydrolyzates must however be significantly purified and detoxified in order to conduct and maximize yields of the downstream fermentation processes.

Lignocellulosics are some of the most sustainable and renewable feedstocks for energy and materials in the future [1]. Woody biomass is a particularly attractive source because of its higher density and potential for integration with existing pulp and paper mill operations. Since hardwoods are rich in xylans and acetyl groups, pretreatment processes using aqueous solutions produces hydrolyzates which can be fermented to produce bioethanol and biobutanol. Pretreatment involves a variety of hydrolysis processes using mineral acids, mild alkalis or autohydrolysis using hot water and many of these have been investigated in integrated biorefinery processes [2]. The hydrolyzate solutions produced by such pretreatment processes are considerably complex, containing particulates, colloidal substances, dissolved and colloidal polymers from the carbohydrate and lignin solubilization reactions. In addition, low molecular weight organics such as acetic acid, methanol, furans and aromatics occur in the solution. A number of the compounds in the hydrolyzates are potent fermentation inhibitors. These include acetic acid, furan compounds (furfural and 5-hydroxy methyl furfural) and several products of lignin oxidation and degradation [3]. Some of these are in the colloidal phase whereas others, particularly the small molecule organics are in the solution phase. The colloidal particles not only inhibit the fermentation activities of microorganisms but also foul any filtration membranes used for separation and purification of extracts [4, 5]. Therefore, processes to separate such compounds from extracts are necessary and critical for viable biorefinery processes.

A hot water or acid hydrolysis may be followed by an enzyme hydrolysis to break down complex carbohydrates into fermentable monosaccharides and disaccharides. Commercially available hydrolysis enzymes include Cellic® HTec3, a concentrated hemicellulase that works alone or in combination with Cellic® CTec3 cellulase enzyme from Novozymes (Denmark). See: Zhang, Yi-Heng Percival, and Lee R. Lynd, "Toward an aggregated understanding of enzymatic hydrolysis of cellulose: noncomplexed cellulase systems." *Biotechnology and bioengineering* 88.7 (2004): 797-824; Fan, L. T., Yong-Hyun Lee, and David H. Beardmore. "Mechanism of the enzymatic hydrolysis of cellulose: effects of major structural features of cellulose on enzymatic hydrolysis." *Biotechnology and Bioengineering* 22.1 (1980): 177-199, Mandels, Mary, Lloyd Hontz, and John Nystrom. "Enzymatic hydrolysis of waste cellulose." *Biotechnology and Bioengineering* 16.11 (2004): 1471-1493; Philippidis, George P., Tammy K. Smith, and Charles E. Wyman. "Study of the enzymatic hydrolysis of cellulose for production of fuel ethanol by the simultaneous saccharification and fermentation process." *Biotechnology and bioengineering* 41.9 (1993): 846-853; Pääkkö, M., et al. "Enzymatic hydrolysis combined with mechanical shearing and high-pressure homogenization for nanoscale cellulose fibrils and strong gels." *Biomacromolecules* 8.6 (2007): 1934-1941; Yang, Bin, and Charles L. Wyman. "BSA treatment to enhance enzymatic hydrolysis of cellulose in lignin containing substrates." *Biotechnology and Bioengineering* 94.4 (2006): 611-617; Sun, Ye, and Jiayang Cheng. "Hydrolysis of lignocellulosic materials for ethanol production: a review." *Bioresource technology* 83.1 (2002): 1-11; Saddler, J. N., et al. "Enzymatic hydrolysis of cellulose and various pretreated wood fractions." *Biotechnology and bioengineering* 24.6 (1982): 13894402. Khodaverdi, Mandi, et al. "Kinetic modeling of rapid enzymatic hydrolysis of crystalline cellulose after pretreatment by NMMO." *Journal of industrial microbiology & biotechnology* (2012): 1-10; Mama, Patrick, et al. "Combination of enzymatic hydrolysis and ethanol organosolv pretreatments: Effect on lignin structures, delignification yields and cellulose-to-glucose conversion." *Bioresource Technology* (2012); Wiman, Magnus, et al. "Cellulose accessibility determines the rate of enzymatic hydrolysis of steam-pretreated spruce." *Bioresource Technology* (2012); Elliston, Adam, et al. "High concentrations of cellulosic ethanol achieved by fed batch semi simultaneous saccharification and fermentation of waste-paper." *Bioresource Technology* (2013); Kinnarinen, Teemu, et al.

"Effect of mixing on enzymatic hydrolysis of cardboard waste: Saccharification yield and subsequent separation of the solid residue using a pressure filter." *Bioresource technology* (2012); Wang, Lei, Richard Templer, and Richard J. Murphy. "High-solids loading enzymatic hydrolysis of waste papers for biofuel production." *Applied Energy* (2012); Li, Sujing, Xiaonan Zhang, and John M. Andresen. "Production of fermentable sugars from enzymatic hydrolysis of pretreated municipal solid waste after autoclave process." *Fuel* 92.1 (2012): 84-88; Dubey, Alok Kumar, et al. "Bioethanol production from waste paper acid pretreated hydrolyzate with xylose fermenting *Pichia stipitis.*" *Carbohydrate Polymers* (2012); Kinnarinen, Teernu, et al. "Solid-liquid separation of hydrolysates obtained from enzymatic hydrolysis of cardboard waste." *Industrial Crops and Products* 38 (2012): 72-80; Nørholm, Nanna Dreyer, Jan Larsen, and Frank Krogh Iversen. "Non-pressurised pre-treatment, enzymatic hydrolysis and fermentation of waste fractions." U.S. patent application Ser. No. 13/405,262; Das, Arpan, et al. "Production of Cellulolytic Enzymes by *Aspergillus fumigatus* ABK9 in Wheat Bran-Rice Straw Mixed Substrate and Use of Cocktail Enzymes for Deinking of Waste Office Paper Pulp." *Bioresource technology* (2012). Chen, Hui, et al. "Enzymatic Hydrolysis of Recovered Office Printing Paper with Low Enzyme Dosages to Produce Fermentable Sugars," *Applied biochemistry and biotechnology* (2012): 1-16. Yan, Shoubao, et al. "Fed batch enzymatic saccharification of food waste improves the sugar concentration in the hydrolysates and eventually the ethanol fermentation by Saccharomyces cerevisiae H058." *Brazilian Archives of Biology and Technology* 55.2 (2012): 183-192; Arora, Anju, et al. "Effect of Formic Acid and Furfural on the Enzymatic Hydrolysis of Cellulose Powder and Dilute Acid-Pretreated Poplar Hydrolysates." *ACS Sustainable Chemistry & Engineering* 1.1 (2012): 23-28; Wang, Lei, et al. "Technology performance and economic feasibility of bioethanol production from various waste papers." *Energy & Environmental Science* 5.2 (2012): 5717-5730; Vazana, Yael, et al. "Designer Cellulosomes for Enhanced Hydrolysis of Cellulosic Substrates." *Cellulases* (2012): 429; Van Dyk, J. S., and B. I. Pletschke, "A review of lignocellulose bioconversion using enzymatic hydrolysis and synergistic cooperation between enzymes—Factors affecting enzymes, conversion and synergy." *Biotechnology Advances* (2012); Menind, A., et al. "Pretreatment and usage of pulp and paper industry residues for fuels production and their energetic potential." *International Scientific Conference Biosystems Engineering, Tartu, Estonia*, 10-11 May 2012. Vol. 10. No. Special Issue I. Estonian Research Institute of Agriculture, 2012; Han, Lirong, et al. "Alkali pretreated of wheat straw and its enzymatic hydrolysis." *Brazilian Journal of Microbiology* 43.1 (2012): 53-61; Holm, Jana, et al. "Pretreatment of fibre sludge in ionic liquids followed by enzyme and acid catalysed hydrolysis." *Catalysis Today* (2012), each of which is expressly incorporated herein by reference.

See also, US Pub. Pat. Appl. 20120329096; 20120322117; 20120283164; 20120282666; 20120282239; 20120184020; 20120184007; 20120171732; 20120115192; 20120097194; 20120094340; 20110306101; 20110306100; 20110300585; 20110275118; 20110250646; 20110229959; 20110224416; 20110201093; 20110195481; 20110183396; 20110165661; 20110165660; 20110146142; 20110129886; 20110117067; 20110039318; 20100304420; 20100291653; 20100279354; 20100221819; 20100199548; 20100196981; 20100189706; 20100075404; 20100071259; 20100068768; 20100003733; 20090318571; 20090317864; 20090298149; 20090209009; 20090170174; 20090137438; 20090056707; 20090056201; 20090053800; 20090053777; 20090050134; 20090004714; 20080227182; 20080227161; 20080193992; 20080102502; 20080064064; 20070241306; 20070227971; 20070221552; 20070218541; 20070207939; 20070199903; 20070175825; 20070072185; 20070037259; 20070031953; 20070031919; 20070031918; 20060246563; 20060154352; 20050244934; 20050148056; 20050129643; 20050118130; 20050075497; 20030211958; 20030203466; 20030022347; 20030013172; 20020195213; 20020164731; and U.S. Pat. Nos. 8,338,139; 8,318,461; 8,309,331; 8,304,219; 8,287,732; 8,273,181; 8,263,368; 8,247,203; 8,227,236; 8,222,010; 8,202,709; 8,187,860; 8,114,974; 8,105,398; 8,093,037; 8,053,566; 7,998,713; 7,960,153; 7,932,063; 7,910,338; 7,846,705; 7,819,976; 7,807,419; 7,781,191; 7,727,746; 7,670,813; 7,625,728; 7,585,652; 7,566,561; 7,344,876; 7,183,093; 7,109,005; 6,942,754; 6,663,780; 6,623,948; 6,566,114; 6,528,298; 6,399,351; 6,361,989; 6,309,871; 6,074,856; 5,888,806; 5,736,032; 5,733,758; 5,589,164; 5,587,157; and 5,352,444, each of which is expressly incorporated herein by reference in its entirety.

One of the major obstacles to the large scale industrial fermentation of hydrolyzates is the lack of efficient and cost effective separation and purification methods. The major constituents of woody biomass (cellulose, hemicellulose and lignin) cannot be isolated simultaneously as polymers and several processes must be employed involving the degradation of at least one polymer. One approach to solving the obstacle problems is to initially treat the biomass to degrade hemicellulose by extraction or autohydrolysis (hot water extraction process) in the absence of mineral acids or caustics thereby leaving both cellulose and lignin as essentially undegraded polymers [50, 51]. Autohydrolysis is of interest because water and biomass are the only reagents, without complicating and costly side reaction.

A review of possible separation techniques useful in biorefineries was recently published by Huang et al [6]. Detoxification methods include extraction [7], overliming [8, 9], adsorption on zeolites [10, 11], activated carbon [12], the application of ion exchange resins [13] and hybrid processes such as adsorptive membranes [14]. Filtration is one such alternative, followed by liquid-liquid extraction for separating acetic acid and furfural. Reverse osmosis membranes have also been applied to separate acetic acid and furfural from the extracts to yield a concentrated hemicellulose rich retentate and a dilute acetic acid permeate. Fouling of the membranes used in nanofiltration or reverse osmosis is a serious problem leading to decaying permeate fluxes and renders the separation uneconomical on large scale [5].

Polyelectrolytes have been used in the past for the clarification of lignocellulosic suspensions to enhance solid liquid separations. Hydrolyzates produced by hot-water treatment of sugar maple (*Acer saccharum*) wood chips were flocculated by the application of a cationic polymer—poly-diallyl dimethyl ammonium chloride (pDADMAC) [15]. The hydrolyzates were highly turbid (>10000 NTUs) and the average particle size ranged from ~220 nm to 270 nm, the larger particles obtained from more severe treatments. The effect of polymers on the colloidal stability depends on the specifics of adsorption of the polymer on the colloidal particles [19, 20].

Polymers flocculate colloidal suspensions generally through the mechanisms of charge neutralization, formation of patches of opposite charge and subsequent attraction (referred to as patching) and bridging [see e.g. 43]. Flocculation depends on the size of the polymer molecule both in solution and after adsorption (its conformation), charge density, polymer concentration, presence of other electrolytes and the mode of addition [21-29]. Poly-ethylene imine (PEI), and (pDADMAC) are low molecular weight and high charge density polymers which act by forming cationic patches on particles resulting in attractive interactions between colloidal particles [30, 31]. The introduction of cationic countercharges reduces the extent of the electrical double layers and also contributes to the flocculation process. Cationic polyelectrolytes are subject to changes in charge and size in solution upon alteration of pH and ionic strength. Furthermore, the adsorption of the polyelectrolytes on an oppositely charged surface may change with these solution properties. Since these polymers are polybase, addition of protons (reduction in pH) will result in protonation and subsequent expansion due to repulsion [32, 33]. High molecular weight cationic Poly acrylamide (CPAM) flocculates suspensions by adhering to particle surfaces and forming a bridge between them [34-37]. It is also known that the mechanism of flocculation, i.e. patching or bridging effects the rate and extent of dewatering achieved, i.e. the dynamics of the fluid-particle phase separation processes such as filtration and sedimentation.

The raw extracts from woody biomass (which woody biomass itself is separately used as a feedstock for pulp paper production) consist of water soluble and insoluble substances, mostly as monomers and oligomers of sugars, acetic acid, methanol, aromatic compounds, other low molecular weight extractable substances and fractions of lignin and residual particles [49,51].

These raw extracts, produced by water treatment, contain significant quantities of colloidal material or particulates composed mostly of lignin and its derivatives. The colloidal particles not only inhibit the fermentation activities of some microorganisms, but also foul any filtration membranes used for separation and purification of extracts. Separation and purification of these contaminant components from hot water extracts is an important step in separation processes of the biorefinery industry.

The particulate phase of the wood extracts, containing colloidal particles which foul and plug membranes used in the separation and purification of wood extracts [52, 53], comprise suspended colloidal particles constantly and randomly bombarded from all sides by molecules of the liquid, making them move in a zigzag path. This type of movement is known as Brownian motion and increases in significance, as particle size decreases. Since the mass of a colloidal particle is also small, its settling rate under the influence of gravity is slow. When the effect of Brownian motion dominates, it becomes very difficult and an unacceptably slow process to separate the particles from the liquid by gravity sedimentation [52, 53].

Colloidal particles, usually anionically charged, which cannot be removed from a liquid by sedimentation within a short period of time (less than few hours), are typically converted into aggregates by coagulation or flocculation. The larger aggregates have more mass and the influence of gravity dominates over Brownian motion so that sedimentation occurs in a relatively short time. Flocculation and sedimentation of colloidal suspensions play an important role in separation of solids particles from liquid media. The particulate phase in wood extracts can be separated by treating with polyelectrolyte flocculating agents. Polymer induced flocculation is also used to enhance the separation of colloidal particles in wood extracts [48, 49].

The effect of polymers on colloidal stability depends on the peculiarities of the colloidal particle adsorption to the surface of the polymer. The polymers can destabilize the colloidal particles through charge neutralization, electrostatic patch and bridging flocculation. The time dependence and efficiency of the flocculation process is a function of many variables, including the structure of the molecule, its molecular mass, charge density, concentration of the polymer solution, content of the electrolytes, and the mode of addition of polymer solution to suspension [54].

Autohydrolysis (hot water extraction) is of interest because water and biomass are the only reagents. The raw extracts from woody biomass consists of water soluble and insoluble substances, mostly as monomers and oligomers of sugars, acetic acid, methanol, aromatic compounds, other low molecular weight extractable substances and fractions of lignin and residual particles. Raw extracts produced by water treatment contains significant quantities of colloidal material. These particulates are composed mostly of lignin and its derivatives. Flocculation and sedimentation of colloidal suspensions play an important role in separation of solids particles from liquid media.

Hydrolyzates produced by pretreatment of lignocellulosic materials contain significant colloidal material that is anionically charged. Many of the compounds that are present in the hydrolyzates are inhibitory to fermentation and interfere with downstream separations. The flocculation of this colloidal material makes separations easier by sedimentation and can reduce the fouling tendencies of membranes. It can also reduce the toxicity of the hydrolyzates to fermentation microorganisms.

The interaction of PEO with modified lignin-type compositions has been studied in the past [53, 54, 55, 56, 57]. PEO is able to adsorb on unbleached Kraft or sulphite fibers (i.e., wood biomass modified by the Kraft or sulfite process), latex or clay without any cofactor, but does not adsorb on other particles such as calcium carbonate and bleached Kraft fibers by itself. In the latter cases, it is necessary to use another compound that interacts with PEO and the mineral surfaces. Such compounds are called cofactors and normally have aromatic groups in them [53, 54, 57]. The PEO polymer is able to form hydrogen bonds with other electron acceptor compounds because of the unshared electron pair of the ether oxygen. The formation of complexes between PEO and lignin has been described as a complex bridging association-induced flocculation [53, 54, 55, 56, 57]. PEO was therefore used in the paper making process and the treatment of charge-modified solid biomass.

FIG. 16 shows example process steps in a biomass processing system.

FIG. 19 shows a composition analysis of hot water extracted woodchips.

TABLE 1

Comparison of various technologies:

| Hydrolyzate | Flocculant | Charge | Investigator | Dosage | Temp (° C.) | pH | Efficiency | Separation Process; Remarks |
|---|---|---|---|---|---|---|---|---|
| Wood Hydrolyzate (10x Diluted) | pDADMAC | Cationic | Duarte, B. V. Ramarao (1) | 0-47.3 ppm | 25 | 3.5 | Highly Efficient | Flocculation and Sedimentation; Expensive |
| Wood | CPAM | Cationic | R Singh, | 0-200 | 25 | 3.5 | none- low | Flocculation and |

TABLE 1-continued

Comparison of various technologies:

| Hydrolyzate | Flocculant | Charge | Investigator | Dosage | Temp (° C.) | pH | Efficiency | Separation Process; Remarks |
|---|---|---|---|---|---|---|---|---|
| Hydrolyzate | | | B. V. Ramarao (2) | ppm | | | efficiency | UV Analysis; Low Cost |
| Synthetic solution (xylose, glucose, HMF Furfural, diethylamine) | PEI | Cationic | Carter, Menkhaus (3) | 0.1-1 Molar Eq. | 22 | 3.4 | | Flocculation/adsorption and filtration and centrifugation |
| Lignocellulosic slurries (Pine Wood hydrolyzates) | Kemira C1592 | Cationic | Burke, Menkhaus (4) | 1000-5000 mg/L | 22 | 5 | large | Flocculation and Filtration, centrifugation |
| Superfloc C-1592 PG | C1594 | Cationic | | | | | medium | |
| Polyacrylamide [PC] | C1598 | Cationic | | | | | medium | |
| C1594 Kemira | 130 GVHRS | Anionic | | | | | low | |
| | 140 GVHRS | Anionic | | | | | low | |
| Anionic PAM | A 1883 RS | Anionic | | | | | low | |
| Anionic PAM | A1849 RS | Anionic | | | | | low | |
| Nonionic PAM | N 1986 | Neutral | | | | | low | |
| Corn grain Stillage Liquid Stream | Kemira C1592 | Cationic | Menkhaus et al., (5) | 0-5.6 mg/g | 22 | 4 | | Flocculation and Centrifugation/Filtration |
| Cationic PAM | C 4512 | Cationic | | | | | | |
| Cationic PAM | C 4516 | Cationic | | | | | | |
| Anionic PAM | A1883 | Anionic | | | | | | |
| Anionic PAM | A 130 | Anionic | | | | | | |
| Anionic PAM | A 140 | Anionic | | | | | | |
| Nonionic PAM | N 1986 | Neutral | | | | | | |
| Pre Hydrolysis Liquor (From Kraft Based dissolving pulp Production Process) | PEO | | Shi, Ni (6) | 0-350 mg/L | N/A | 3.7-1.5 | | Combined Acidification/PEO Flocculation and centrifugation |
| Pre Hydrolysis Liquor (Liquor produced after kraft pulping from bottom of digestor) | PEO | | Shi, Ni (7) | 10-100 ppm | RT | 2 | no separation - negligible | Acidification and flocculation |
| | PAC (Poly Aluminum Chloride) | | | 100 ppm | RT | 2 | no separation | |
| | EC (Ethyl Acetate) | | | 1.5%-4% | RT | 2 | medium | |
| Wood Hydrolyzate | pDADMAC | Cationic | L R Yasarla, B. V. Ramarao | 0-150 ppm | 15-25 | 3.5-8.0 | Highly Efficient | Flocculation and Sedimentation Expensive |
| Wood Hydrolyzate | Alum | Poly-electrolyte | L R Yasarla, B. V. Ramarao | 0.01-0.25M | 15-25 | 3.5-8.0 | Medium - high | Flocculation and Sedimentation; low cost |
| Wood Hydrolyzate | PEI | Cationic | L R Yasarla, B. V. Ramarao | 0-150 ppm | 15-25 | 3.5-8.0 | Highly Efficient | Flocculation and Sedimentation; low cost |
| Wood Hydrolyzate | PEO Medium MW | Neutral | L R Yasarla, B. V. Ramarao | 0-40 ppm | 15-25 | 3.5-8.0 | No Separation | Flocculation and Sedimentation; low cost |
| Wood Hydrolyzate | PEO Higher MW | Neutral | L R Yasarla, B. V. Ramarao | 0-150 ppm | 15-25 | 3.5 | Highly Efficient | Flocculation and Sedimentation |
| Wood Hydrolyzate | CPAM Medium MW | Cationic | L R Yasarla, B. V. Ramarao | 0-25 ppm | 15-25 | 2-8.5 | Highly Efficient | Flocculation and Sedimentation; low cost |
| Wood Hydrolyzate | CPAM Higher MW | Cationic | L R Yasarla, B. V. Ramarao | 0-30 ppm | 15-25 | 3.5 | Highly Efficient | Flocculation and Sedimentation |
| Wood Hydrolyzate | C-Starch | Cationic | L R Yasarla, B. V. Ramarao | 0-75 g/100 ml | 15-25 | 3.5 | No Separation | Flocculation and Sedimentation |
| Wood Hydrolyzate | Alum + PEI | | L R Yasarla, B. V. Ramarao | 0.15M + 25 ppm | 15-25 | 3.5 | Efficient | Flocculation and Sedimentation; low cost |

TABLE 1-continued

Comparison of various technologies:

| Hydrolyzate | Flocculant | Charge | Investigator | Dosage | Temp (° C.) | pH | Efficiency | Separation Process; Remarks |
|---|---|---|---|---|---|---|---|---|
| Wood Hydrolyzate | APAM | Anionic | L R Yasarla, B. V. Ramarao | 0-40 ppm | 15-25 | 3.5 | Under Investigation | Flocculation and Sedimentation |

(1) Bioresource Technology (submitted 29 Sep. 2009, accepted 26 May 2010).
(2) SUNY-ESF New Technology Disclosure 2008
(3) Biotechnology and Bioengineering (submitted 29 Nov. 2010, accepted 14 Mar. 2011)
(4) Biomass and Bioenergy (submitted 13 Aug. 2009, accepted 20 Aug. 2010)
(5) Bioresource Technology (submitted 23 Feb. 2009, accepted 2 Nov. 2009)
(6) Bioresource Technology (submitted 18 Dec. 2010, accepted 24 Jan. 2011)
(7) Bioresource Technology (submitted 24 Apr. 2010, accepted 18 Aug. 2010)

SUMMARY OF THE INVENTION

As described above, lignocellulosic hydrolyzates produced by hydrothermal treatment of wood chips contain hemicellulose sugars, acetic acid and significant quantities of colloidal material. These particles are mostly composed of lignin and its derivatives, which have a wide range of particle size distribution. Separation of these colloidal materials is necessary to improve fermentability of sugars into biofuels and other bioproducts. Flocculation of wood hydrolyzates prior to microfiltration improves their filterability.

The hydrolyates may be further processed by enzymatic digestion prior to flocculation, without departing from the scope of the invention.

Biofuels from lignocellulosic materials like wood are renewable and sustainable alternatives to petroleum and other fossil fuels. In the forest biorefinery the production of liquid fuels and bioplastics fermentable sugars are extracted with hot water after which the hydrolyzates are purified and detoxified. The purification of the hydrolyzate stream and the separation of fermentable sugars from it thus constitute an important step in biorefinery processes. Raw lignocellulosic hydrolyzates produced by acid or water treatment contain hemicelluloses (primarily xylooligomers, xylose and xylan), acetic acid and significant quantities of colloidal material. The particulates are composed mostly of lignin and its derivatives which are in the range between nanometers and micrometers in particle size, and are anionic in nature. The colloidal stability of the extracts plays a critical role in the separation and purification of the wood extracts. These colloidal particulates inhibit the fermentation activities of microorganisms and the hemicelluloses in the wood extracts, and need to be separated from these inhibitory components.

Hydrolyzates of hardwood, such as sugar maple, may be separated by hot water processing, using cross flow microfiltration and polymer induced flocculation. In the polymer-induced flocculation, the dynamics of flocculation of wood extracts with Alum, PEI, pDADMAC and PEO were studied. The variation in zeta potential measurements showed that the colloidal particles in wood extracts are charge neutralized initially, and particles were found to be increased in size after charge neutralization. The rate of sedimentation of aggregated particles was measured by turbidity of supernatants of the dispersed solution as a function of time. The optimal concentrations of flocculating agents to flocculate the colloidal particles were measured by both charge neutralization and rate of sedimentation. The pH sensitivity of flocculating agents was tested by varying the pH of wood extract between 3.5 and 8.0. The optimal concentrations of flocculating agents for sedimentation were found for different pH conditions. For microfiltration separation, ceramic micro filters of two different pore sizes: 0.2 μm and 0.01 μm are used as a function of membrane fouling. Cross flow permeation fluxes were determined for different transmembrane pressures and cross flow velocities. Colloidal and particulate materials were separated from the extracts, with turbidity reductions of 94 to 100% in most cases.

The dynamics of flocculation of lignocellulosic hydrolyzates were studied with a variety of charge based flocculating agents: electrolytes (Alum) and polymers (PEI, pDADMAC, CPAM). Trivalent cations were the particularly effective suspension destabilizers among the electrolytes, while the cationic polymers could cause flocculation and also redispersion depending on their dosage levels. Flocculation reduced the hydrolyzates' turbidity from >10,000 to under 20. With PEI and pDADMAC, flocculation occurred rapidly when the zeta potential of the colloid was close to zero, showing that charge neutralization is the significant destabilizing mechanism. At higher dosages, redispersion occurred indicating that patching is also important in flocculation. Flocculation by PEI was sensitive to pH (from hydrolyzate pH of 3 to 8) with increased dosage necessary at higher pH values. The cationicity of PEI is reduced at higher pH which results in loss of its effectiveness. On the other hand, the zeta potential was largely unaffected with CPAM dosage indicating the dominance of bridging flocculation. Floc sizes ranged up to 3 mm, depending on flocculant dose and pH.

In addition, the non-ionic agent Polyethylene Oxide (PEO) was also investigated. The rate of flocculation was monitored by sedimentation of the suspensions. The optimal dosages of PEO depended on the temperature and extract concentrations and varied between 20 to 50 ppm. Although the pH of the extracts was varied from about 2 through about 9, the effect on suspension stability was minimal. The optimal temperature for flocculation at optimal polymer dosage was >21.5° C. The composition of hemicelluloses in the supernatants after flocculation were not substantially altered from the raw extract, showing that flocculation does not remove significant amount of fermentable sugars. Hence, such pretreatment clarification is not expected to affect downstream bioproduct yields. Significant removal of lignin in particulate, colloidal and soluble forms was observed by the action of PEO. The flocculated extract was filtered and the filtrate showed a 99.5% reduction in turbidity, from 12,000 NTUs in the raw extract to 50 NTUs in the filtrate.

Acetic acid is frequently a significant component of lignocellulosic hydrolyzates and can inhibit their fermentation by microorganisms such as *S. cerevesaie*. The inhibitory action of acetic acid is known to be significant when its concentration is greater than 10 g/l. It is possible to reduce the acidity of the lignocellulosic hydrolyzates by targeting the acetic acid (and possibly other small molecule organic acids such as formic or lactic acids) by neutralization with calcium carbonate. This is a variant of the conventional method for detoxification of lignocellulosic hydrolyzates by 'overliming'. In the conventional process, lime (i.e. CaO or Ca(OH)$_2$) is used to increase the pH of the hydrolyzates to around 10, resulting in lignin solubilization, and neutralization of the acetic acid, forming the acetate and the calcium ions. Following the addition of lime, the hydrolyzates are treated with activated carbon to adsorb the lignin and the resulting largely lignin free solution is treated with sulfuric acid to bring the pH down to the range of 5 for further fermentation.

According to the present technology, a polymeric flocculant, such as the non-ionic polymer PEO, is added first to sequester and remove the colloidal lignin, extractives and other interference components. This is followed by addition of Calcium Carbonate (e.g., precipitated calcium carbonate, known as "PCC") in the appropriate dosages to increase the pH and neutralize the acetic acid.

It is possible that the form of the calcium carbonate can impact its performance. Recent literature shows that the adsorption of lignin onto PCC is impacted by the morphology of PCC. See, e.g., Rojas, Orlando J., and Martin A. Hubbe. "The dispersion science of papermaking" *Journal of dispersion science and technology* 25.6 (2005): 713-732; Kim, Birm June. "*The effect of inorganic fillers on the properties of wood plastic composites*" Diss, Seoul National University, 2012; Subramanian, Ramjee. "Engineering fine paper by utilising the structural elements of the raw materials" (2008); Gupta, Himanshu, and Liang-S. Fan, "Carbonation-calcination cycle using high reactivity calcium oxide for carbon dioxide separation from flue gas." *Industrial & engineering chemistry research* 41.16 (2002): 4035-4042; Sundar, Meenakshi V., and Steven A. Fisher. "Cellulosic products containing improved percentage of calcium carbonate filler in the presence of other papermaking additives" U.S. Patent Application 2003/0094252; Koivunen, Kimmo, et al. "Novel nanostructured PCC fillers" *Journal of materials science* 44.2 (2009): 477-482; Guvendiren, Murat, Paul A. Heiney, and Shu Yang, "Precipitated Calcium Carbonate Hybrid Hydrogels: Structural and Mechanical Properties" *Macromolecules* 42.17 (2009): 6606-6613; Gibbs, Andrea, Robert Pelton, and Rongjuan Cong. "The influence of dextran derivatives on polyethylene oxide and polyacrylamide-induced calcium carbonate flocculation and floc strength" *Colloids and Surfaces A: Physicochemical and Engineering Aspects* 159.1 (1999): 31-45: Pang, Peter, et al. "Surface analysis of ground calcium carbonate filler treated with dissolution inhibitor" *Industrial & engineering chemistry research* 40.11 (2001): 2445-2451; Watkins, Gary, Mikko Makela, and Olli Dahl. "Innovative use potential of industrial residues from the steel, paper and pulp industries—a preliminary study" *Progress in industrial Ecology, an international Journal* 7.3 (2010): 185-204; Gaudreault, Roger, et al. "The Structure And Strength Of Flocs Of Precipitated Calcium Carbonate Induced By Various Polymers Used In Papermaking" 14th Fundamental Research Symposium, Oxford, September 2009, p. 1193; and Subramanian, Ramjee, "Engineering fine paper by utilising the structural elements of the raw materials" (2008) Ph.D. Thesis, Aalto University, aaltodoc.aalto.fi/handle/ 123456789/4527, each of which is expressly incorporated herein by reference in its entirety.

In accordance with the present technology, PEO has been effectively utilized in the treatment of a lignocellulosic particulate suspension derived from biomass. The PEO flocculated liquid is then filtered, resulting in a non-turbid liquid that is suitable for fermentation or bioprocessing, that is, the upstream processes result in a non-toxic environment in which biological action such as fermentation can occur. The bioprocessing can be, for example, a biofuel process or the like. The flocculate may also be used as biomass, for example in a papermaking process.

The separation of soluble sugar maple wood extracts from this filtrate after non-ionic polymer Polyethylene Oxide (PEO) flocculation of lignin component suspended particles, which typically has few industrial uses, and is thus normally waste liquid, was efficiently performed.

It is therefore an object to provide a method of separating a lignin-rich solid phase from a solution, and corresponding apparatus, comprising: dividing a lignocellulosic biomass into a residual lignocellulosic biomass, and a suspension comprising soluble components, colloidal material, and primarily lignin containing particles, using a pretreatment fluid; flocculating the suspension using polyethylene oxide (PEO) as a flocculating agent; and separating the flocculated suspension to remove agglomerates. Alternately, the flocculating may employ cationic polyacrylamide (CPAM), which is preferably employed within a pH range of about 2-10.

The dividing may comprise, for example, a sedimentation, centrifugation, or a microfiltration. The pretreatment fluid may comprises a hot water extraction fluid, e.g., may consist essentially of hot water. As should be understood, a hot water solution has advantages with respect to environmental impact and microbial action on the solution. Likewise, the flocculating agent is preferably compatible with subsequent microbial action on the pretreatment fluid containing the solution portions, separated from the agglomerates. Thus, for example, the non-agglomerated portion of the flocculated suspension may be microbially processed or fermented.

The flocculating is preferably conducted at a temperature over 21.5° C. The flocculating may be performed for less than about 2 hours.

The separating may comprise a filtering, for example through a cloth or ceramic filter, and the pore size of the filter may be, for example, less than 10 microns, or less than 2 microns.

If the flocculating agent is CPAM, or another component that might interfere with subsequent microbial action on the fluid, or for other reasons, the residual CPAM or other component may be removed from a non-agglomerated portion of the flocculated suspension. For example, since CPAM is cationic, it can interact with an anionic agent for removal.

It is a further an object to provide a method of separating a lignin-rich solid phase from a solution, comprising: pretreating a lignocellulosic biomass with a pretreatment fluid to remove soluble components, colloidal material and primarily lignin containing particles; separating the pretreated lignocellulosic biomass from the pretreatment fluid with soluble components, colloidal material and primarily lignin containing particles; flocculating the separated pretreatment fluid with soluble components, colloidal material and primarily lignin containing particles using PEO as a flocculating agent, or using CPAM wherein the pretreatment fluid has a pH>2 and pH<10; and filtering the flocculated separated pretreatment fluid with soluble components, colloidal material and primarily lignin containing particles to remove agglomerates.

Another object to provides an apparatus for treating lignocellulosic biomass, comprising a vessel configured to treat the biomass with an extractant, such as hot water, to extract soluble components, colloidal material and primarily lignin containing particles from the biomass, yielding a residual biomass and a solution; a first separation device configured to separate the solution from the residual biomass, for example by filtering, sedimentation, centrifugation, or the like; a feed to add a flocculating agent to the solution, wherein the flocculating agent comprises polyethylene oxide or cationic polyacrylamide (pH>2, pH<10); and a second separation device configured to separate the flocculated portion of the suspension from the non-flocculated portion of the suspension. Preferably, the apparatus is configured to extract solubles from the lignocellulosic biomass, such as sugars, to separate lignin from the sugars, and provide from the second separation device a solution suitable for microbial action or fermentation.

BRIEF DESCRIPTION OF THE DRAWINGS

FIGS. 11A-11D show micrographs of flocculated particles for a neat extract (FIG. 11A), pDADMAC (FIG. 11B), Alum (FIG. 11C), and PEI (FIG. 11D);

FIG. 12 shows a graph of turbidity neat extract hydrolyzate at different suspension vs. pH (adj. with NaOH) (Turbidities measured at 10× dilution);

DETAILED DESCRIPTION OF THE PREFERRED EMBODIMENTS

Hydrolyzates

Figure 17:
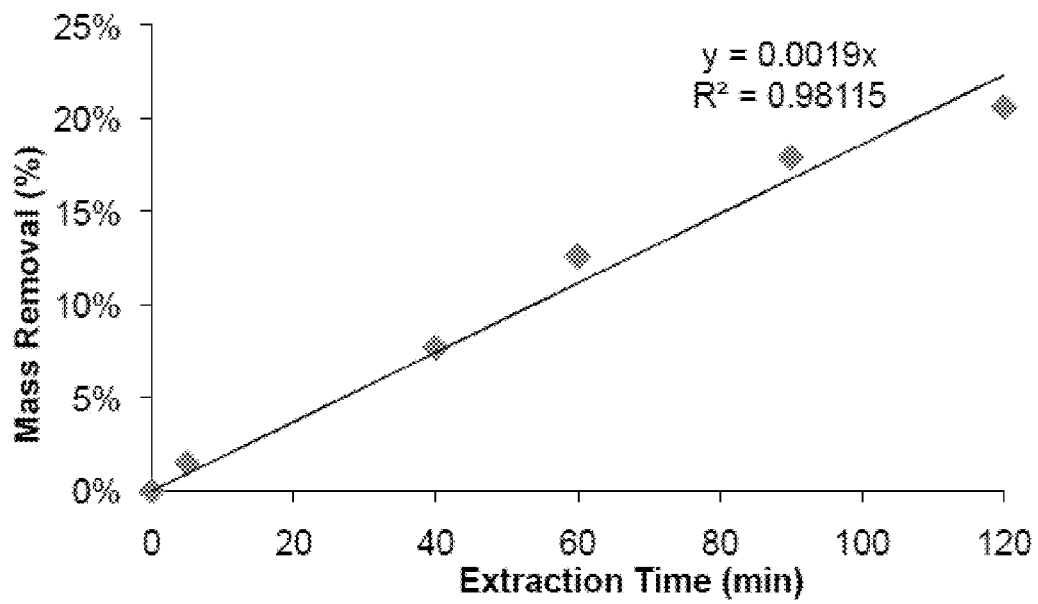
FIG. 17 shows a graph of mass recovery vs. extraction time.
Figure 18:
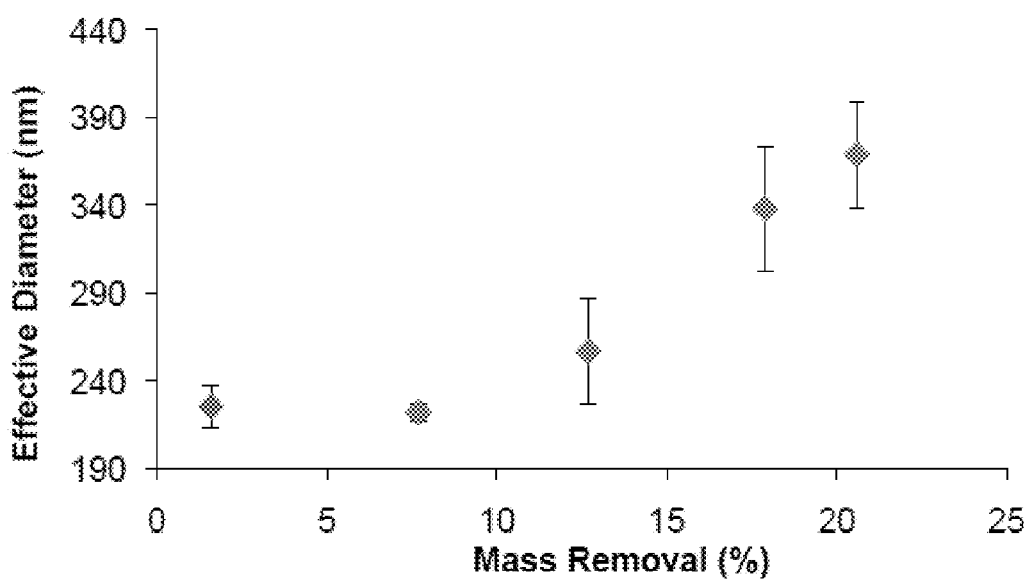
FIG. 18 shows a graph of effective diameter vs. mass removal.
Figure 19:
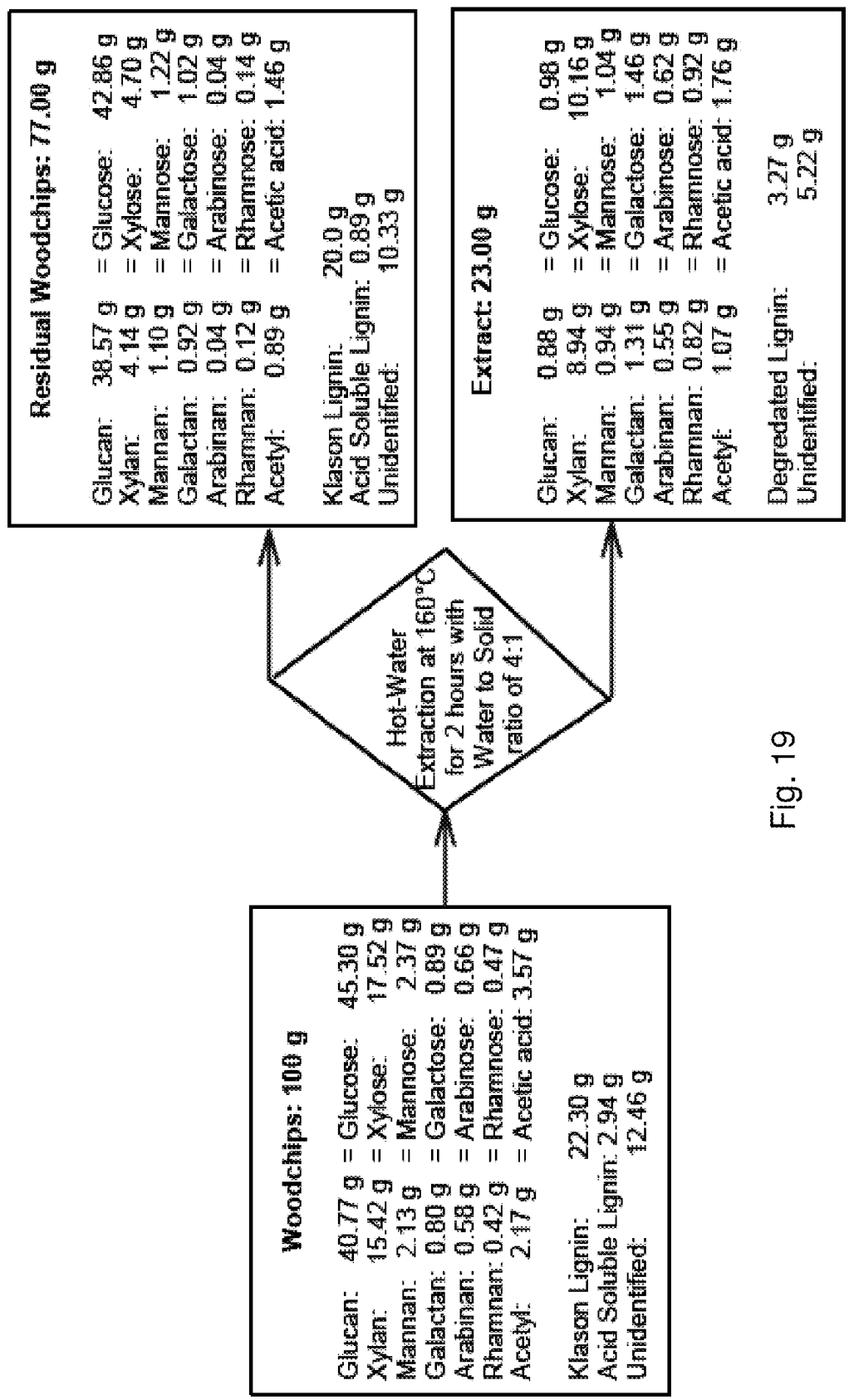
FIG. 19 shows a chart showing extraction content.

Autohydrolysis or hot water extraction were carried out in a MK digester using 500 g oven dried sugar maple wood chips and 4:1 liquor (water) to wood ratio at 160° C. for 2 hours. FIGS. 17 and 18 show the mass removal over time and effective diameter of particle size as a function of mass removed, respectively.

Particle size and zeta potential of the wood hydrolyzate were measured using a Brookhaven Particle Size and Zeta Potential Analyzer (90 Plus® and ZetaPlus®, Holtsville, N.Y.). A Micro100 turbidimeter (HF Scientific Inc., Fort Myers, Fla.) was used to measure turbidity of the samples (Nephelometric turbidity units, NTUs).

It was necessary to dilute the samples at least 10 fold to measure the turbidity, particle size and zeta potential. All the dilutions required were performed with filtrated (100 nm filter) reverse osmosis water.

Sugar maple (*Acer saccharum*) chips were prepared from debarked wood logs in a Carthage chipper. The chips were screened and air-dried before extraction. 500 g (on over dried basis) of the wood chips were placed in the digester and 2000 ml of reverse osmosis purified water was added (water-wood ratio of 4:1). The digester temperature was increased linearly from the initial room temperature up to 160° C. (ramp time 15 min) and then held for 120 min. at the extraction condition that corresponds to the maximum dissolved solids [5, 15, 40] and the highest xylose concentration in the extract. At the end of the extraction, the digester was cooled, depressurized and the reaction mixture was withdrawn. The extraction liquor was separated, collected and the chips were washed, dried and weighed.

Supernatant, Sediment and Hydrolyzate characterization

Physical Characterization

The turbidity of the solutions was measured (in NTUs) using a Micro100 laboratory turbidimeter [HF Scientific Inc, Fort Myers, Fla., USA]. It was necessary to dilute the sampled solution 10× to measure the turbidity from which the true turbidity was calculated. All the dilutions required were performed with filtrated reverse osmosis water. Particle size and zeta potential of the wood hydrolyzates were measured using a Brookhaven Particle Size and Zeta Potential Analyzer (90 Plus® and ZetaPlus®, Holtsville, N.Y., USA). Each value reported is the average of 10 measurements.

Sugar analysis of both the raw extract and supernatants of the PEO treated extract samples was performed by 1H NMR Spectroscopy using a method described by Kimle et al (2004). Klason lignin and acid soluble lignin were determined by standard TAPPI methods T222 om −88 and UM 250 respectively. A UV-VIS spectrophotometer (Shimadzu UV 3600) was used to measure absorbance of the solutions at 205 nm from which the soluble lignin fraction was calculated.

1H NMR analysis was used to determine the cellulose and hemicellulose concentration (from the quantification of monomeric sugars obtained from the hydrolysis of glucan, xylan, mannan, arabinan, rhamnan and galactan). The NMR methods used in this research were described in detail earlier [40]. The samples were first hydrolyzed to yield sugars and then analyzed using 1H NMR. In a first stage, the sample is dispersed in 16 ml of 72% sulfuric acid at room temperature for 2 hours, stirring it every 15 minutes to ensure proper dissolution. In a second stage, 21 ml of DI water are added to the mixture, bringing the acid content down to 40%. This mixture is then placed in a water bath at 80° C. for one hour, being shaken every 15 minutes. The tubes are then cooled down and kept in the refrigerator overnight, for the residual solid matter to precipitate. When necessary the tubes are centrifuged at 2500 rpm for 7 min to further settle the solid matter and allow the collection of 1 ml of the clean supernatant, which is transferred to a NMR tube and mixed with 0.1 ml of a standard solution. The standard solution is a mixture of known amounts of tri-methylamine hydrochloride (TMA) and glucosamine. This analysis was done in duplicate.

Polyelectrolytes:

The polyelectrolytes used for this study are alum, PEI, pDADMAC, and CPAM. Different concentrations of these polymers were added to the hydrolyzates for the study of flocculation kinetics. The concentrations of polymers were alum (0.01M, 0.1M, 0.25M), PEI (25 ppm and 50 ppm, or 0.5% and 1% v/v), pDADMAC (23.6 ppm and 47 ppm; weight of polymer per weight of extract), CPAM (Medium Molecular weight: 10 ppm, 15 ppm, 20 ppm and 25 ppm), CPAM (Higher molecular weight; 20 ppm and 30 ppm) and a combination of alum and PEI (0.15 M+25 ppm/0.5% v/v) was also used for the study.

Polyethylene Oxide

Laboratory grade Polyethyleneoxide (PEO) with molecular weight in excess of 1,000,000 Daltons from Alfa Aesar (Ward Hill, Mass.) was used. The PEO solution was prepared as 1 g/L in filtered reverse osmosis water. The solution was prepared the day before use and was kept at a temperature lower than 10° C. until it was used. Besides the concentration of polymer, effect of wood extract pH on flocculation was also examined. The pH of wood extract was varied from 2 to 8.5 with dilute $H_2SO_4$ and NaOH solutions respectively.

Total Lignin Analysis:

Klason (or Acid Insoluble) Lignin and Acid Soluble Lignin tests were performed, according to the respective TAPPI Standard T222 and TAPPI Useful Method 250. In case of the acid insoluble lignin, the standard was slightly modified since the all the reagent amounts were cut in half. For the acid soluble lignin, Klason lignin was performed in duplicates. Acid Soluble lignin was performed in triplicate.

Acid insoluble lignin was determined following the Tappi T 222 om-06 method, using 4 ml of 72% $H_2SO_4$ and 50 ml of water on 100 ml of extract and boiling for four hours at 1000 C, with frequent addition of water. The sample was then filtered in a sintered glass crucible using Whatman filter paper 4 (ash-less), the precipitate was collected as insoluble part while the supernatant was used for the determination of acid soluble lignin. A PerkinElmer Lambda 650 UV/Vis Spectrophotometer (Shimadzu UV 3600) was used to measure absorbance of the solutions at 205 nm from which the soluble lignin fraction was calculated considering absorptivity to be 110 L/g/cm.

Flocculation Experiments 100 ml of neat wood extract was taken in a glass beaker and flocculating agent was added and the mixture was agitated with magnetic stirrer. A 5 ml of sample mixture was collected to measure the particle size and zeta potential during process of mixing. Next the agitated mixture was processed for sedimentation in a 100 ml graduated glass cylinder in a fixed position without any disturbance and turbidity of supernatant was measured for about 1-2 hour time period. Turbidity, particle size and zeta potential of the neat extract were measured initially for the reference. Besides the concentration of polymers, effect of wood extract pH on flocculation was also studied. The pH of wood extract was varied from 3.5 to 6.1 and 8.0 with diluted NaOH solution. The study was performed for various concentrations of alum, PEI, CPAM and pDADMAC.

Pilot Study

Flocculation and clarification with PEO were demonstrated on batches of 1000 kg of extract with optimal polymer dosage of 50 ppm PEO at 25° C. temperature conditions. Further, the flocculated extract was mixed with commercially available soft wood pulp which acted as a filter aid to adsorb flocculated particles and suspended mixture was filtered through a 5 micron pore size filter cloth. The filtrate showed a 99.5% reduction in turbidity, from 12000 NTUs in the raw extract to 50 NTUs in the filtrate.

The average particle size of colloidal particles in neat sugar maple wood hydrolyzate were around 260-290 nm and pH of the solution was 3.5. The zeta potentials of dispersed particles in extracts are between −18.6 to −21.0 mV which showed that the particles are strongly anionic. The presence of negatively charged particles indicates that separation of these particles could be possible by flocculation with cationic polymers followed by sedimentation. The flocculation kinetics depends on several factors such as mixing conditions, adsorption on particles and concentration of polymers. The charge density and molecular weights of cationic polymers play an important role in coagulation of negatively charged particles.

Figure 1:
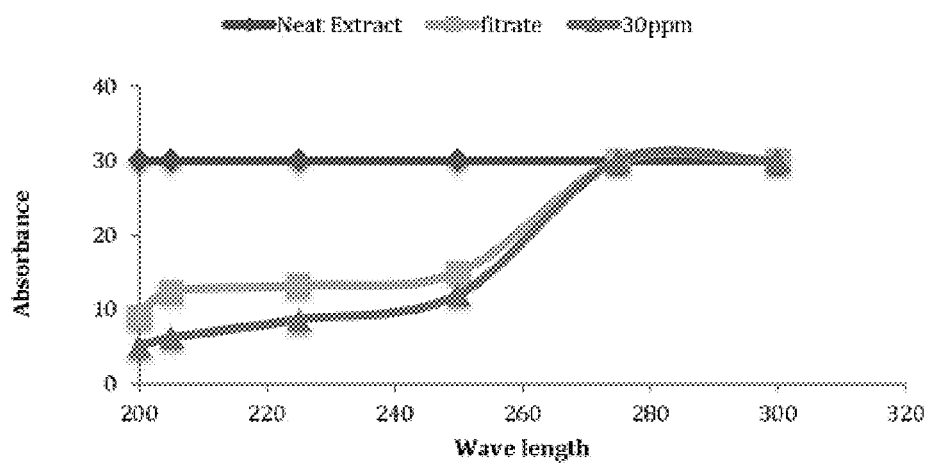
FIG. 1 shows UV absorption spectra of supernatants of hydrolyzates treated with CPAM (30 ppm), filtrate from 0.2 μm filter (arbitrary units)

The flocculation kinetics depends on several factors such as concentration of polymer, pH of the solution and temperature. The rate of sedimentation of the flocculated particles was measured by turbidity of supernatants of the solution and height of the sediment volume as a function of time. The aggregation of the particles was observed in the agitation process within few seconds upon addition of the polymer to the extract. FIG. 1 shows the height of the sediment volume at different concentrations of the polymer. The height of the sediment volume is not altered between the polymer concentrations of 20 ppm to 40 ppm. The temperature of the extract was maintained constant at 25 C.

A further demonstration was conducted with about 160 liters of extract, and the polyethylene oxide flocculant flocculated the entire batch within about 2-5 min. The suspension was filtered with a simple bag filter, and the resulting hydrolyzate was clear. A screen filter is generally usable as an alternate filter. The anticipated yield is >99%, based on the fact that about 100 g to 200 g of solids were filtered out of nearly 6 kg of solids in suspension.

By using a simple separation system, a plate and frame filter press can be eliminated, which is expensive, requiring manpower and maintenance. Flocculation can also sequester lignin for further use in products. The polymer binds with lignin to yield a good, extrudable material that can be either pelletized for fuel or spun into fibers; therefore, the flocculant forms a functional part of the final product, and need not be separated for these purposes. Flocculation can eliminate components which have adverse effects on fermentation downstream. For example, reduction in acetic acid may be achieved.

The preferred polymer for use in the flocculant is Polyethylene Oxide, of MW over 1000 kDa (Alfa Aesar, Ward Hill, Mass.). A "polymer makedown" system is available from Ashland. See, e.g., U.S. Pat. Nos. 6,384,109; 8,038, 846; 8,021,516; 7,648,032; 7,531,600; 7,514,007; 7,476, 272; 7,442,722; 7,258,732; 7,001,953; 6,939,443; 6,831, 042; 6,642,351; 6,417,268; 6,414,080; 6,372,088; 6,074, 473; 6,071,379; 6,020,422; 5,707,533; 5,696,194; 5,688, 315; 5,667,885; 5,614,602; 5,603,411; 5,584,394; 5,565, 509; 5,344,619; 5,328,880; 5,312,484; and 5,130,395, each of which is expressly incorporated herein by reference.

Polyelectrolytes

The kinetics of flocculation depends most often on charge neutralization, and rate of adsorption (initial attachment) of polymer chains to the surface. The charge density and molecular weights of cationic polymers play important roles in the coagulation of negative colloidal particles. For oppositely charged polymers and particles, two main mechanisms can be involved in the particle flocculation i.e., charge neutralization and bridging flocculation. [9]. Low molecular weight and high charge density polymers such as polyethyleneimine (PEI), poly-diallyldimethyl ammonium chloride (pDADMAC) are cationic polymers which are widely used for separation of colloidal particles. These polymers are often involved in aggregating the particles by charge neutralization and patch flocculation mechanisms.

Cationic polyelectrolytes are subject to change in charge and size in solution upon alteration of pH and ionic strength. Furthermore, the absorbability of the polyelectrolytes on an oppositely charged surface may change with these solution properties. Since these polymers are polybase, addition of protons (reduction in pH) will result in protonation and subsequent expansion of polyions due to mutual charge repulsion. [8, 10]

Flocculation efficiency and effectiveness is often determined by measuring the changes in turbidity, particle size and the settling behavior of the extracts in the hot water process. In addition, because of the nature of neutralization involved, the effect of changing extract pH, dosage of flocculants and the influence of electrolytes is often a factor in determination of flocculation efficiency.

Figure 2:
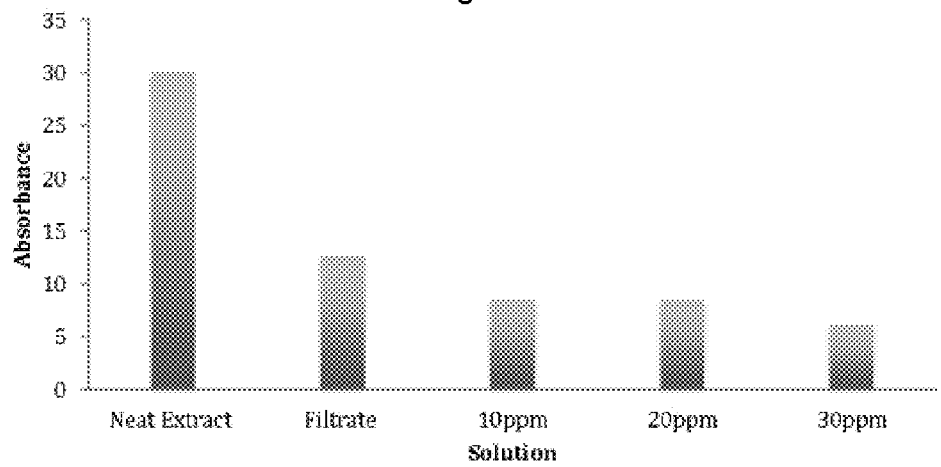
FIG. 2 shows UV absorption spectra at 205 nm of supernatants of hydrolyzates treated with CPAM at different concentrations in ppm.

Table 1 shows the characteristics of the hydrolyzate suspension used in this work. The zeta potentials of dispersed particles were between −18.6 to −21.0 mV. Since they are negatively charged, separation of these particles should be possible by flocculation with cationic polymers followed by sedimentation. The impact of cationic polyacrylamide on flocculation was investigated in neat hydrolyzates by measuring the UV absorbance spectrum. FIG. 1 shows the spectrum for three solutions: the neat hydrolyzate (diluted 100×), the supernatant after treatment with CPAM and a filtrate from filtering the neat hydrolyzate without polymer addition. The neat extract had high absorption in the 200-300 nm region whereas the resulting solutions after adding the CPAM lowered the absorbance to under 10. The absorbance of the supernatant was similar to that of the filtrate and the CPAM treated hydrolyzates. FIG. 2 shows the absorbance at different levels of CPAM addition. It appears that the absorbance is a minimum at 30 ppm indicating the best removal of the fraction of the hydrolyzate responsible for UV absorption. These are most likely to be the lignin related compounds in colloidal and dissolved forms. This was confirmed by analyzing the compositions of the supernatants as described later.

TABLE 2

Characteristics of hydrolysate suspension.

| | |
|---|---|
| Average particle sizes range | 280-320 nm |
| Zeta Potential | −18.6 to −21.0 mV |
| pH | 3.5-3.6 |
| Turbidity | 880-990 NTU's (10 folds Dilution) |

Figure 3A:
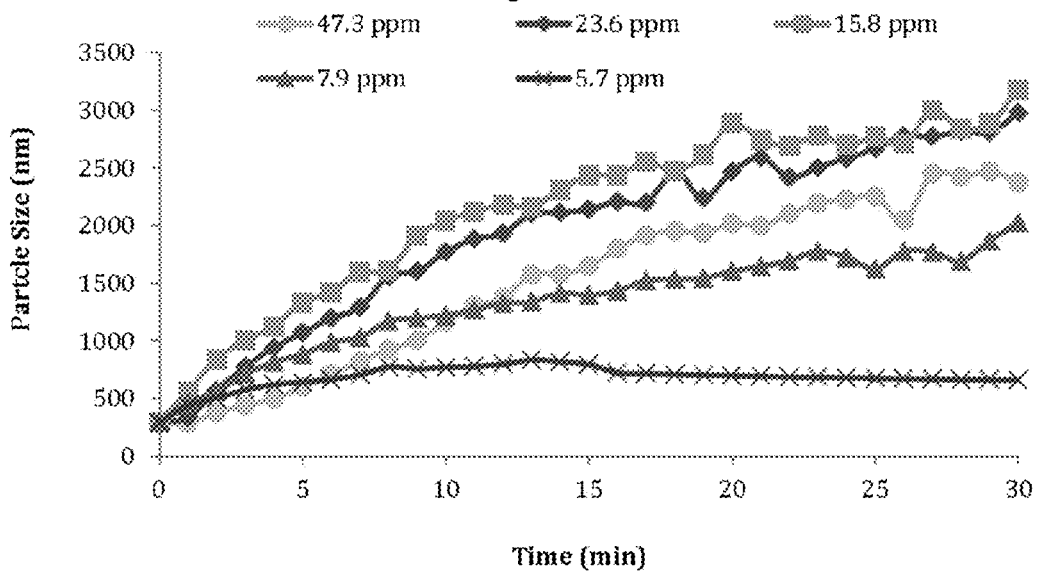
FIGS. 3A-3D show graphs of particle size for aggregations over time for pDADMAC (FIG. 3A), Alum (FIG. 3B), PEI (FIG. 3C), and CPAM (FIG. 3D)
Figure 3B:
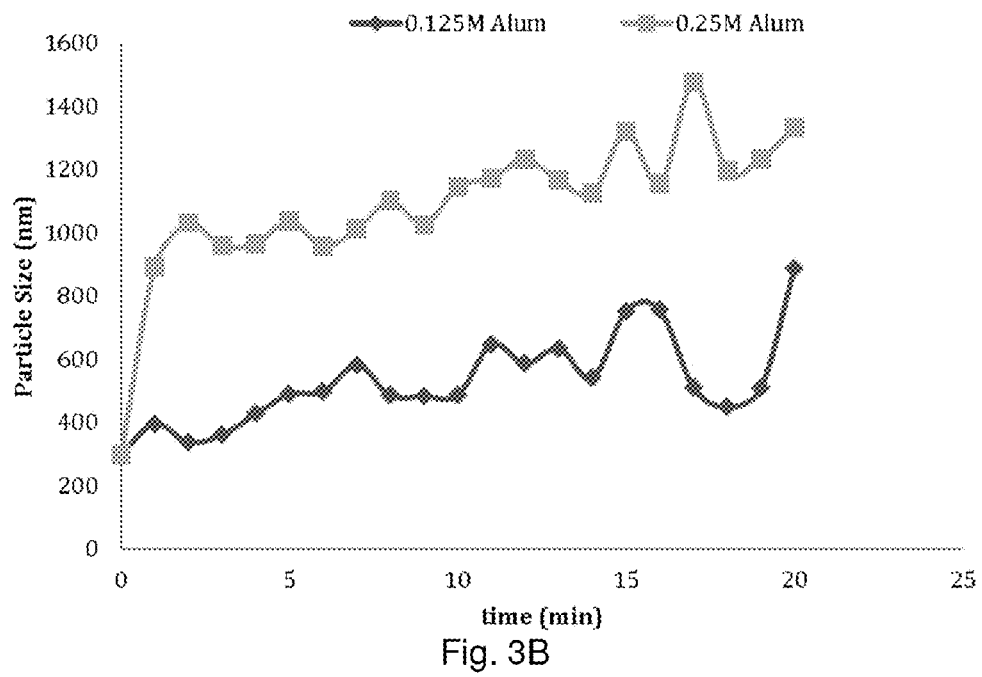
Figure 3C:
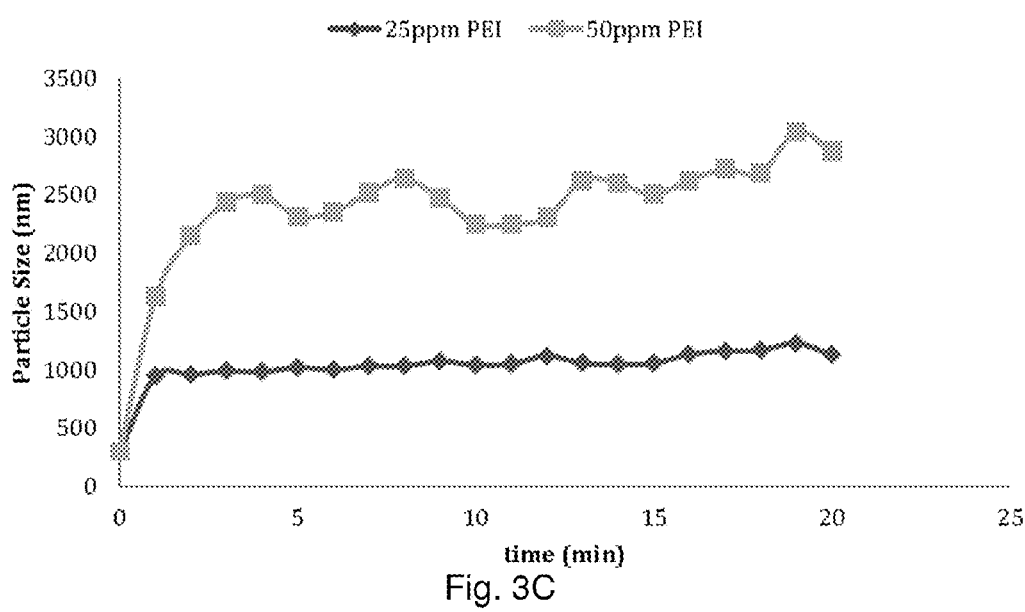

The performance of each of the polymers was investigated with respect to the development of the size of the flocs, their effect on the turbidity and settling velocity of the suspension and on the final sediment volumes. FIG. 3A shows the aggregation achieved by pDADMAC based on results obtained earlier [15]. pDADMAC also reduced the turbidity of the hydrolyzates from initial values above 9000 NTUs to less than 40 NTUs (at different addition levels). Note that optimal growth and floc size was obtained at addition levels of ~15.8 ppm. The aggregation effect of alum, PEI and CPAM at their optimal dosages are shown FIGS. 3B-3D. The samples of PEI and CPAM treated extracts were diluted 10× and the alum treated samples were diluted by 2×. At 10 folds dilution, the alum was not effective at flocculation. FIG. 3B shows the rapid growth of the flocs when sufficient quantity of alum was added (~0.25 M). It appears that flocculation is much faster than with pDADMAC although the floc sizes are smaller. The cationic electrolyte PEI acts similar to alum at dosage of 50 ppm. The flocs are much larger than those obtained by alum although the kinetics are comparable. Higher dosages were found to reduce the floc sizes and ultimately suppress flocculation altogether indicating that the particle surfaces have been overcharged to become cationic. The application of cationic polyacrylamide results in a rapid flocculation of the dispersions even at the relatively low dosages of 5 ppm. At higher dosages, flocculation was impeded and the suspension was stabilized, possibly by steric repulsion between the particles. Based on the rate of observed aggregation, pDADMAC appears to be the slowest, perhaps because its MW is the lowest among the polymers considered here. The dynamic zeta potential variations in FIGS. 3A-3E show that the adsorption phase is relatively fast (of the order of a few minutes or less) for all the polymers considered here. Therefore, adsorption kinetics cannot be the significant cause of the differences in the rates of aggregation. Since a number of factors, including the magnitude of the interparticle interaction forces determine the kinetics of aggregation, models similar to those proposed earlier for charge neutralization [45] and bridging polymers [46] need to be developed.

Figure 4A:
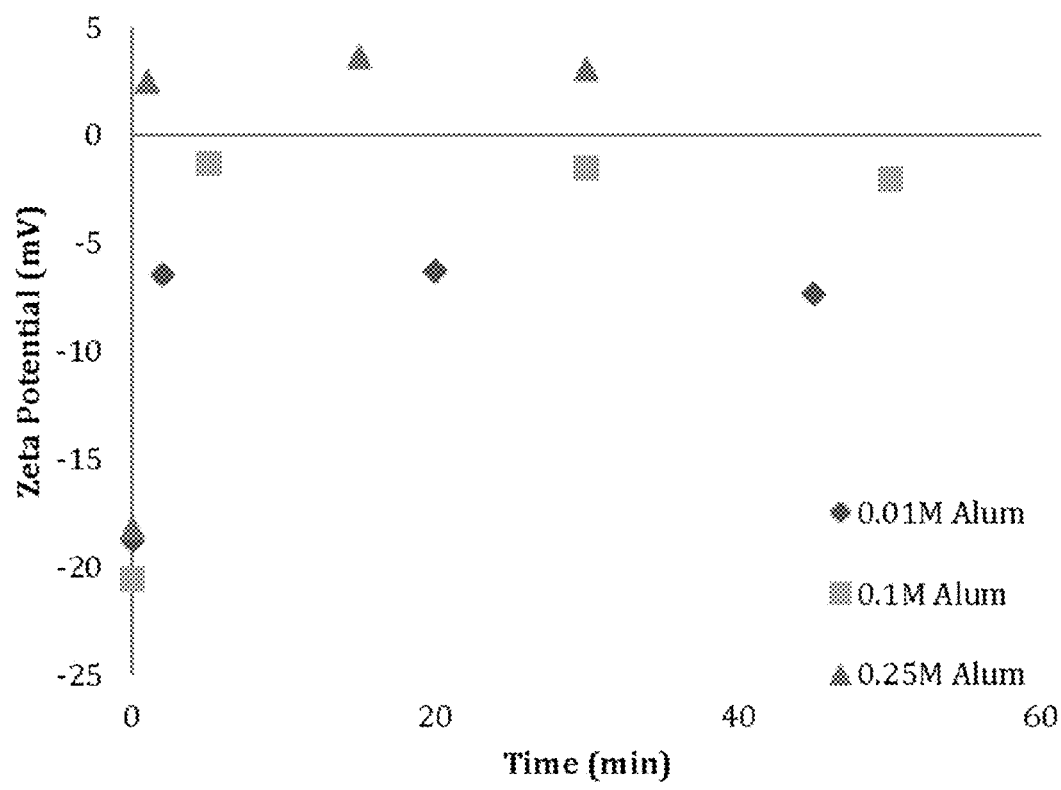
FIGS. 4A-4E show graphs of zeta potential over time for Alum (FIG. 4A), PEI (FIG. 4B), pDADMAC (FIG. 4C), med. mol. wt. CPAM (FIG. 4D); and 25 ppm CPAM+0.15 M Alum.
Figure 4B:
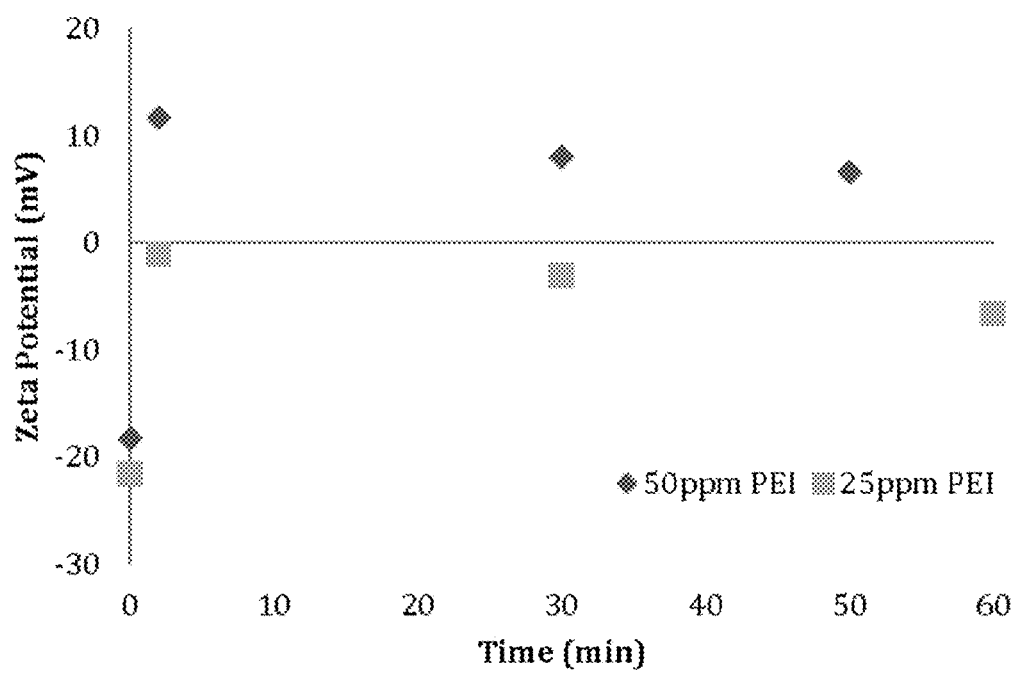
Figure 4C:
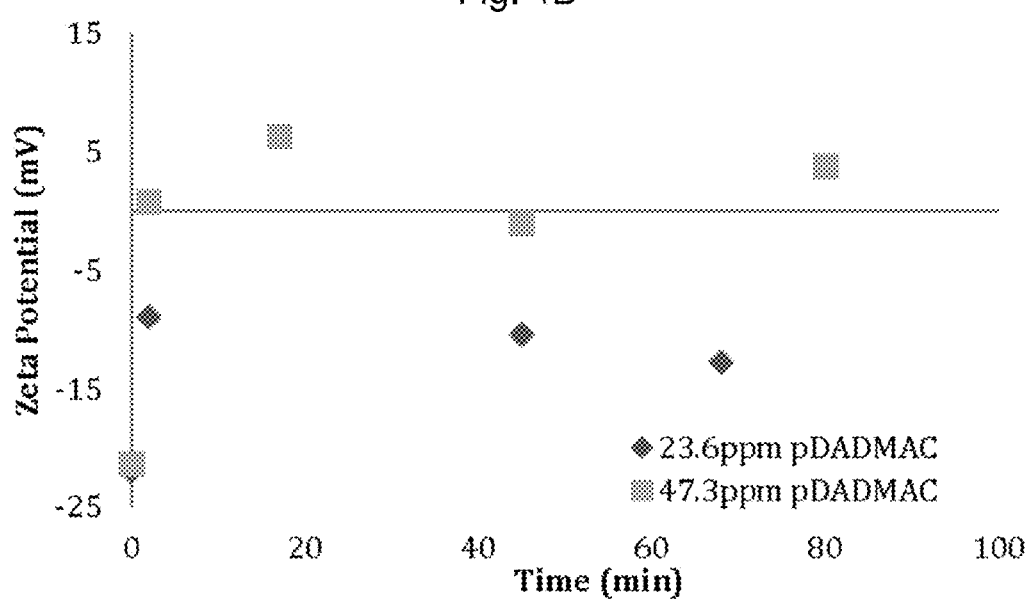
Figure 4D:
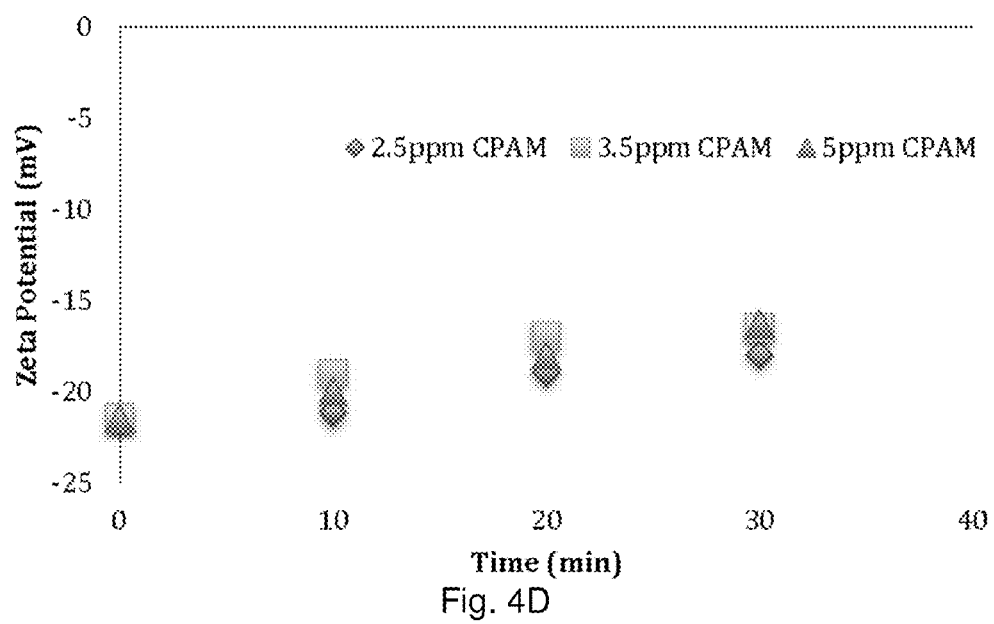
Figure 4E:
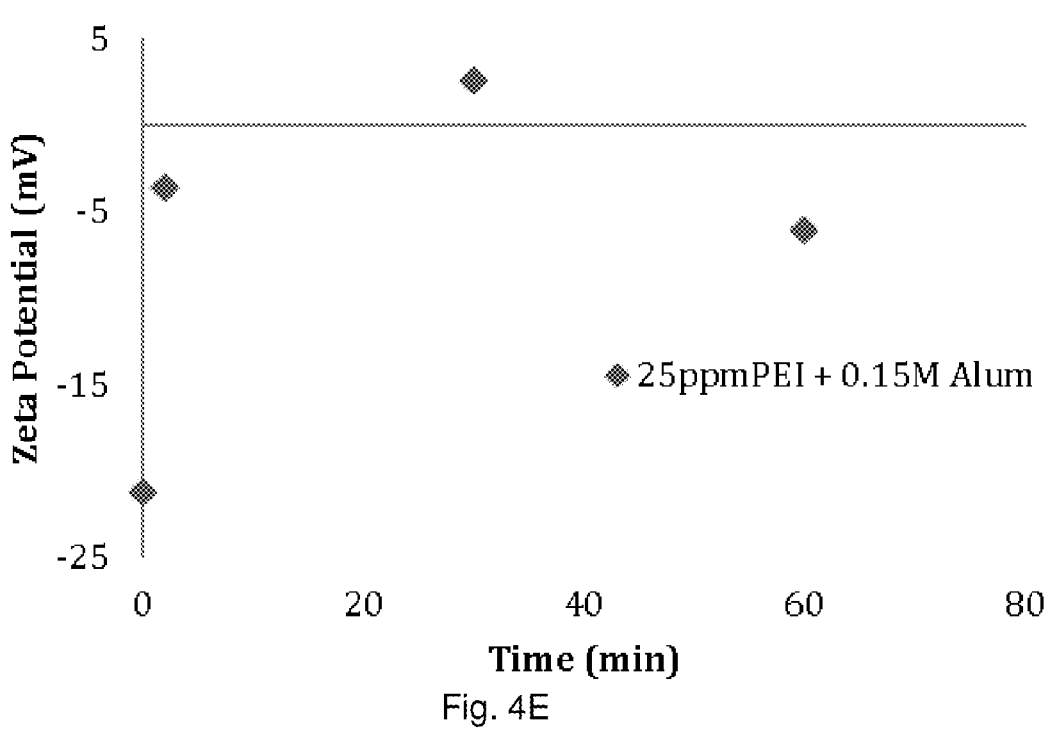

The zeta potential of the particles was measured as function of time for each polymer at optimal dosage levels and is shown in FIGS. 4A-4E. When alum was added, the pH of the solution decreased from 3.5 to 3.2. The other solutions did not show changes in pH upon addition of the polyelectrolytes. In this range of pH, alum is expected to yield the trivalent Al cation, which would be available for adsorption onto the anionic particle surfaces [41]. The zeta potential of the hydrolyzates was approximately −20 mV in the absence of the flocculants. As shown in FIG. 4A, it approaches zero as alum concentration is increased. At a dosage of 0.1 M, the zeta potential vanishes, indicating the isoelectric point for the suspension. Similarly, increasing the concentration of the polymers (PEI and DADMAC) leads to lower zeta potentials of the suspensions. However, at higher polymer dosages, the zeta potential becomes positive, indicating charge reversal of the particles to show a net cationic charge. The suspensions are restabilized at this point and the turbidities were observed to be close to the initial values. The PEI dosage at which the zeta potential vanishes is between 25 ppm and 50 ppm, whereas for DADMAC it is between 23.6 and 47.3 ppm. When a combination of PEI and alum was used (FIG. 4E) the polymer dosage at vanishing zeta potential was lower at 25 ppm. The addition of alum reduces the net surface charge available for the PEI and therefore a smaller dosage is necessary to cause flocculation. A decreasing trend in the zeta potential is observed with time in these figures (with the exception of the CPAM case). Redistribution of the adsorbed cationic species, perhaps by penetration into the particles or change of the conformation of the polymers on the surfaces could lower their effectiveness at neutralizing surface charges. Both of these effects could account for the slow decrease in the zeta potentials with time. The colloidal particles (of lignin) may be porous, in which case diffusion into the interior of the particles can lead to the observed decay in surface potential. The zeta potentials of the solution did not change with the addition of the CPAM. The CPAM size is expected to be higher than the low MW PEI and pDADMAC, which may hinder its diffusion into the particle interior. The aggregation of the particles was noticed immediately when the polymer CPAM was uniformly mixed with the solution at slow agitation. The dosage of CPAM on a ppm basis necessary for flocculation is much smaller than the lower MW polyelectrolytes or alum.

Figure 5A:
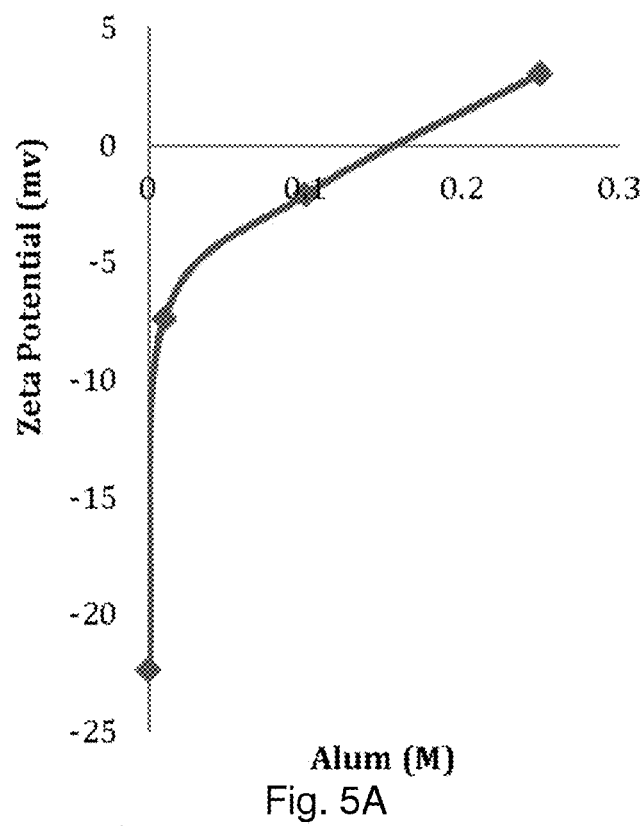
FIGS. 5A-5C show graphs of zeta potential vs. flocculating agent concentration for Alum (FIG. 5A), PEI (FIG. 5B), and pDADMAC (FIG. 5C)
Figure 5B:
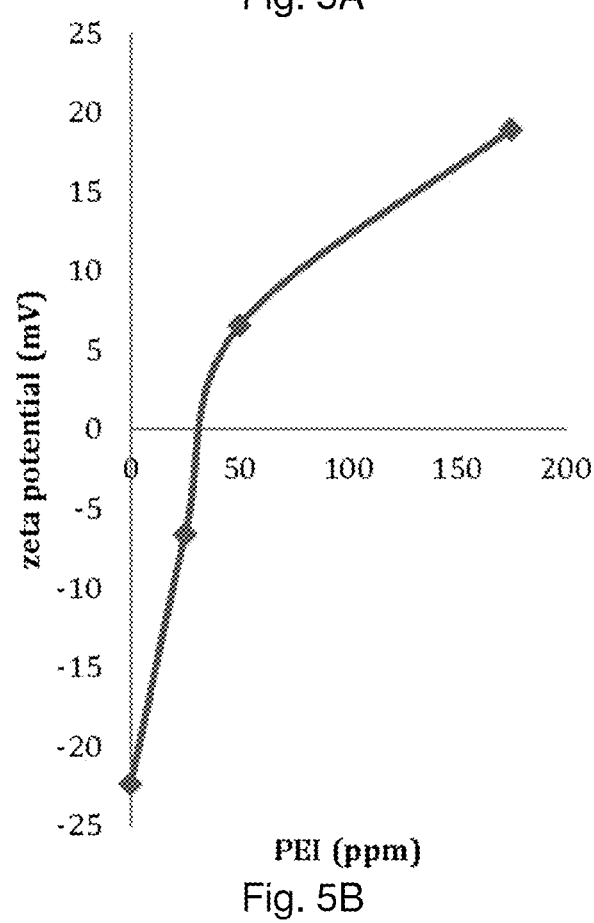
Figure 5C:
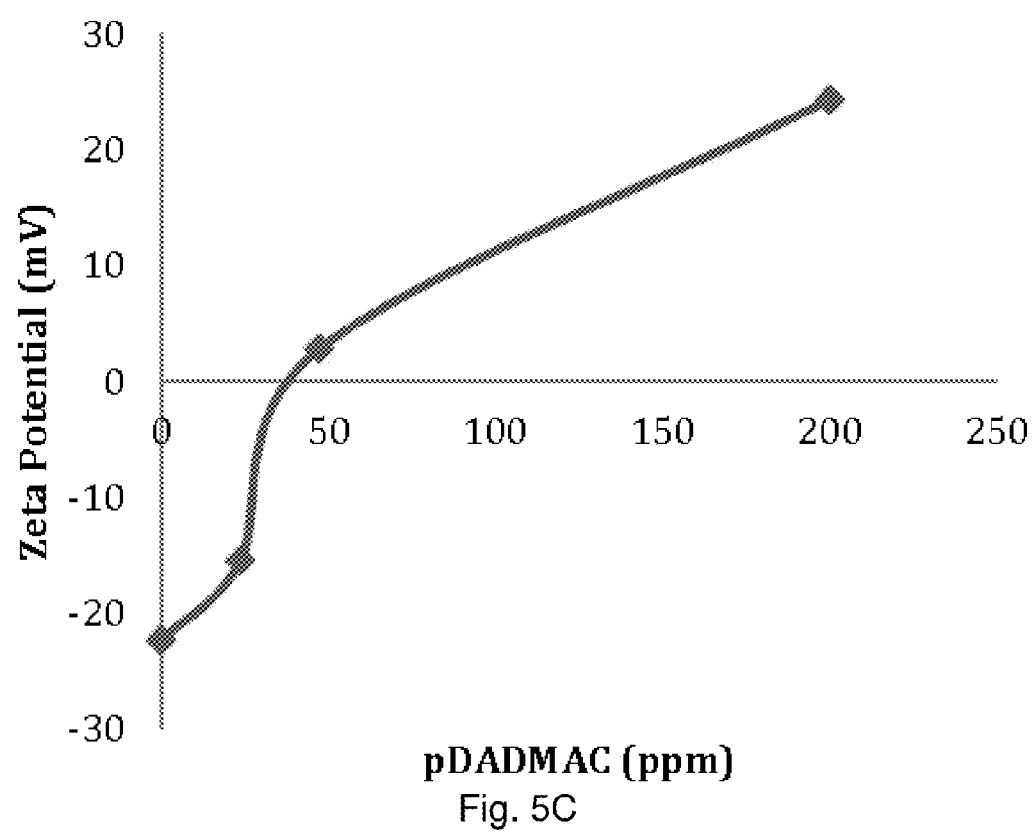
Figure 6A:
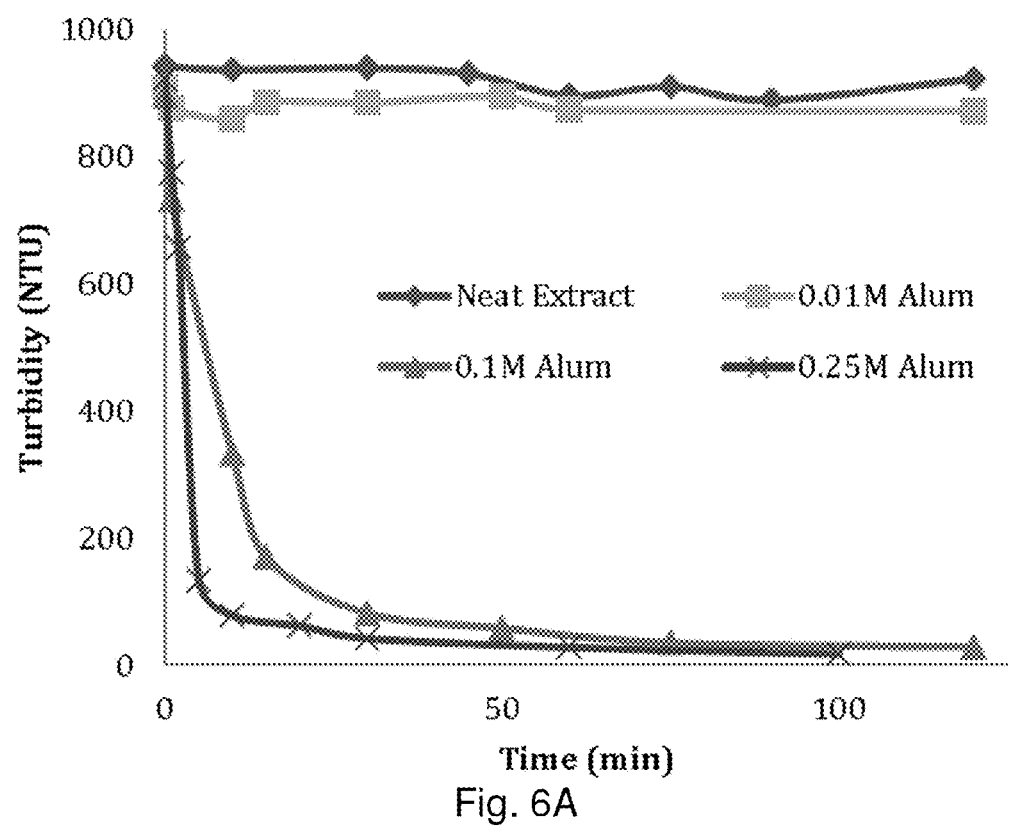
FIG. 6A-6F show graphs of turbidity of supernatant vs. time for different concentrations of polymers (6A), Alum (6B), PEI (6C), pDADMAC (6D), med. mol. wt. CPAM (6E), high. mol. wt. CPAM (6F), and a combination of PEI and Alum (6F)
Figure 6B:
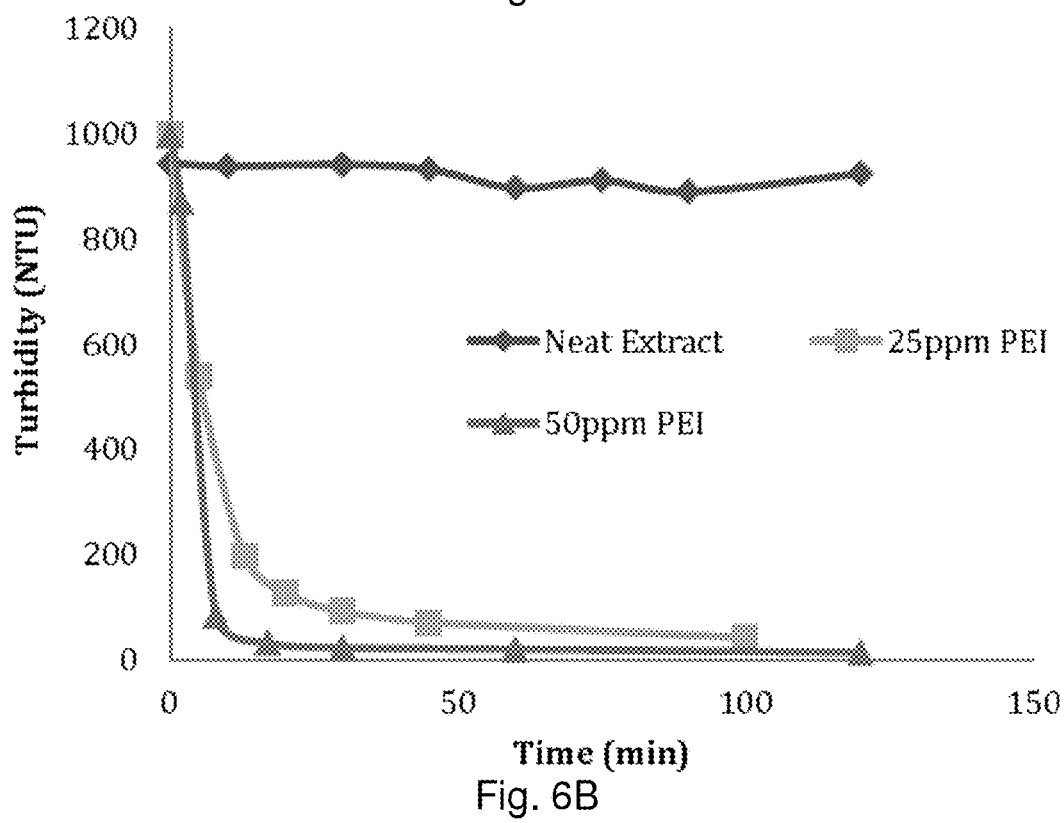
Figure 6C:
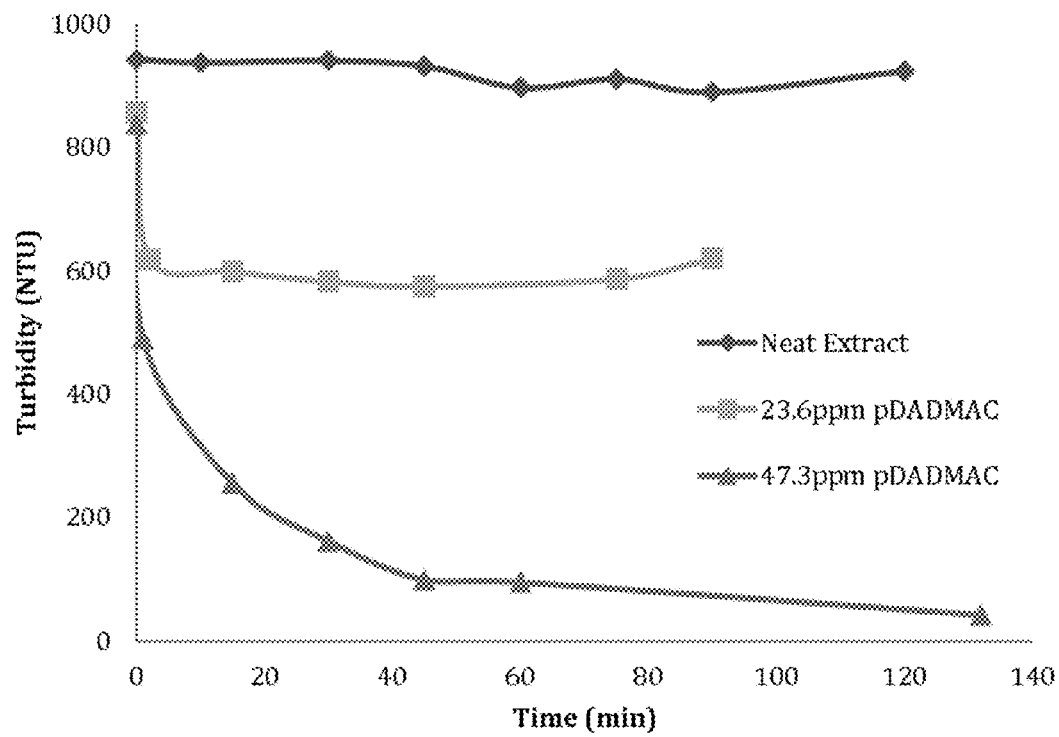
Figure 6D:
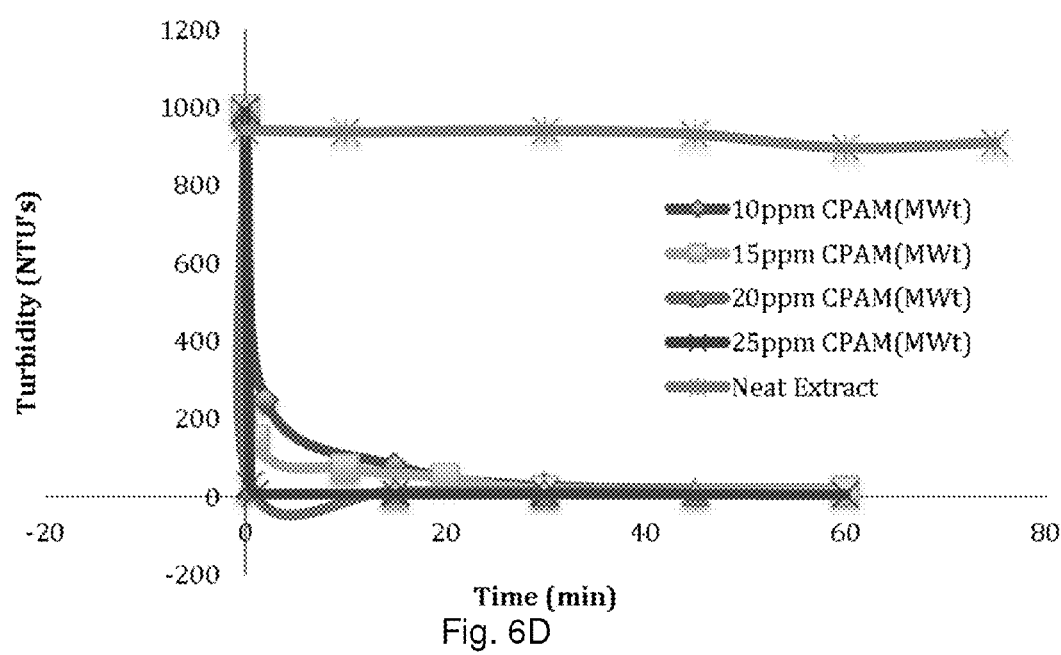
Figure 6E:
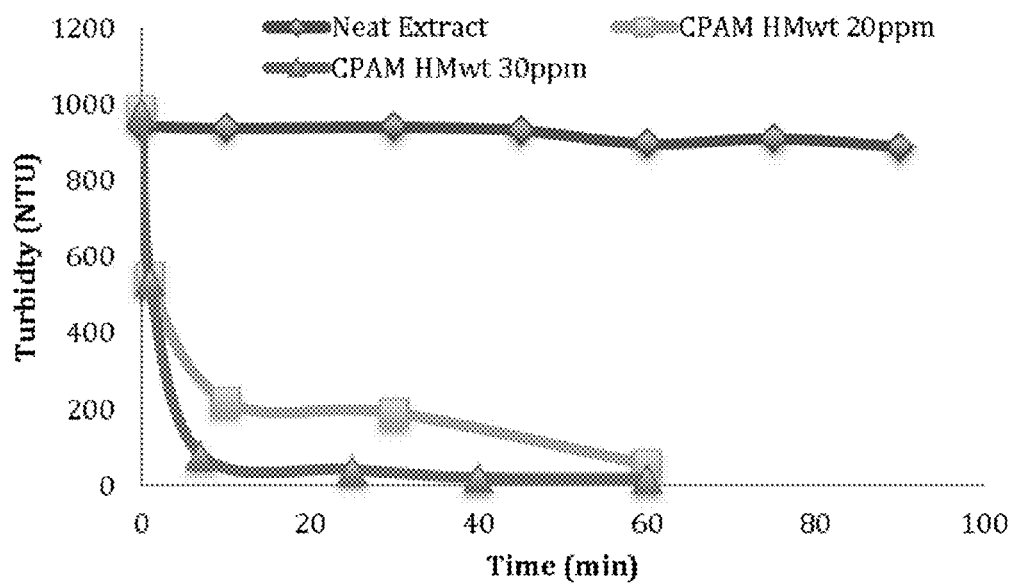
Figure 6F:
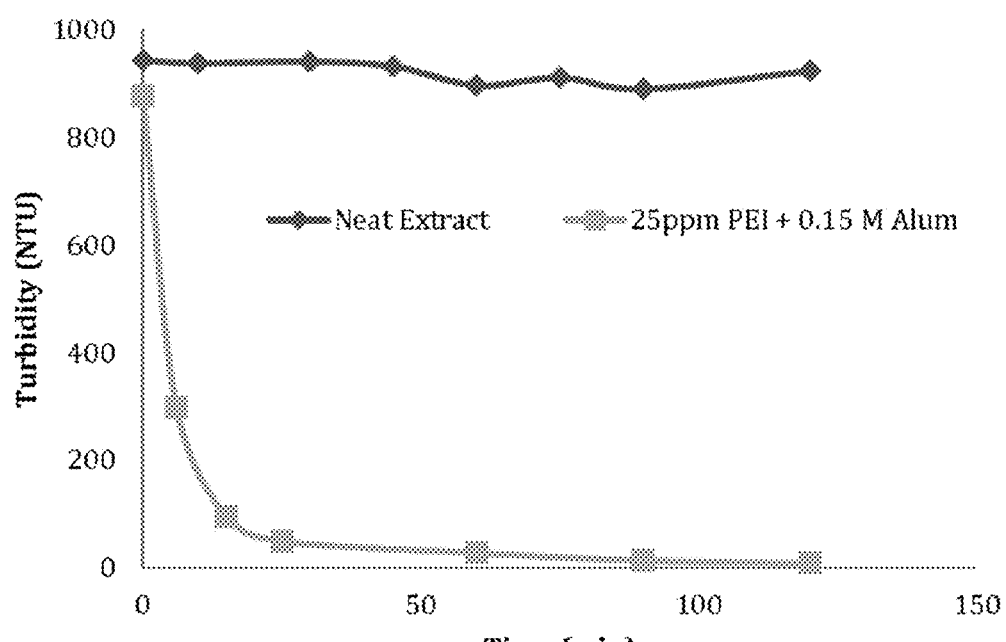
Figure 7A:
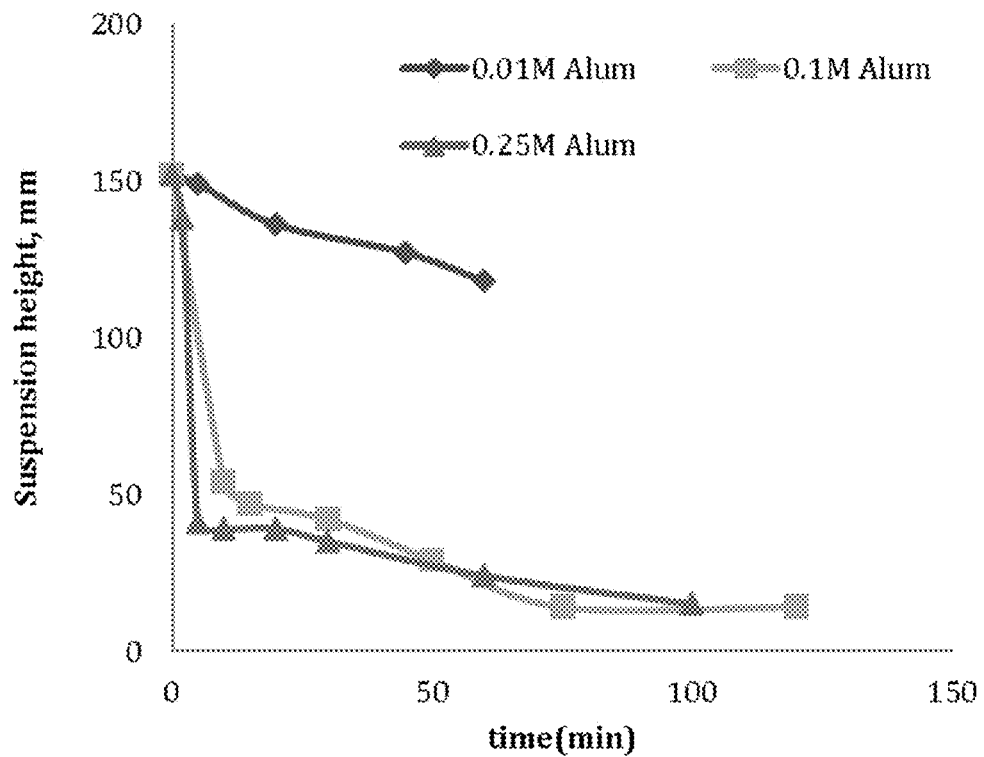
FIGS. 7A-7F show graphs of suspension height vs. time for Alum (FIG. 7A), PEI (FIG. 7B), pDADMAC (FIG. 7C), med. mol. wt. CPAM (FIG. 7D), high. mol. wt. CPAM (FIG. 7E), and PEI+Alum (FIG. 7F)
Figure 7B:
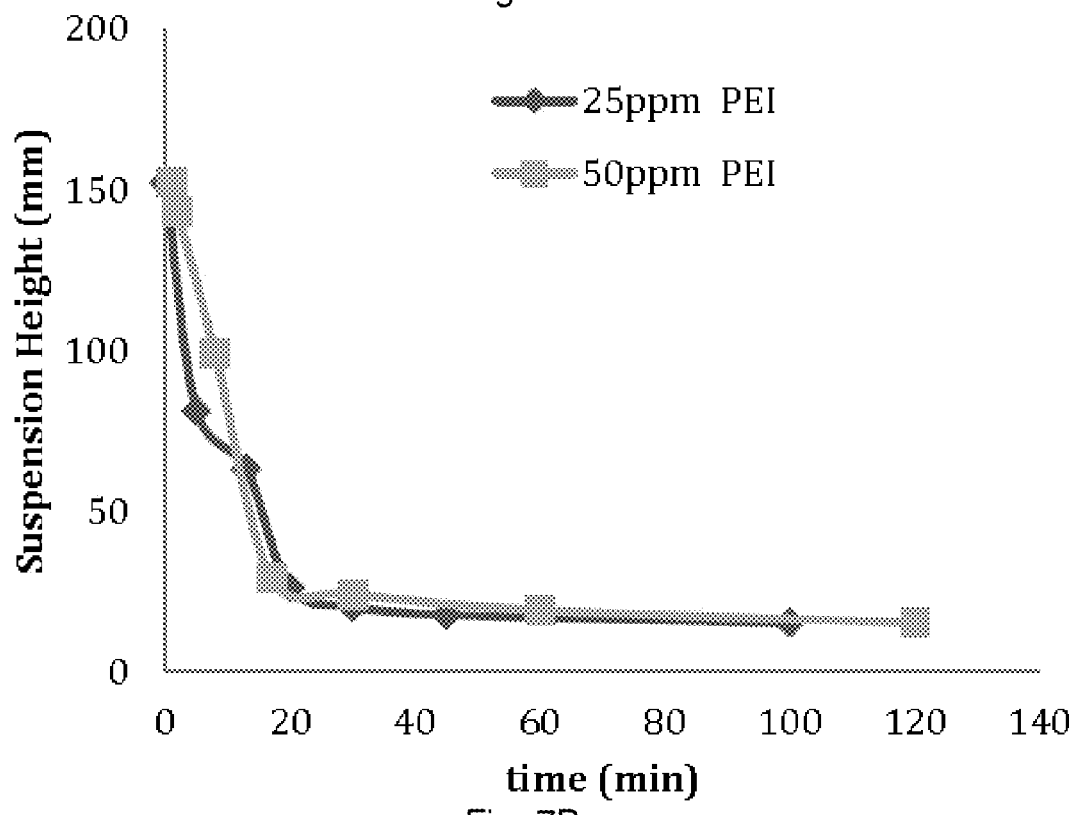
Figure 7C:
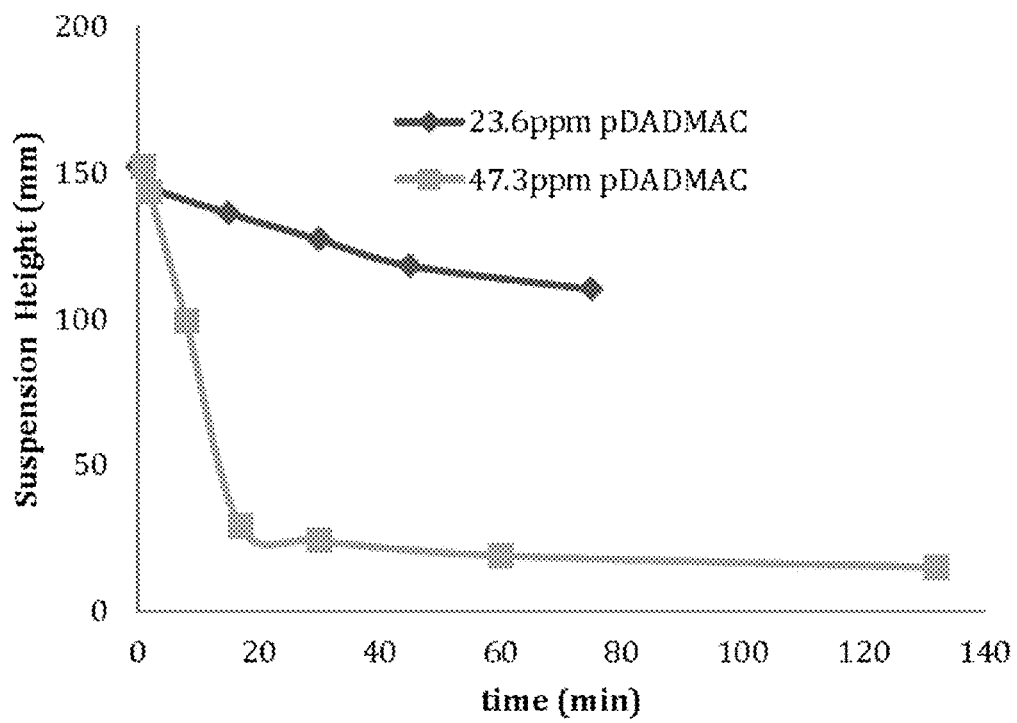
Figure 7D:
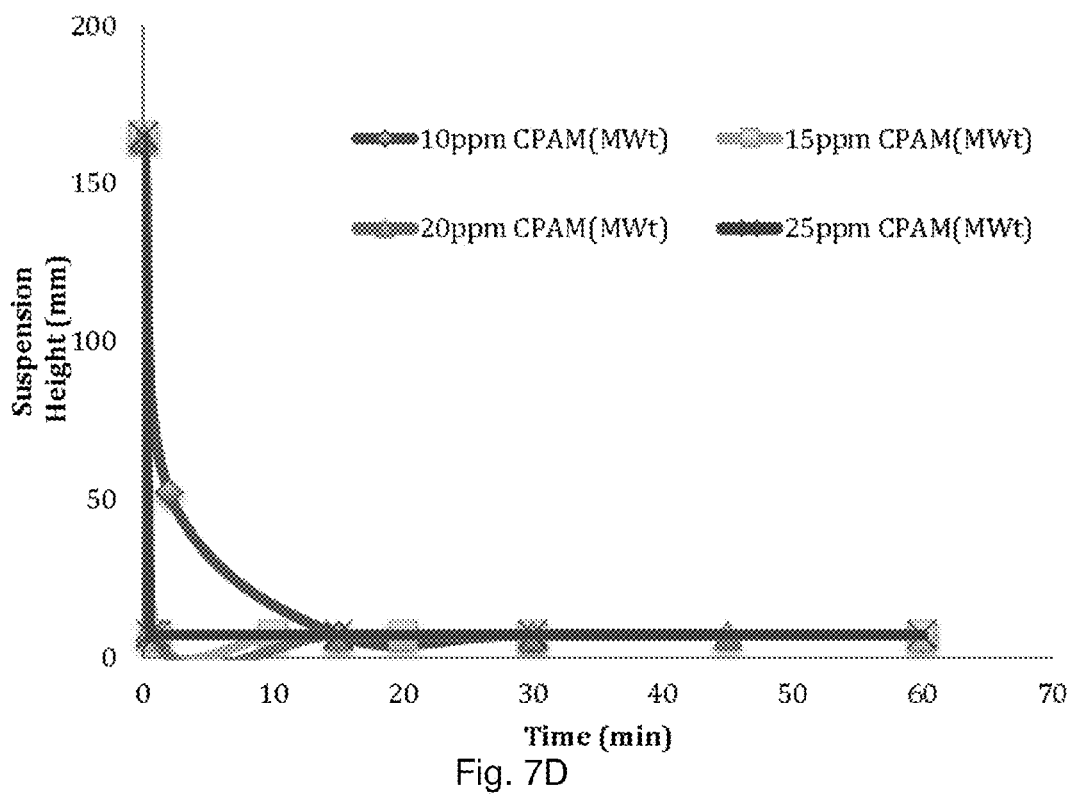
Figure 7E:
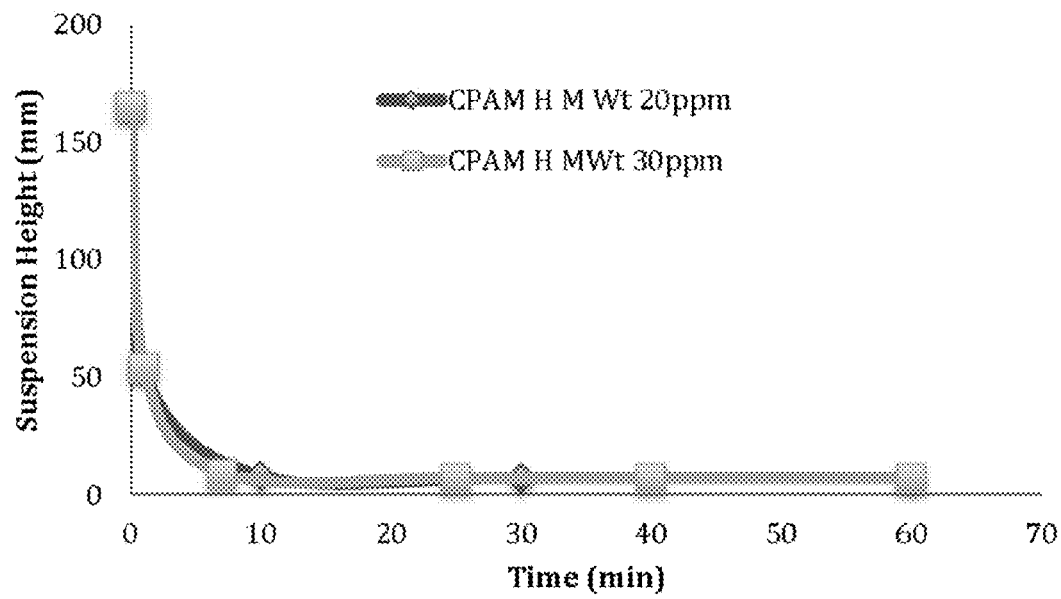
Figure 7F:
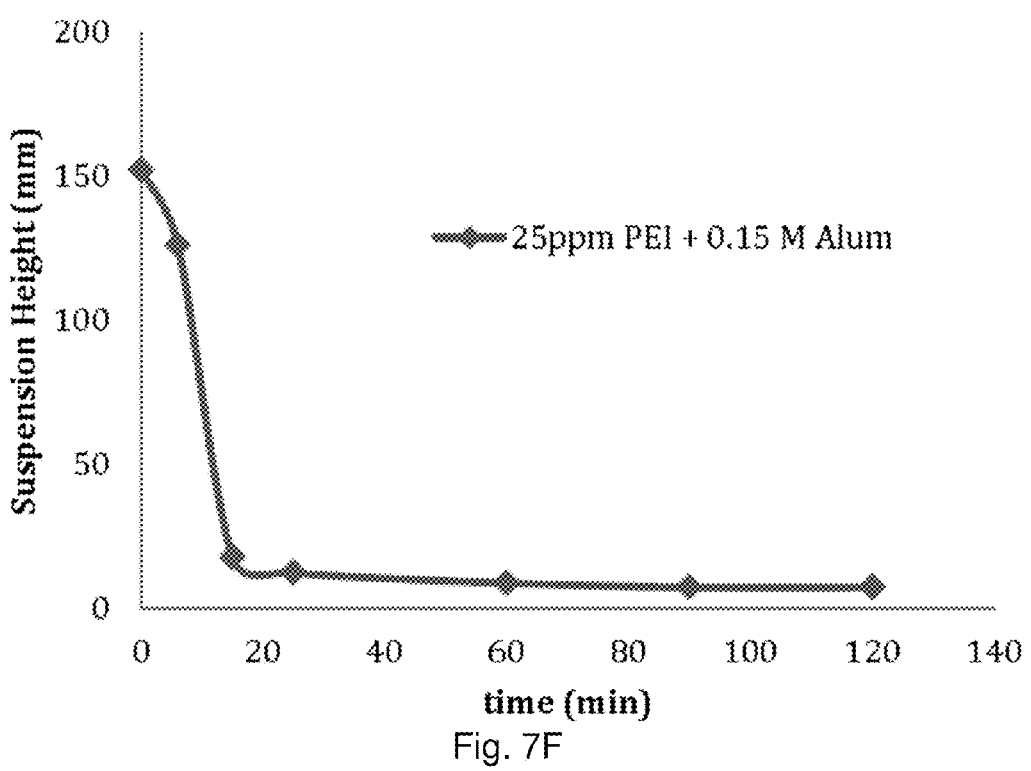
Figure 8A:
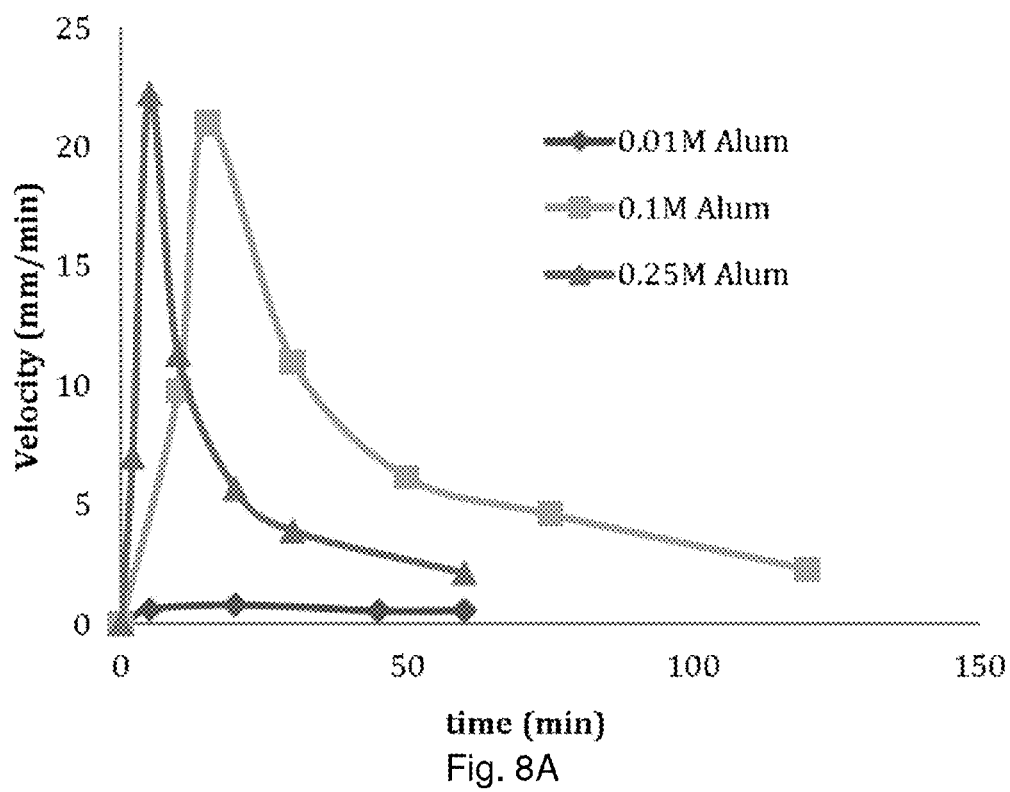
FIGS. 8A-8D show graphs of settling velocity vs. time for Alum (FIG. 8A), PEI (FIG. 8B), pDADMAC (FIG. 8C), and med. mol. wt. CPAM (FIG. 8D)
Figure 8B:
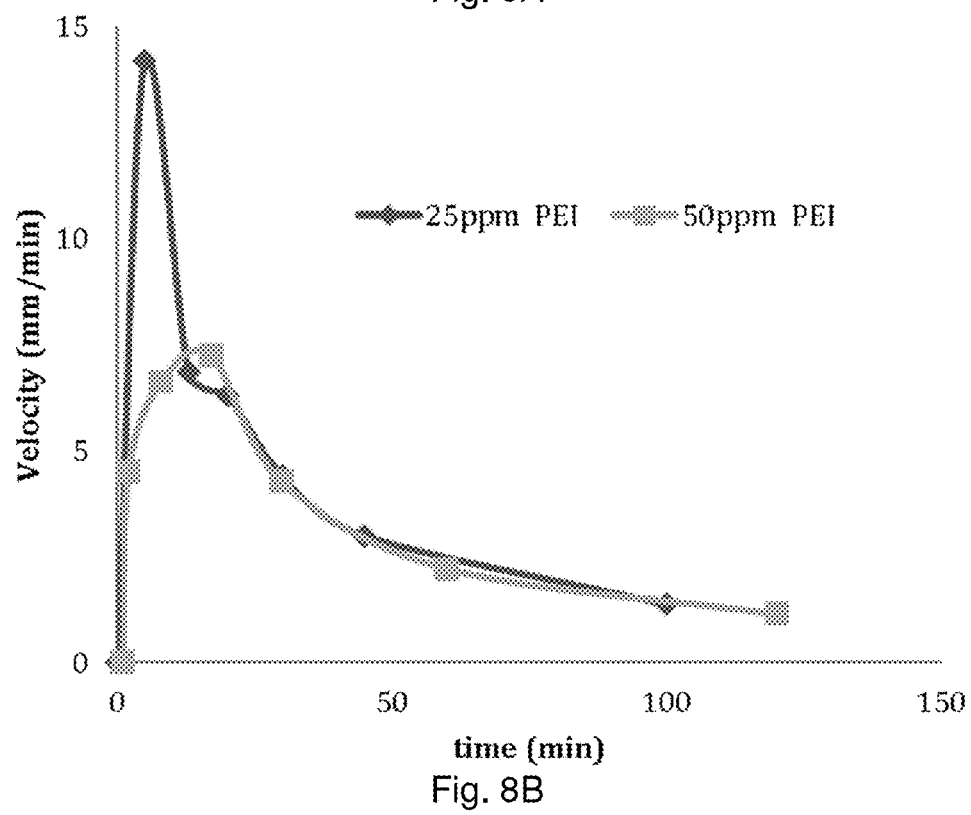
Figure 8C:
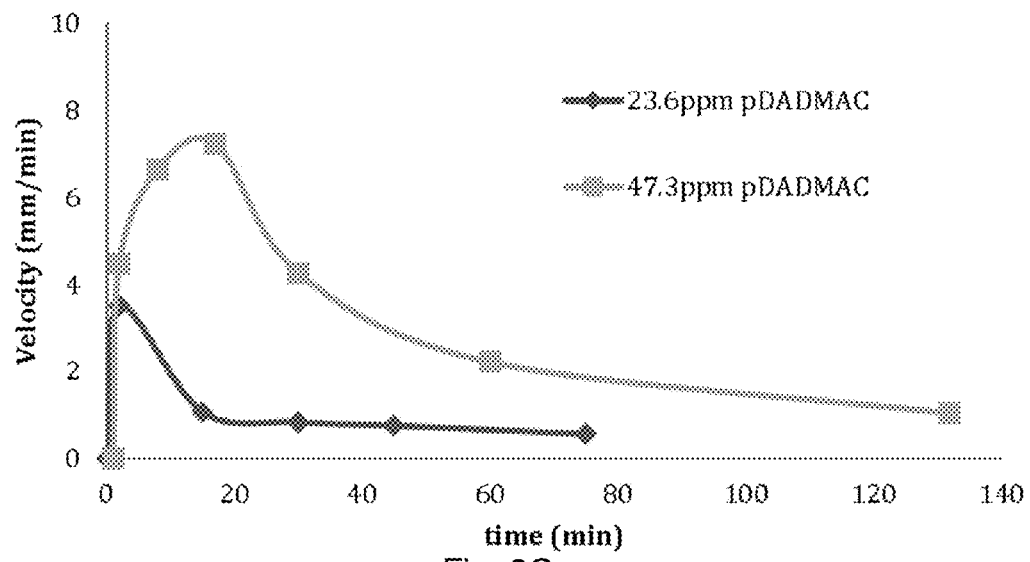
Figure 8D:
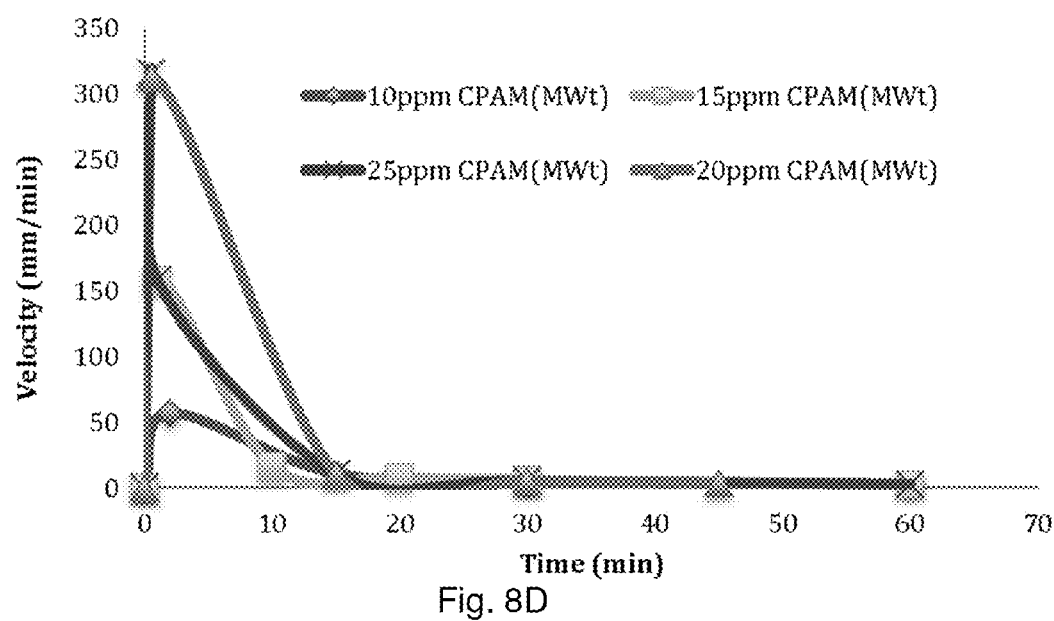
Figure 9A:
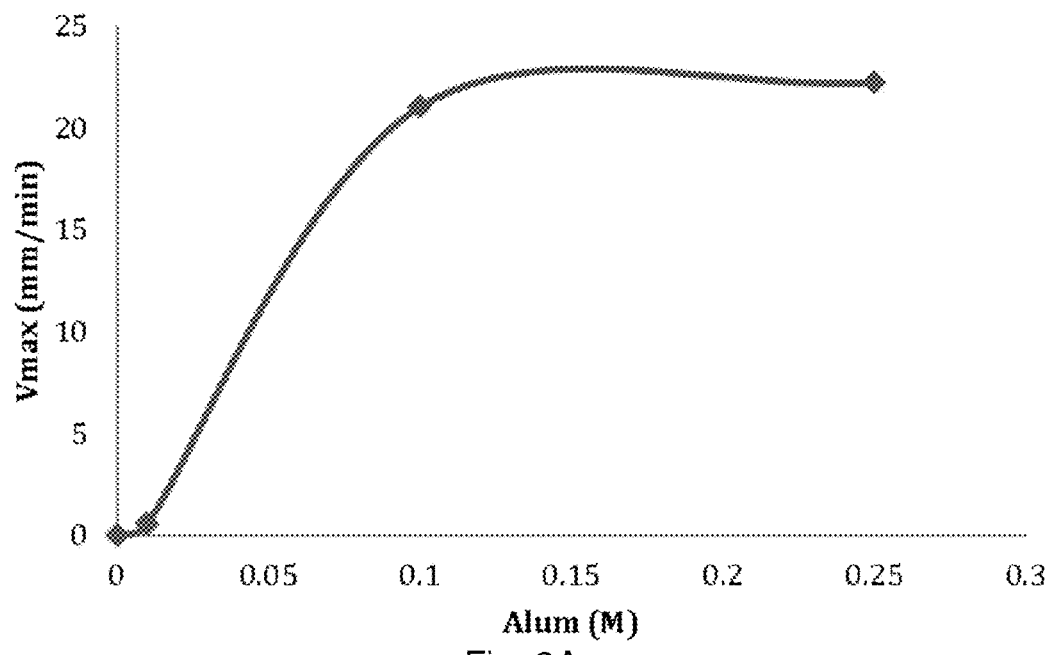
FIGS. 9A-9D show graphs of maximum velocity vs. time for Alum (Alum 9A), PEI (Alum 9B), pDADMAC (Alum 9C), and CPAM (FIG. 9D)
Figure 9B:
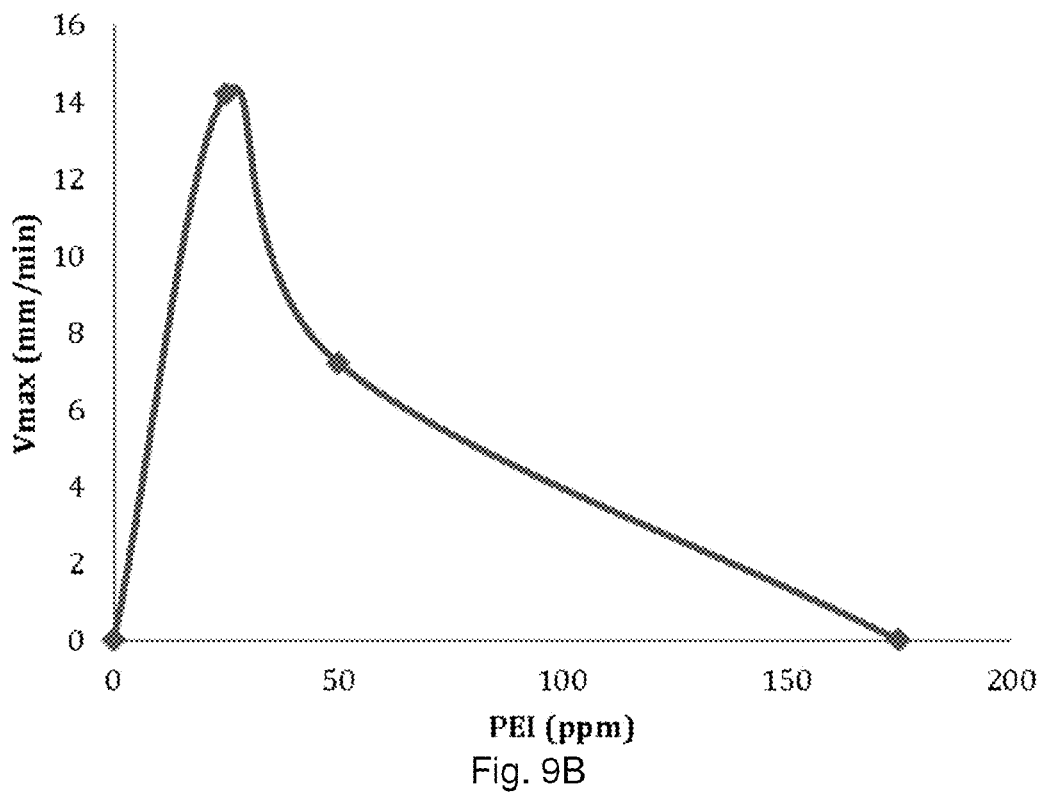
Figure 9C:
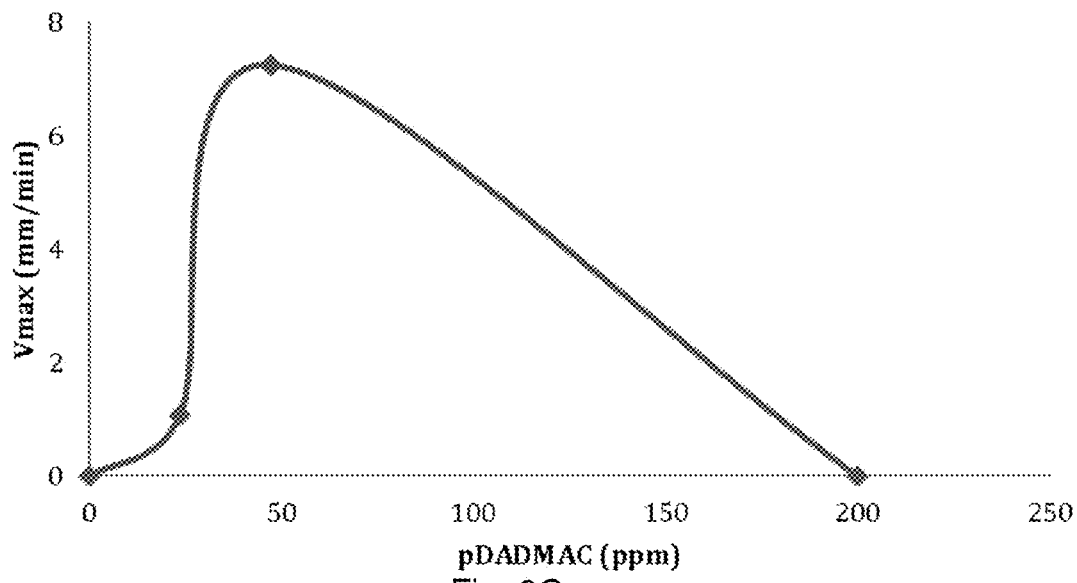
Figure 9D:
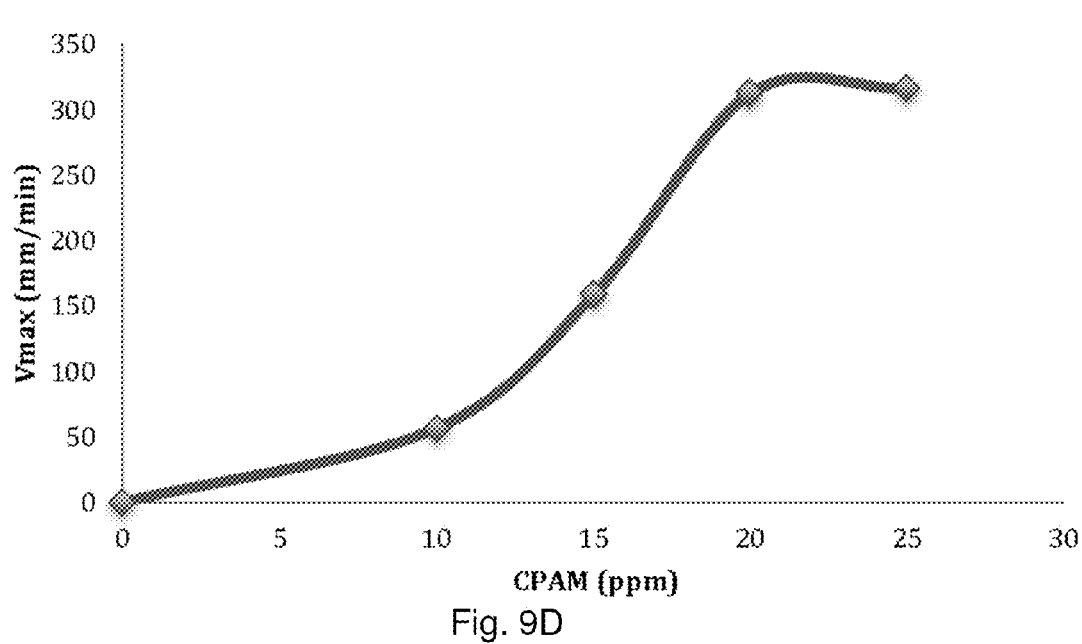
Figure 10A:
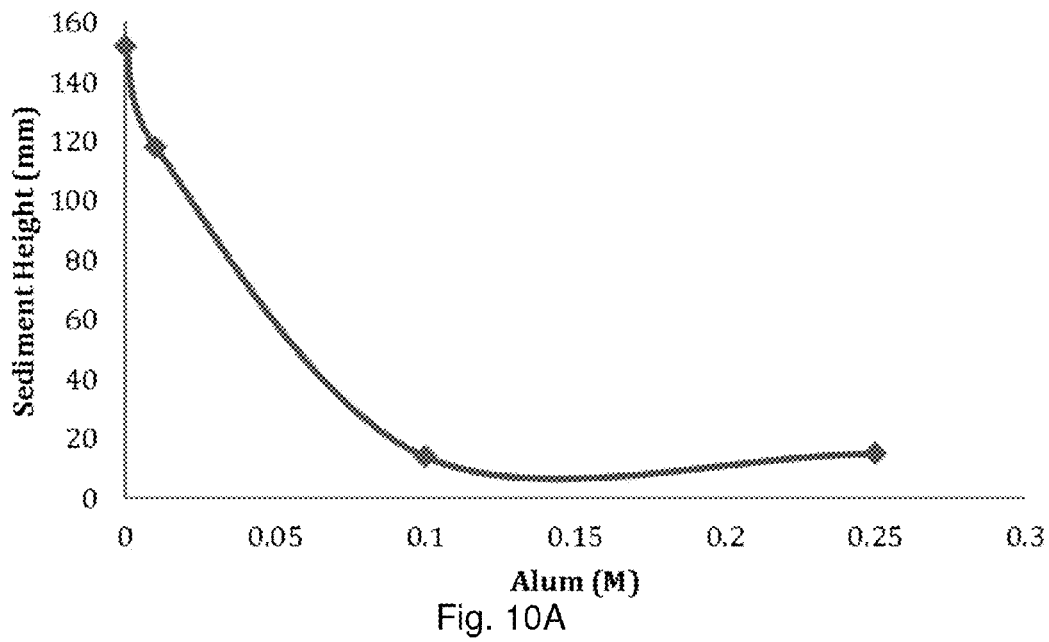
FIGS. 10A-10D show graphs of sedimentation height vs. flocculating agent concentration for Alum (FIG. 10A), PEI (FIG. 10B), pDADMAC (FIG. 10C), and CPAM (FIG. 10D)
Figure 10B:
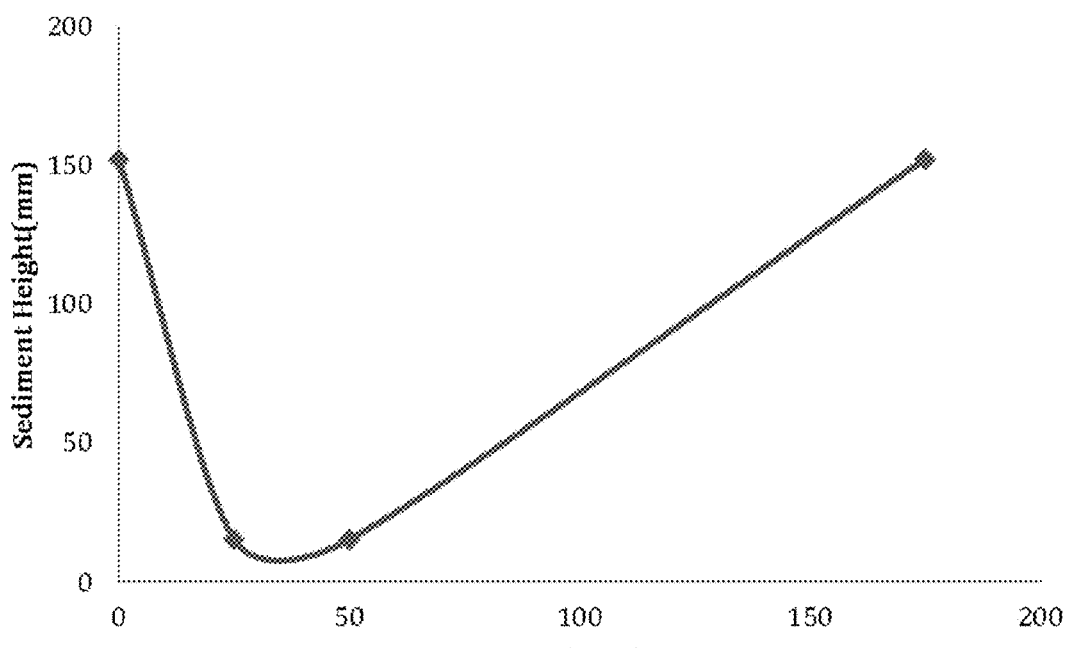
Figure 10C:
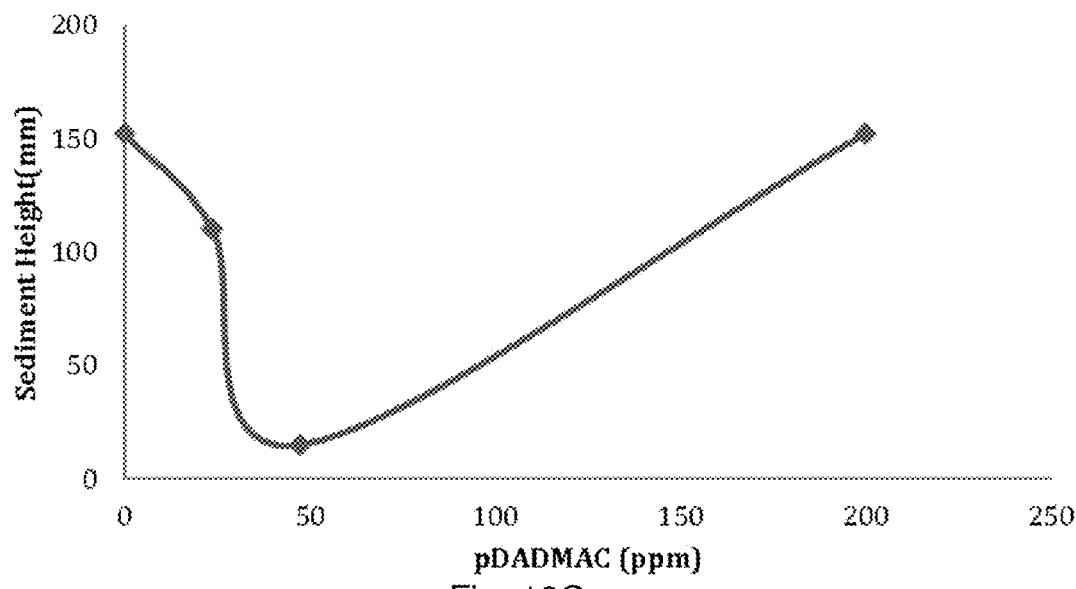
Figure 10D:
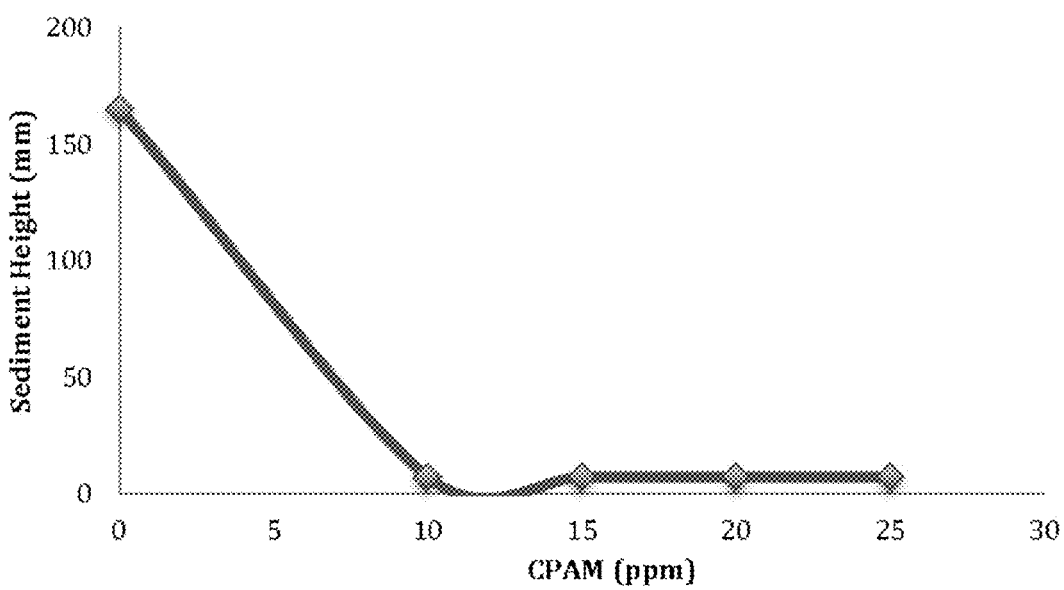

FIGS. 5A-5C show the maximum zeta potential attained by the suspension as a function of the dosage of each flocculant (since CPAM showed only a small change, its effect is not shown). Application of higher concentrations of the polymeric flocculants PEI and DADMAC result in charge reversal and cationization of the particles whereas higher concentrations of alum show negligible cationization (~5 mV). Alum is effective at screening the initial charge repulsions between the particles and flocculates the suspensions by reducing the electrical double layer repulsion between the negatively charged particles. On the other hand, the polymers adsorb to the particle surfaces and can cause redispersion of the suspensions at higher dosages.

Figure 3D:
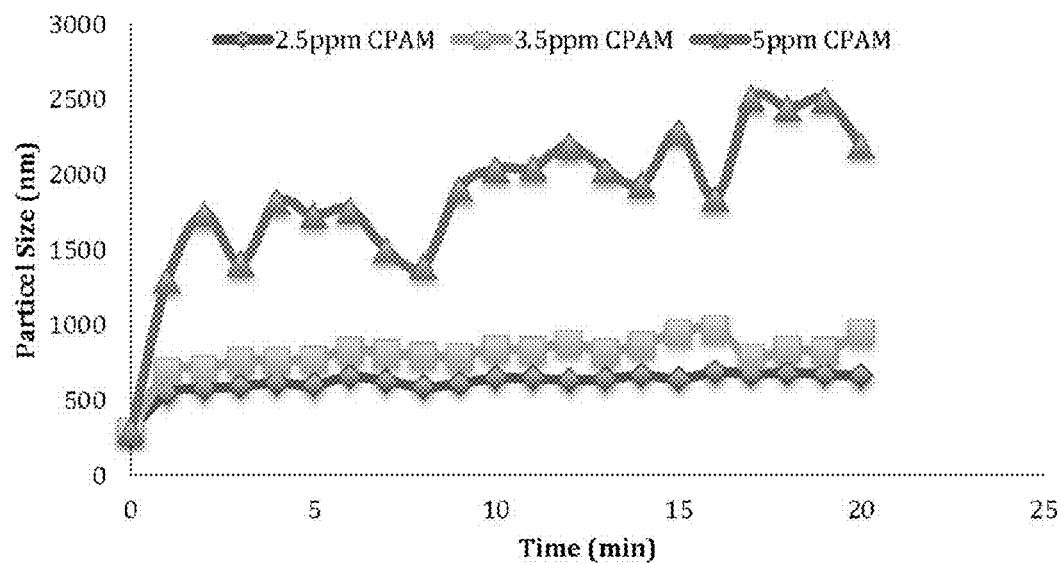

FIGS. 6A-6F show the turbidity of the suspensions with the different flocculants. All the flocculants are effective at reducing the turbidities of the hydrolyzates. Addition of alum reduced the turbidity of the neat hydrolyzates at 0.1 and 0.25 M. Concentrations higher than this did not change the turbidity or flocculation further. Increasing dosages of PEI and pDADMAC resulted in rapid reductions in turbidity, proportional to the dosage as long as the dosage was below the optimal value (defined as that required to neutralize the zeta potential) (in FIGS. 5A-5C). Higher dosages than the optimum resulted in a corresponding reduction in the rate of turbidity changes. This is indicative of the adsorption/patching mechanism for flocculation, especially since the charge is reversed to cationic values as observed in FIGS. 5A-5C. The impact of adding alum and PEI together was investigated. It appears that the combination of electrolyte (alum) and polymer (PEI) is just as effective as either one acting alone showing that alum simply reduces the amount of anionic charge available for neutralization by subsequent PEI. The average particle size in presence of the flocculant was observed to increase beyond 3000 nm (the upper limit of particle sizer) with all the three polymers. Two cationic polyelectrolytes of medium and high MW were added to the hydrolyzates. The change in turbidity was faster with the two CPAM polymers, similar to the rate of aggregate size growth as seen in FIG. 3D. Furthermore, much lower dosages were necessary for flocculation and the eventual clear supernatant was also found to have lower turbidity than those obtained with the other flocculants. The medium molecular weight CPAM is more effective than the higher MW CPAM as is evident from FIGS. 6D and 6E. The reason for the difference in their action is unclear at this point. Flocculation and sedimentation are strongly impacted by charge density and molecular weight of polyacrylamides [44].

FIGS. 7A-7F show the height of the settling interface as a function of time, with the application of these flocculants at different dosages. The settling of the particles was very rapid with the CPAM as the particles were already aggregated in the agitation process. The application of alum also results in sedimentation of the suspensions. Increased dosage beyond that necessary for charge neutralization does not affect the settling rates. The application of PEI and DADMAC results in settling of the suspensions also, with DADMAC at 47.3 ppm being very effective in the separation. The combination of alum and PEI also results in the settling of the suspensions. The kinetics of flocculation varied from polymer to polymer, flocculation with PEI showed rapid sedimentation when compared with alum and pDADMAC. Sedimentation did not occur for lower concentrations of alum (0.01M) and DADMAC (23.6 ppm). The height of the sediment volume depended on rate of aggregation of particles with faster aggregation resulting in rapid sedimentation and larger floc sizes.

FIGS. 8A-8D show the settling velocity measured by numerically differentiating the settling height curves. The settling velocity is usually a constant value independent of time for unflocculated slurries under hindered settling conditions. The settling velocities of the suspensions however show significant variation with time. The initial increase in settling velocity is due to the formation of flocs. As flocs form and begin to settle, they interfere with each other leading to a reduction in the settling velocity. The settling velocities also show a characteristic slow decrease at long times. This behavior can be expected for the settling of consolidated beds or suspensions that are consolidating at concentrations above their gel point. Further analysis of the settling behavior of these suspensions is being conducted to characterize their 'gel' points. The settling velocity increases with higher flocculant dosages. However, the settling velocity appears to be similar for flocs formed from alum at different concentrations.

The maximum in the settling velocity found is shown as a function of the concentration of the flocculant dosages in FIGS. 9A-9D. It is interesting to note that the flocs induced by the simple electrolyte alum show a maximum settling velocity that is independent of dosage beyond 0.1 M. Flocs appear to attain a maximum size at this dosage and the electrolyte's influence reaches a plateau. The behavior of flocs of PEI and DADMAC is different. The settling velocity $v_{max}$ shows a sharp maximum, which occurs at the optimal polymer dosage. The increasing part of the curve is due to increased flocculation with higher flocculant levels. The decrease in settling velocity occurs because some of the particles have acquired larger cationic charges hindering the flocculation process. This will result in smaller floc sizes as well reduced overall flocculation.

FIGS. 10A-10D show the settled sediment height as a function of polymer dosage. These curves follow the same trends as the maximum settling velocities. The cationic flocculants adsorb onto the anionic particle surfaces and also screen the electrostatic repulsions between the particles. Reduced repulsion results in more compact sediments as indicated by the curves in this set of figures. The reversion of charges due to higher polymer dosages results in the reappearance of the electrostatic repulsions increasing the sediment heights (reducing their concentrations).

FIGS. 9A-9D and 10A-10D taken together show that both the dynamic and steady state characteristics of solid liquid separations (sedimentation, filtration, and centrifugation) will be strongly impacted by flocculation of the hydrolyzates. Higher settling velocities indicate significant increase in the hydrodynamic mobilities and rapid separations whereas the more compact sediments (and by implication, concentration) will deliver greater solid and liquid yields. Sedimentation and filtration characteristics, in particular the particle yield stresses, the gel points and their dependence on sediment or suspension volume fractions, are strongly dependent on flocculation and the specifics of polymer adsorption [44].

FIGS. 11A-11D are optical micrographic images of the suspensions with the three flocculating agents at their optimal dosages. Particles of the neat hydrolyzate are shown in FIG. 11A. The hydrolyzate particle size measured earlier [15] was in the range of 250 to 500 nm, much smaller than the entities visible in (a). These represent agglomerates occurring due to increased concentration of the suspensions under the microscope. The flocs seen in FIGS. 11B-11D however represent images of the native flocs in the hydrolyzates induced by the corresponding flocculants. The flocs due to the polymers (FIGS. 11C and 11D) are much larger than those due to the alum (shown in FIG. 11B). This confirms the results of particle size measurements in FIGS. 3A-3D. The particles flocculated with PEI (FIG. 11D) are closely aggregated and larger than flocs of pDADMAC and alum. The clear solutions of the polymer treated supernatants after the sedimentation. The clarity of the supernatants was substantially improved with flocculant addition.

Lignocellulosic feedstocks are quite diverse, ranging from hardwood chips to agricultural wastes, and therefore can yield hydrolyzates of varying composition. An important variable is the hydrolyzate pH which depends on the organic acid content of the feedstock, the pretreatment method and its conditions. Hardwoods such as sugar maple are rich in acetylated xylans and mild acid or auto catalyzed hot water pretreatments give yield significantly acidic hydrolyzates with pH less than 4.0. Hydrolyzates used had a baseline pH of 3.5. The addition of alum reduced this to 3.2 while the polymeric flocculants did not significantly change the baseline. The charge of many polymers is pH sensitive due to the dependence of the degree of ionization of their functional groups. The zeta potential of the wood hydrolyzates becomes more negative with increased pH, primarily due to the dissociation of additional surface groups on the particles [15].

Due to its importance, the effect of changing pH on the action of the flocculants was investigated as follows. FIG. 12 shows the variation in turbidity of the wood hydrolyzates as a function of their pH (adjusted from its original value of 3.2 by using HCl or NaOH respectively). A decrease in the pH to 1.5 caused only a marginal change in the turbidity although visual observation indicated the formation of larger particles. Lignin that is insoluble in acid conditions precipitates out of the solution and forms larger particulates. As pH is increased on the other hand, a distinct reduction in turbidity is observed since more of the lignin becomes soluble and goes into solution. At pH of 8, the turbidity has reduced significantly, by almost tenfold. The normal pH of the hydrolyzate was 3.5. When the pH was adjusted to 6.1 the zeta potential of the suspension increased (more negative charges observed).

Figure 13A:
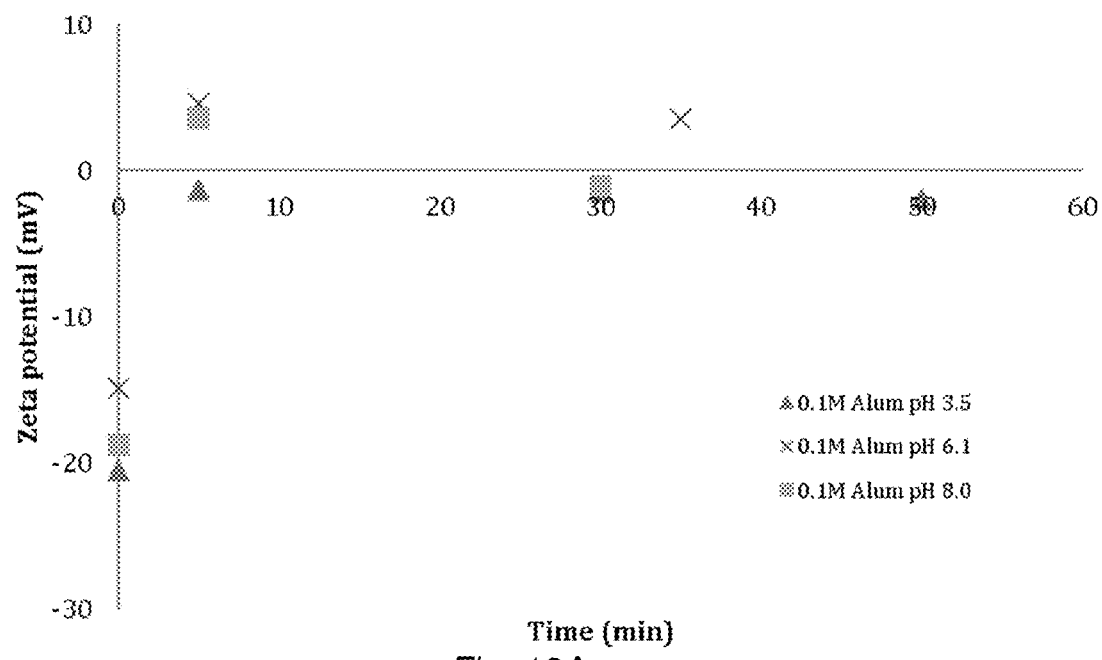
FIGS. 13A-13D show graphs of zeta potential vs. time for Alum (FIG. 13A), PEI (FIG. 13B), PEI (FIG. 13C), and pDADMAC (FIG. 13D)
Figure 13B:
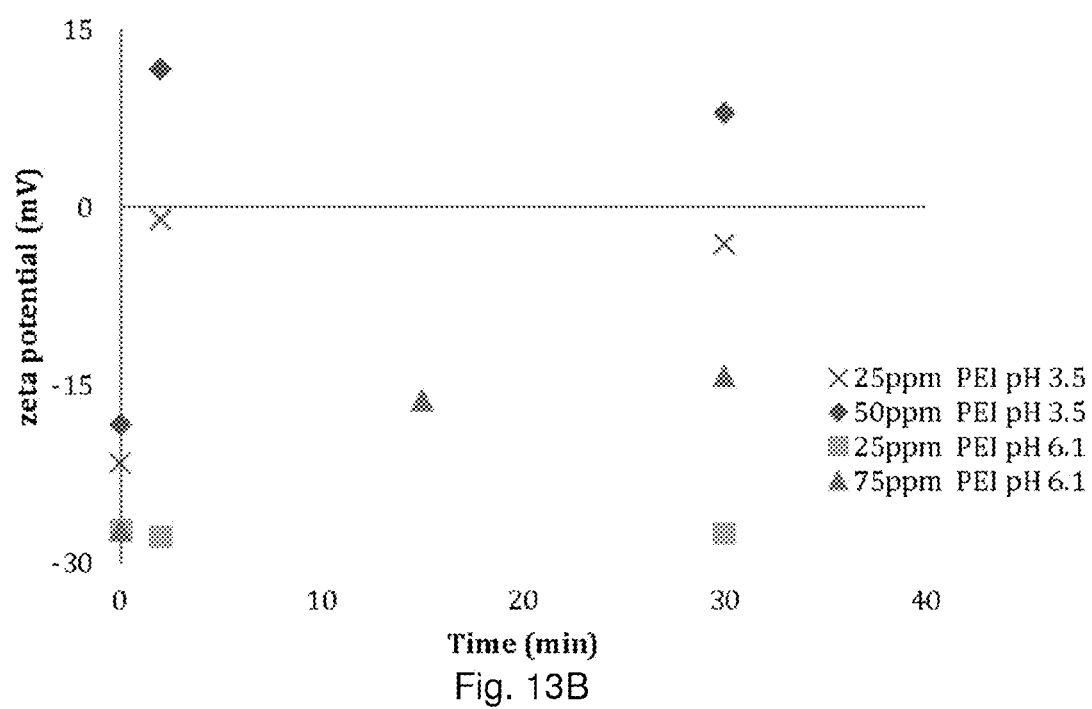
Figure 13C:
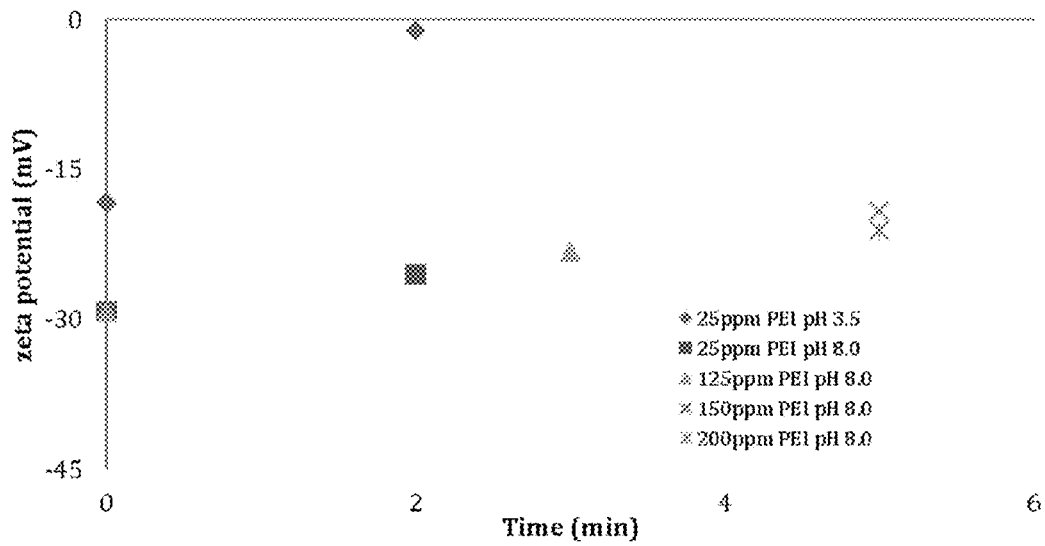
Figure 13D:
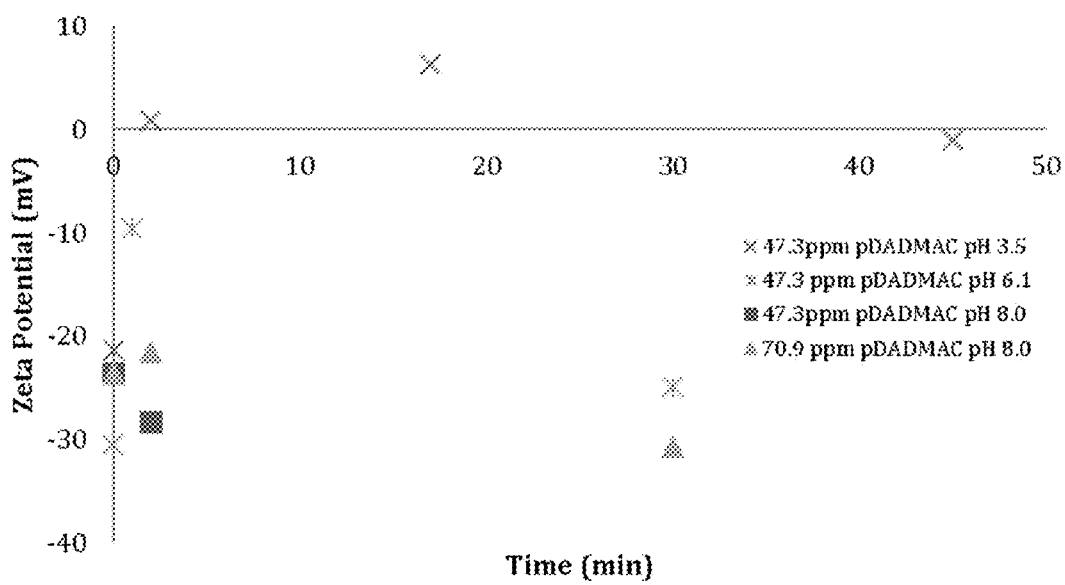
Figure 14A:
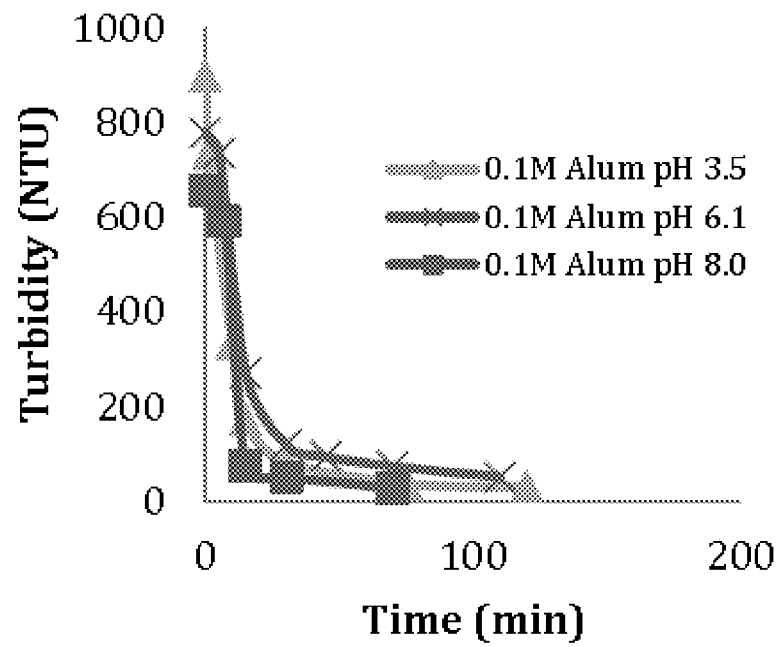
FIGS. 14A-14D show graphs of turbidity (NTU) vs. time for Alum (FIG. 14A), pDADMAC (FIG. 14B), PEI (FIG. 14C), and med. mol. wt. CPAM (FIG. 14D)
Figure 14B:
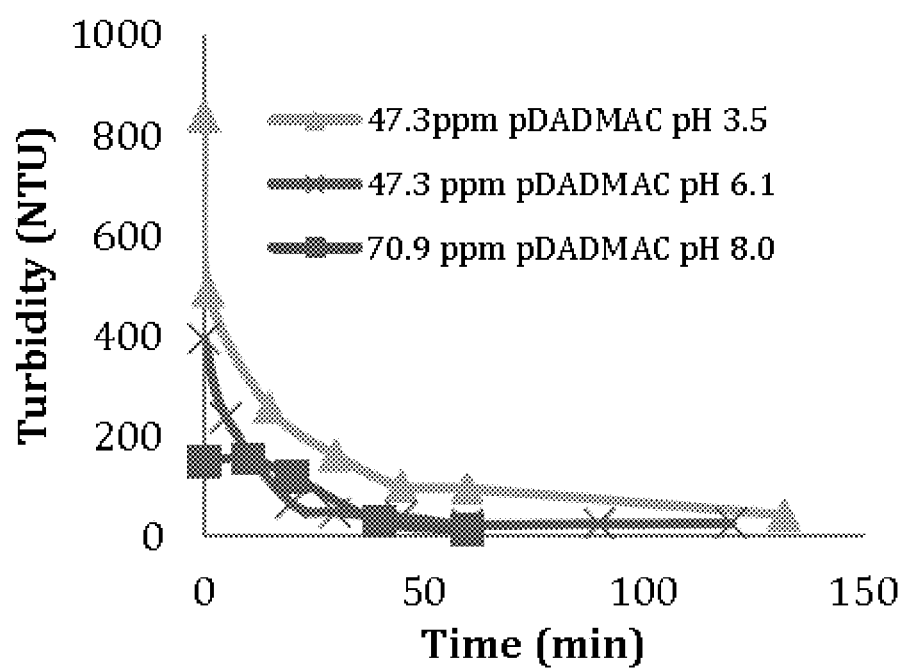
Figure 14C:
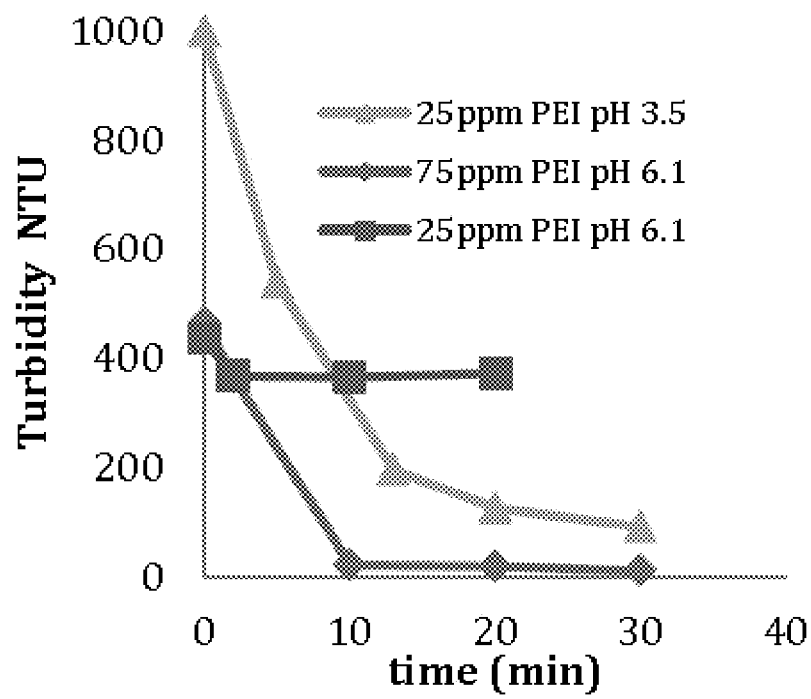
Figure 14D:
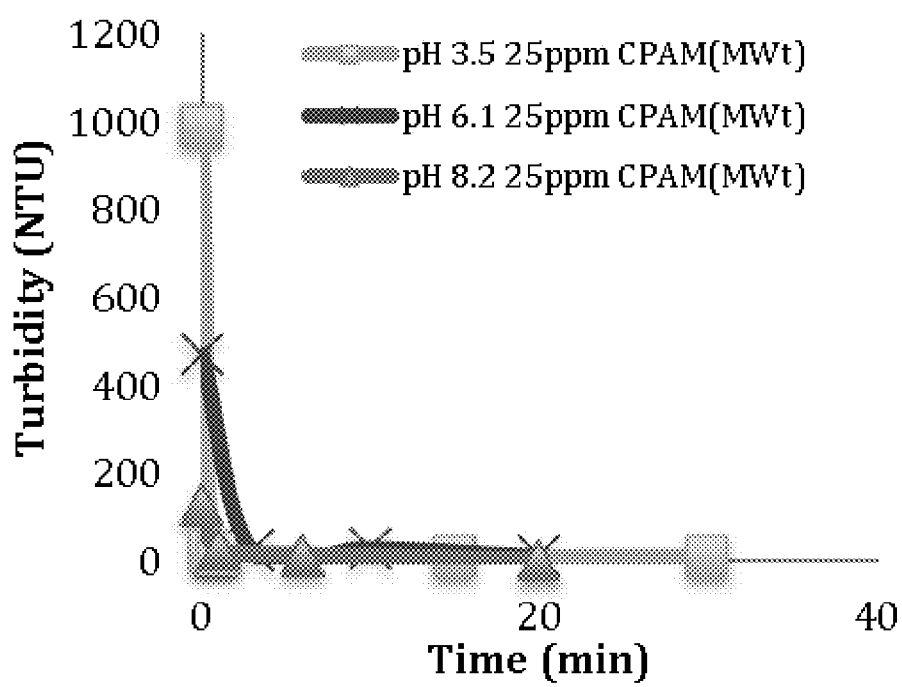

FIGS. 13A-13D shows the change of zeta potential with time for each of the flocculants at different dosage levels. Three pH levels (3.5, 6.1 and 8.2) were considered. When alum was added to the native extract, the pH drops from an initial value of 3.4 to 3.2 due to the buffering action of the alum. Even when the initial pH of the hydrolyzate was changed to 6.1 or 8.0, the addition of alum decreased the suspension pH to near 3.5 due to the strong buffering action of alum. It is seen that the zeta potential increases to slightly positive values but for the higher (initial) pH it reverts to slightly negative values with time. At higher pH, the speciation reactions of alum are altered and polynuclear complexes occur which precipitate easily [41]. There is a slight increase in the zeta potential with alum addition, perhaps because of this additional precipitation at the higher pH values. With an initial pH of 8, the zeta potential is slightly negative indicating that the charge neutralizing capacity of the alum is reduced somewhat. This could be due to the higher anionic charges on the suspended particles and also due to the fact that increased suspension pH especially near 8 can yield anionic species of alum in solution. Note that the predominant species of alum in solution at pH 8, $Al(OH)_4$ [41] is anionic. The charge decay effect with time can be understood to be a consequence of this increased pH. The polyelectrolytes on the other hand did not affect the pH of the hydrolyzate significantly and the final suspension pH was equal to the initial value. The action of PEI is significantly affected by pH as shown by FIG. 13B. At the higher pH of 6.1, dosages of 25 and even 75 ppm PEI leaves the suspension with a negative zeta potential. For the case of pDADMAC too, higher pH of the suspension seems to result in a net negative zeta potential. The rate at which the zeta potential reverts to its original (negative) value is also greater at the higher pH. The charge of PEI decreases as the pH increases due to deprotonation of the imine group. Hence, the ability of PEI to neutralize the particles' negative charge is substantially impeded at pH 8.0. Since the charge on PEI is known to decrease with pH, this result can be expected. The addition of pDADMAC did not cause charge reversal at the high pH level of 8.0.

The impact on turbidity is shown in FIGS. 14A-14D. At pH 6.1, PEI reduced the turbidity by 90% whereas at pH of 3.5, the reduction was close to 100%. The action of pDADMAC on the other hand is not so drastically affected by pH as the PEI, although it appears that the optimal dosage of pDADMAC for flocculation is shifted to higher values as compared to the lower pH suspension.

Figure 15A:
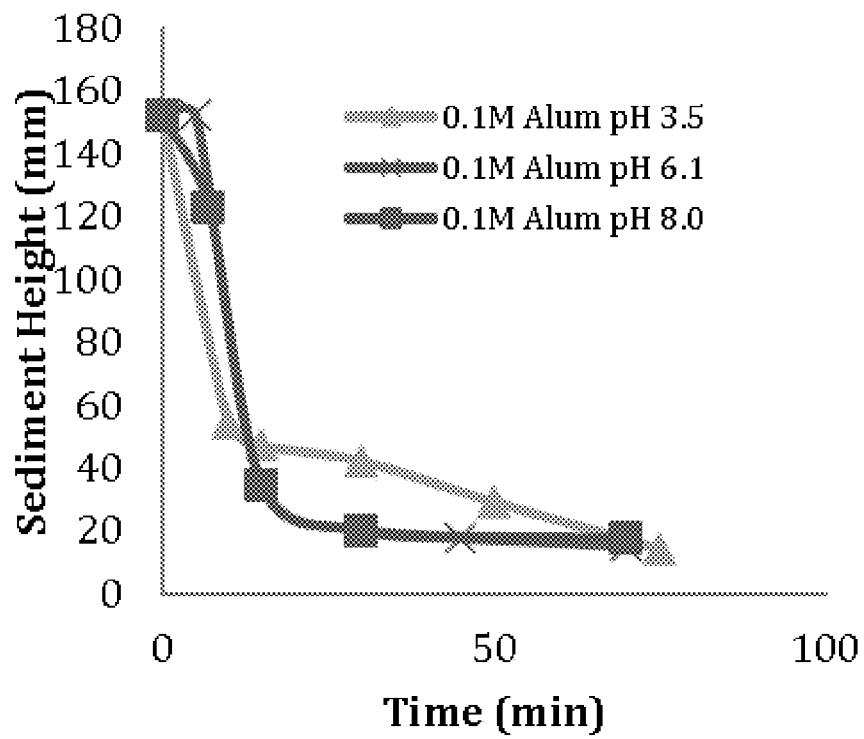
FIGS. 15A-15D show graphs of sedimentation height vs. time for Alum (FIG. 15A), pDADMAC (FIG. 15B), PEI (FIG. 15C), and med. mol. wt. CPAM (FIG. 15D)
Figure 15B:
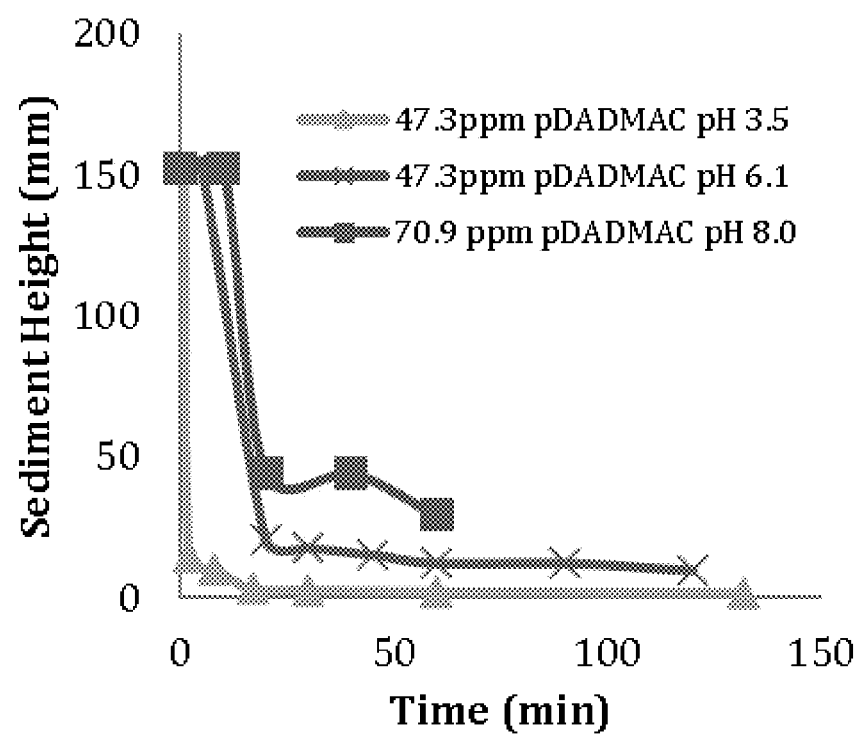
Figure 15C:
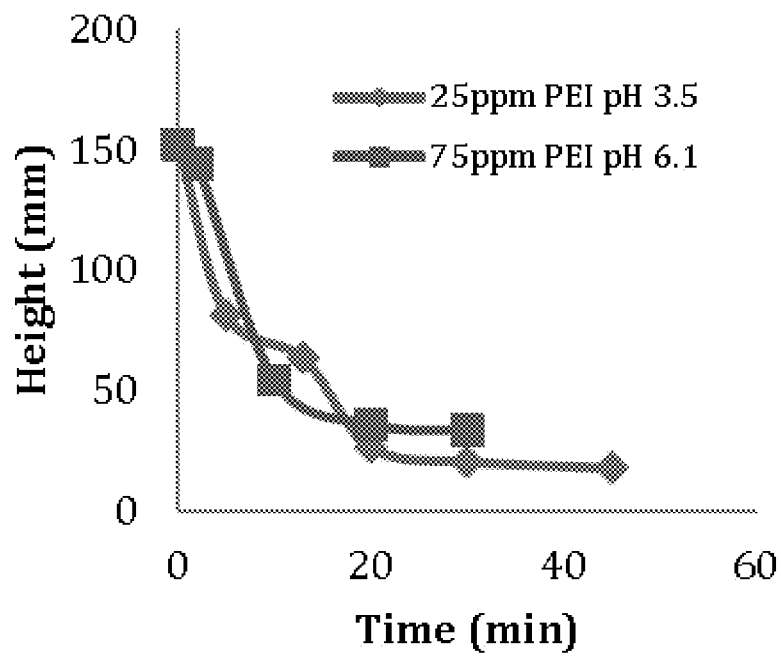
Figure 15D:
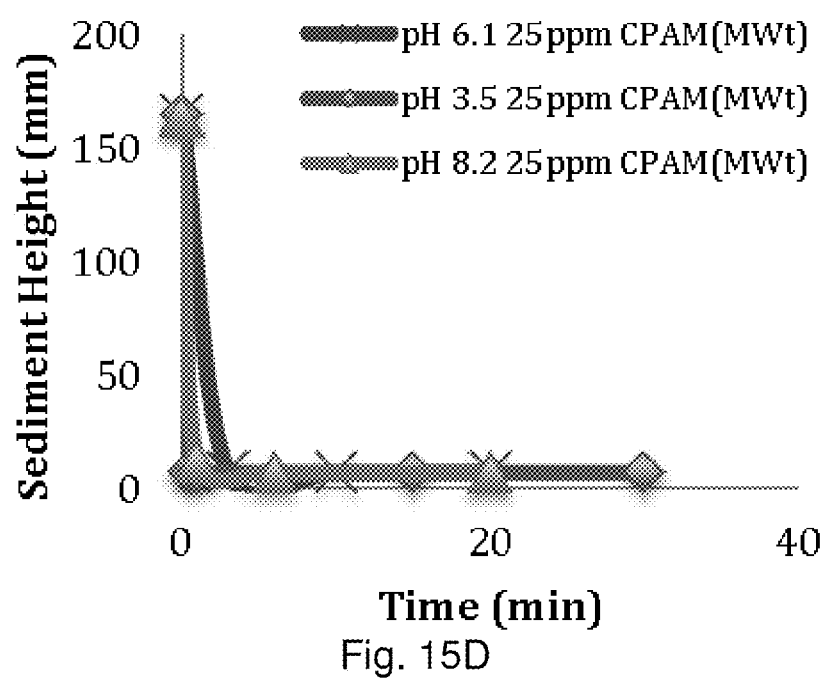
Figure 16:
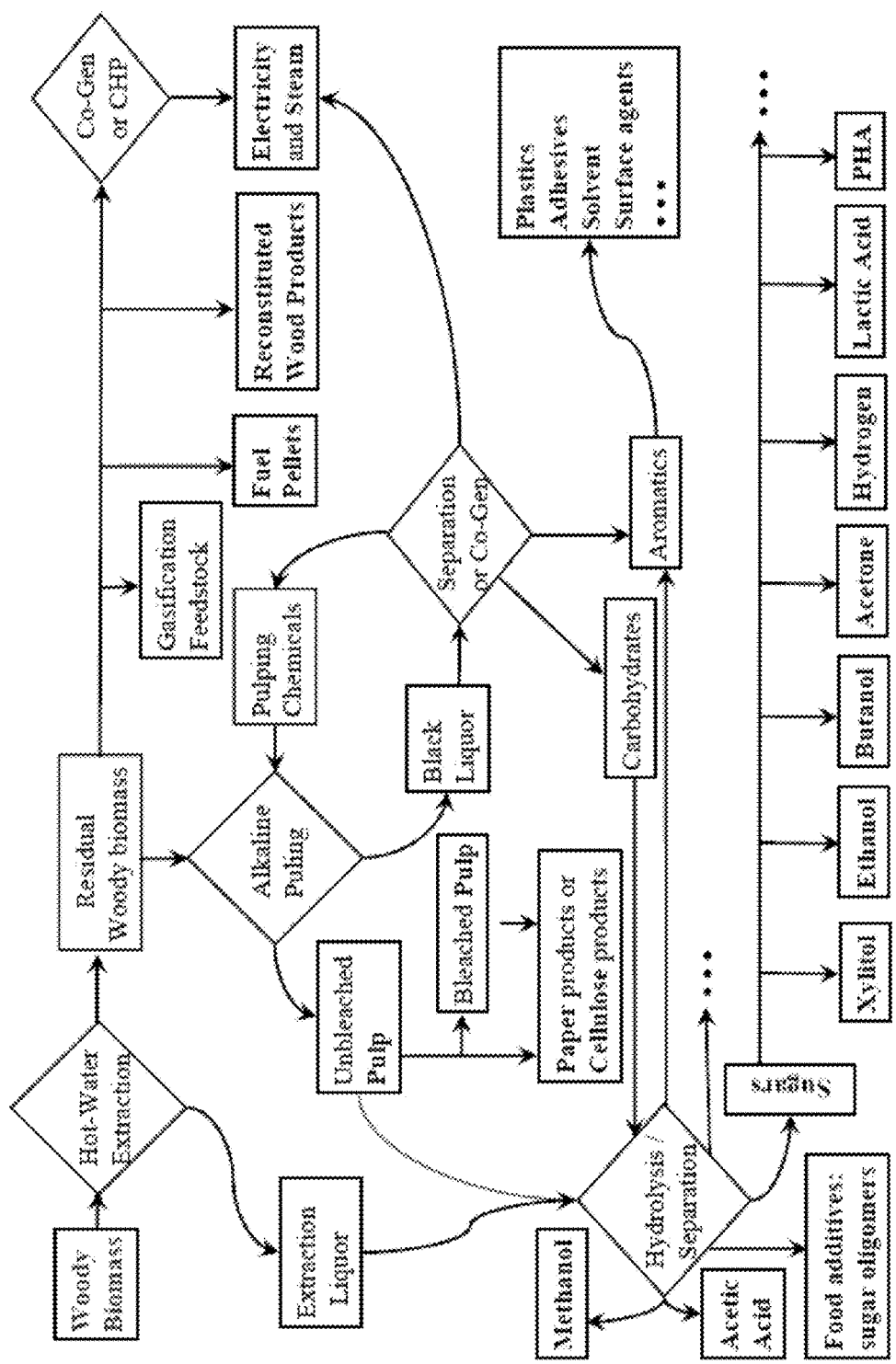
FIG. 16 shows a flow chart of a lignocellulosic biomass process.

FIGS. 15A-15D show the impact of the flocculants on the settling curves. At the pH of 8.0, PEI did not result in any flocculation or settling. At the intermediate pH of 6.1, the settling was similar to that at lower pH although the settling velocity appears lower. The final settled height is lower indicating more compact sediment at the lower pH (3.5). In the case of alum, the settling velocity is slightly smaller with higher pH but the sediment height is also smaller. This is repeated when the pH is increased to 8.0 too. The case of DADMAC is similar to PEI. Increased pH resulted in slower settling and higher settled volume (height), both indicative of stronger residual repulsions. The rate of sedimentation was rapid with higher concentration of PEI at pH 6.1 (FIG. 15C). There was no sedimentation at pH 8.0. This study shows that polymers PEI and pDADMAC were sensitive to pH of the solution and alum was buffering agent. The effect on the CPAM was minimal.

Figure 27A:
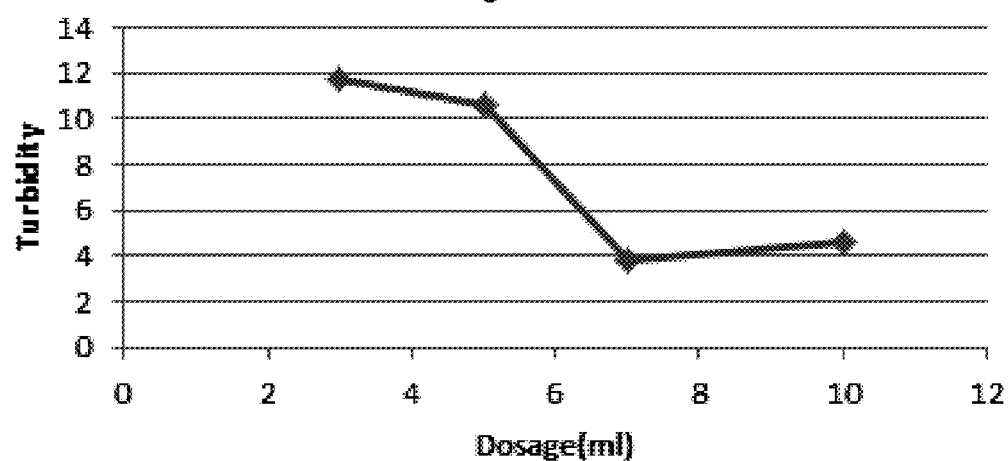
FIGS. 27A and 27B show graphs of turbidity vs. dosage of polymer solution at 1 g/l (FIG. 27A), and 2 g/l (FIG. 27B).
Figure 27B:
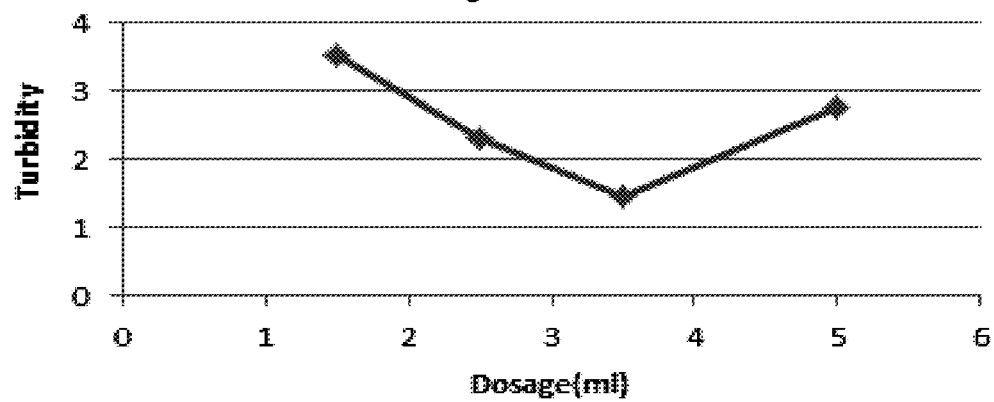

FIGS. 27A and 27B show that under different dilutions (1 g/l and 2 g/l) each display the same optimum flocculation concentration.

The impact of flocculation and resultant sedimentation on the composition of the hydrolyzates was analyzed. Table 2 shows the composition of sugars and lignin in the neat extracts (hydrolyzates) and supernatants of the polymer treated extracts. The application of pDADMAC led to reductions in the concentration of the total sugars from ~37% to ~24% and a drop in the lignin contents of more than 50%. The stronger action of pDADMAC may stem from its higher charge density and lower MW. Alum captured sugars in similar proportion but was less effective at removing the lignin in both acid insoluble and soluble forms. The Al cation is also highly charged and is nonselective between lignin and the carbohydrates in dissolved forms causing equal precipitation or agglomeration and removal. It appears that PEI is more selective in removing lignin (>50% removal) while affecting the sugar yields to smaller extents (~30% remaining in solution compared to 37% in the neat hydrolyzates). PEI has a stronger affinity to lignin compared to the sugars perhaps due to the stronger charges on the lignin.

TABLE 3

Chemical Composition of hydrolyzates before and after polymer treatment.

| (g/L) | Neat Extract | PEI | Alum | pDADMAC | CPAM |
|---|---|---|---|---|---|
| Galactose | 1.31 | 1.03 | 0.91 | 0.77 | 1.002 |
| Xylose | 27.78 | 22.17 | 21.35 | 17.79 | 24.34 |
| Rhamnose | 1.29 | 0.97 | 0.88 | 0.73 | 0.836 |
| Mannose | 3.26 | 2.14 | 1.78 | 2.22 | 2.4544 |
| Arabinose | 1.55 | 1.31 | 1.31 | 0.99 | 1.3016 |
| Glucose | 2.72 | 1.80 | 1.78 | 1.49 | 1.51 |
| Total Sugars | 37.91 | 29.42 | 28.01 | 23.97 | 31.44 |
| Furfural | 1.34 | 1.73 | 1.60 | 0.43 | 1.7 |
| 5-HMF | 0.33 | 0.14 | 0.13 | 0.14 | 0.082 |
| Acetate | 7.24 | 6.21 | 6.15 | 4.47 | 6.8 |
| Lignin: (g/L) | | | | | |
| Acid Soluble | 0.68695 | 0.39 | 0.55 | 0.325 | 0.61 |
| Acid Insoluble | 4.86 | 1.92 | 2.88 | 1.32 | 1.12 |
| Total Lignin | 5.54695 | 2.31 | 3.43 | 1.645 | 1.73 |

Polyethylene Oxide

Figure 20:
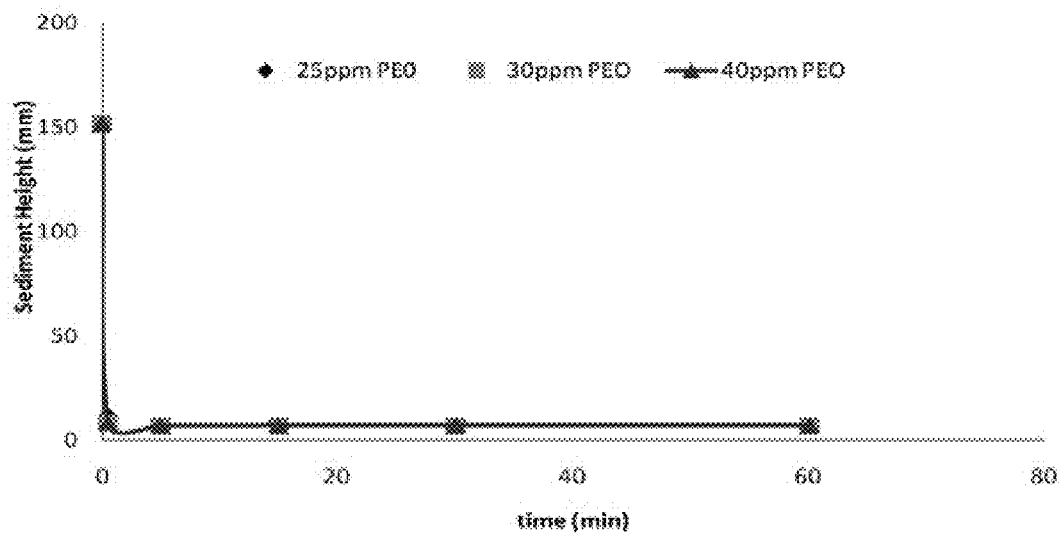
FIG. 20 shows a graph of sediment height vs. time.

FIG. 20 shows the height of the sediment volume vs. time for different concentrations of the polymer. The setting velocity is very rapid at the initial stage of the sedimentation process. The turbidity of the supernatant was also varied with sedimentation of the aggregated particle.

Figure 21:
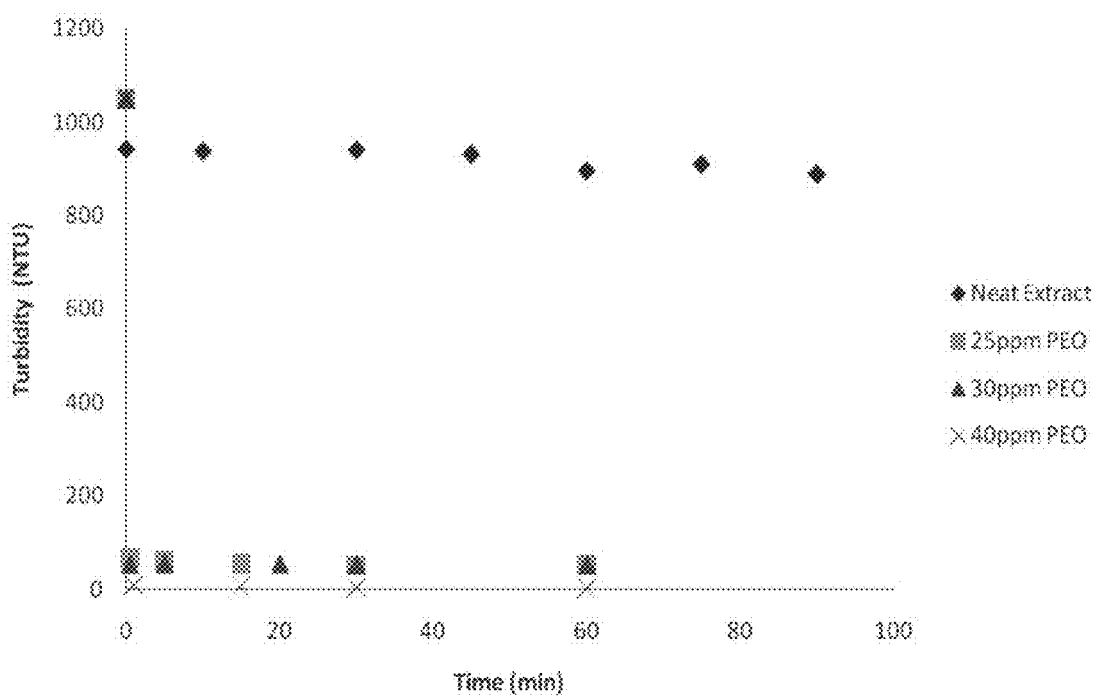
FIG. 21 shows a graph of turbidity vs. time for different concentrations of polymer.

FIG. 21 shows the change in turbidities with time at different concentrations of the polymer.

Figure 22:
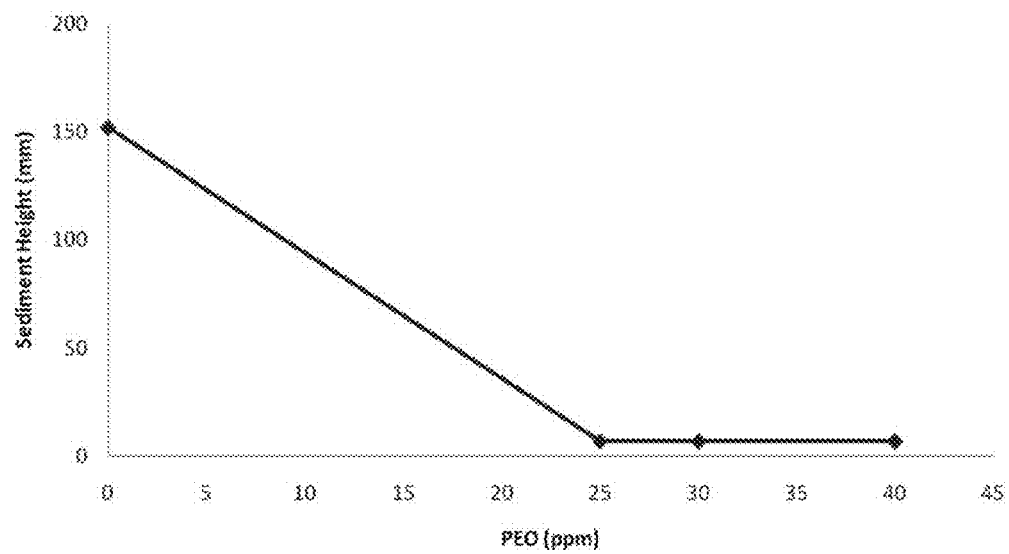
FIG. 22 shows a graph of maximum sediment height vs. polymer concentration.

FIG. 22 shows the maximum sediment height vs. polymer concentration. The maximum sedimentation height of the flocculated particles after one hour sedimentation process was same for all concentrations of the polymer.

Figure 23:
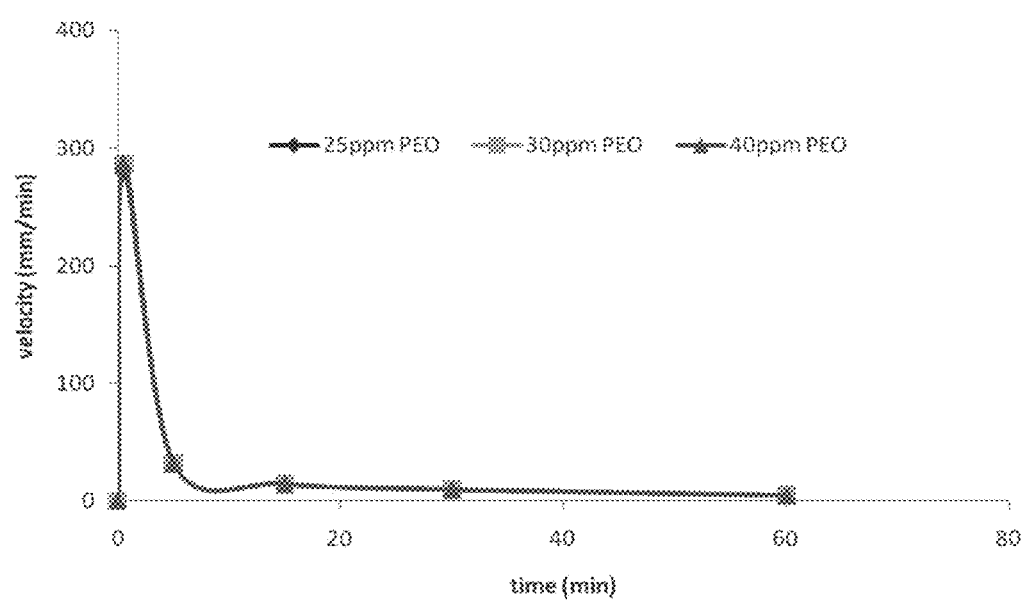
FIG. 23 shows a graph of settling velocity vs. time of sedimentation.

The settling velocities of the aggregated particles in the wood extract were calculated and shown in the FIG. 23.

Figure 24:
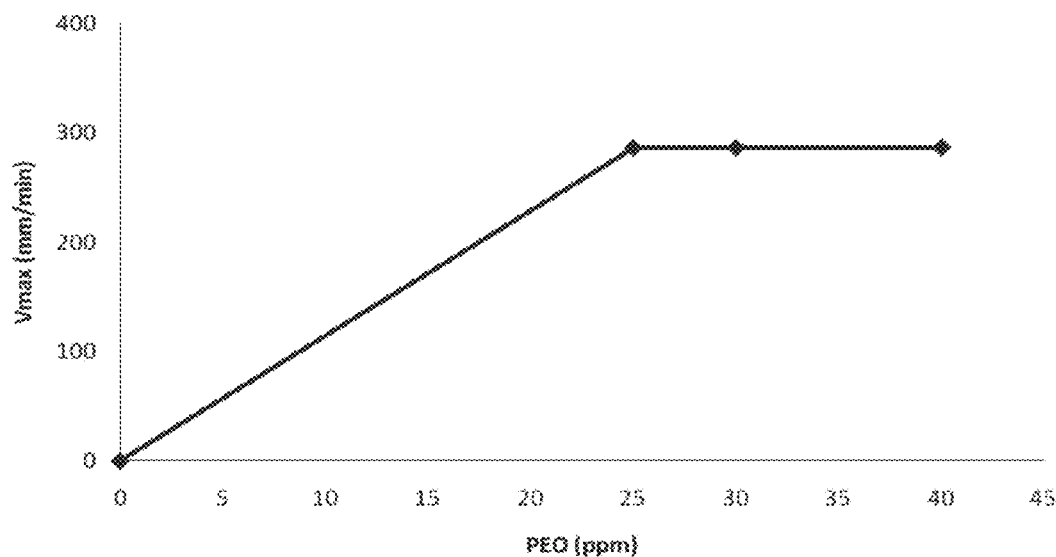
FIG. 24 shows a graph of maximum settling velocity vs. polymer concentration.

The maximum settling velocities of the aggregated particles at different concentrations of the polymer are very near to each other, and were shown in the FIG. 24.

Figure 25:
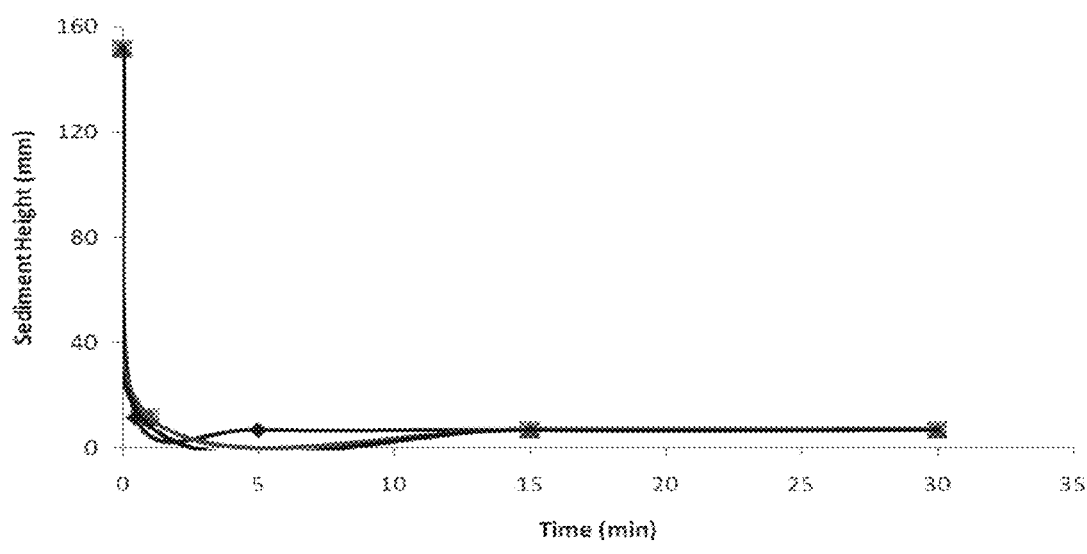
FIG. 25 shows a sediment height vs. pH of extract at 40 ppm PEO.

The effect of pH on the flocculation was examined by varying the pH of the extract between about 2 and about 9. The wood extract pH was changed by using dilute $H_2SO_4$ and NaOH solutions. The PEO polymer concentration of 40 ppm was added to the extract and mixed homogenously by magnetic stirrer. The aggregation of the particles was observed in the mixing process and the suspension was further processed for sedimentation for 30 minutes. This is shown in FIG. 25. Although the pH of the extracts was varied the effect on suspension stability was minimal. The temperature was maintained constant at 25° C.

The effect of temperature on polymer flocculation was studied in between the temperature range of 15-25° C. The wood extract after extraction was stored in the cold room to maintain the temperature around 10 C and was used for the work. The PEO polymer concentration of 40 ppm was used initially for all temperature ranges and optimal temperature for the flocculation was found to be at 21.5° C. in the agitation process. Then the suspended solution was processed for sedimentation.

Figure 26:
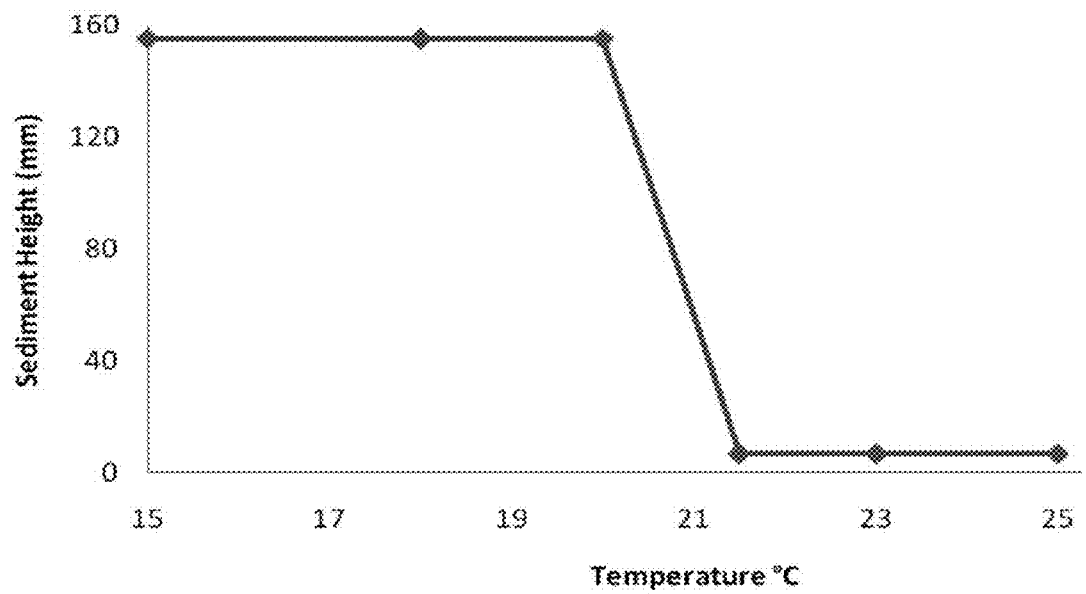
FIG. 26 shows a graph of final sediment height vs. temperature.

FIG. 26 shows the final sediment height at different temperature conditions at optimal concentration of 40 ppm PEO. At temperatures below 21.5° C., the aggregation of particles was not noticed even at higher dosage levels of up to 150 ppm.

Flocculation and clarification with PEO were demonstrated on large pilot scale batches of 1000 kg of extract with optimal polymer dosage of 50 ppm PEO at 25° C. temperature conditions. Further, the flocculated extract was mixed with commercially available soft wood pulp, which acted as a filter aid to adsorb flocculated particles and the suspended mixture was filtered through a 5 micron pore size filter cloth. The filtrate showed a 99.5% reduction in turbidity, from 12,000 NTUs in the raw extract to 50 NTUs in the filtrate.

The overall lignin and sugars composition in the supernatant of the extract was analyzed after the sedimentation. The optimal concentration of 40 ppm was used for the flocculation and the supernatant was used for the analysis. The polysaccharides were analyzed by 1H NMR and lignin by standard TAPPI methods. The composition was shown in Table 3. The lignin was removed effectively and sugars remained constant in the solution after the PEO polymer induced flocculation.

TABLE 4

Chemical Composition of hydrolyzates before and after polymer treatment (PEO 40 ppm)

| (g/L) | Neat Extract | PEO |
|---|---|---|
| Galactose | 1.31 | 1.001 |
| Xylose | 27.78 | 23.52 |
| Rhamnose | 1.29 | 0.816 |
| Mannose | 3.26 | 2.33 |
| Arabinose | 1.55 | 1.01 |
| Glucose | 2.72 | 1.05 |
| Total Sugars | 37.91 | 29.73 |
| Furfural | 1.34 | 1.52 |
| 5-HMF | 0.33 | 0.13 |
| Acetate | 7.24 | 6.02 |
| Lignin: (g/L) | | |
| Acid Soluble | 0.68695 | 0.107 |
| Acid Insoluble | 4.86 | 1.4 |
| Total Lignin | 5.54695 | 1.507 |

The separation of colloidal particles (lignin and its derivatives) from hot water extracts of sugar maple wood extracts can be achieved by non-ionic polymer PEO. The dynamics of flocculation depends on concentration of the polymer, pH and temperature. The formation of lignin-PEO complex is confirmed by supernatant lignin analysis. The hemicellulose sugars in the supernatant remain constant after the polymer flocculation.

Sequestration of Colloidal Lignin

According to one embodiment, a polymeric flocculant such as the non-ionic polymer PEO is added first to sequester and remove the colloidal lignin, extractives and other interference components. This may be followed by the addition of Calcium Carbonate (PCC) in appropriate dosages to increase the pH and neutralize acetic acid present in the hydrolyzate. The below-described experiments demonstrate the feasibility of this approach.

A lignocellulosic hydrolyzate produced by acid-catalyzed steam explosion pulping of a combination hardwood biomass sample was chosen for analysis. The sample (denoted A) was divided into two parts (denoted B and C). Both B and C were treated with PEO. C was further treated with calcium carbonate (CaCO$_3$, in the precipitated form also known as PCC). The pH of the final solutions and other properties are shown in the table below.

TABLE 5

Effect of PEO and PCC on Hydrolyzate

| Sample | Name | pH | Turbidity, NTU | Mean Particle size, nm |
|---|---|---|---|---|
| A | Initial | 2.5 | 26 | 300 |
| B | Control (A + PEO, 7 ml) | 2.5 | 3 | n.d. |
| C1 | Detox (B + PCC), 75 µg | 4.10 | 2 | n.d. |
| C2 | B + PCC, 125 µg | 5.75 | 3 | n.d. |
| C3 | B + PCC, 250 µg | 6.20 | 3 | n.d. |
| C4 | B + PCC, 500 µg | 6.51 | 4 | n.d. |

As demonstrated in Table 5, no particles were detected up to a pH of 6.51. When the dosage of PCC was increased further, turbidity reappeared with particles being formed in the solution.

The presence of Ca$^{2+}$ ions in solution can be beneficial by accelerating the fermentative action of microbes. Calcium is a micronutrient and thus can offer an additional advantage to the treated hydrolyzates. This facilitation of microbial growth may be the cause of significant quantities of ethanol in the PCC treated hydrolyzates, after analysis.

References (Each of the following reference is hereby expressly incorporated herein by reference.)

1. Liu, S.; Amidon, T. E.; Francis, R. C.; Ramarao, B. V.; Lai Y. Z.; Scott, G. M. Ind.l Biotech. 2006, 2, 113-120.
2. Luo, C.; Brink, D. L.; Blanch, H. W. Biomass Bioenergy 2002, 2, 125-138.
3. Huang, H. J.; Ramaswamy, S.; Tschirner, U. W.; Ramarao, B. V. "Separation and Purification processes for lignocellulose-to-bioalcohol production." In Bioalcohol production: Biochemical conversion of lignocellulosic biomass, Ed. K. Waldron, Woodhead Publishing, CRC Press, 2010, 246-269.
4. Liu, Z.; Fatehi, P.; Jahan, M. S.; Ni, Y. Bioresour. Technol. 2011, 2, 1264-1269.
5. Hasan, A.; Yasarla, R.; Ramarao, B. V.; Amidon, T. E. J. Wood Chem. Technol. 2011, 4, 357-383.
6. Huang, H.; Ramaswamy, S.; Tschirner, U. W.; Ramarao, B. V. Separation and Purification Technology 2008, 1, 1-21.
7. Eken-Saracoğlu, N.; Arslan, Y. Biotechnol. Lett. 2000, 10, 855-858.
8. Miyafuji, H.; Danner, H.; Neureiter, M.; Thomasser, C.; Bvochora, J.; Szolar, O.; Braun, R. Enzyme Microb. Technol. 2003, 3-4, 396-400.
9. Rabelo, S. C.; Filho, R. M.; Costa, A. C. Appl. Biochem. Biotechnol. 2009, 1-3, 139-150.
10. Ranjan, R.; Thust, S.; Gounaris, C. E.; Woo, M.; Floudas, C. A.; Keitz, M. v.; Valentas, K. J.; Wei, J.; Tsapatsis, M. Microporous and Mesoporous Materials 2009, 1-3, 143-148.
11. Villarreal, M. L. M.; Prata, A. M. R.; Felipe, M. G. A.; Almeida E Silva, J. B. Enzyme Microb. Technol. 2006, 1, 17-24.
12. Han, B.; Carvalho, W.; Canilha, L.; da Silva, S. S.; Almeida E Silva, J. B.; McMillan, J. D.; Wickramasinghe, S. R. Desalination 2006, 1-3, 361-366.
13. Mao, H.; Genco, J. M.; Yoon, S.; van Heiningen, A.; Pendse, H. Journal of Biobased Materials and Bioenergy 2008, 2, 177-185.
14. Gong, C. S.; Chen, C. S.; Chen, L. F. Appl. Biochem. Biotechnol. 1993, 1, 83-88.
15. Duarte, G. V.; Ramarao, B. V.; Amidon, T. E. Bioresour. Technol. 2010, 22, 8526-8534.
16. Kim, J.; Akeprathumchai, S.; Wickramasinghe, S. R. J. Membr. Sci. 2001, 1-2, 161-172.
17. Burke, D. R.; Anderson, J.; Gilcrease, P. C.; Menkhaus, T. J. Biomass Bioenergy 2011, 1, 391-401.
18. Menkhaus, T. J.; Anderson, J.; Lane, S.; Waddell, E. Bioresour. Technol. 2010, 7, 2280-2286.
19. Barany, S.; Szepesszentgyörgyi, A. Adv. Colloid Interface Sci. 2004, 1-2, 117-129.
20. Schowalter, W. R. Annu. Rev. Fluid Mech. 1984, 245-261.
21. Besra, L.; Sengupta, D. K.; Roy, S. K.; Ay, P. Separation and Purification Technology 2004, 3, 231-246.
22. Patil, D. P.; Andrews, J. R. G.; Uhlherr, P. H. T. Int. J. Miner. Process. 2001, 3, 171-188.
23. Heath, A. R.; Bahri, P. A.; Fawell, P. D.; Farrow, J. B. AIChE J. 2006, 6, 1987-1994.
24. Haydar, S.; Aziz, J. A. J. Hazard. Mater. 2009, 2-3, 1035-1040.
25. Pearse, M. J.; Weir, S.; Adkins, S. J.; Moody, G. M. Minerals Eng 2001, 11, 1505-1511.

26. Yu, J.; Wang, D.; Ge, X.; Yan, M.; Yang, M. Colloids Surf. Physicochem. Eng. Aspects 2006, 1-3, 288-294.
27. Popa, I.; Cahill, B. P.; Maroni, P.; Papastavrou, G.; Borkovec, M. J. Colloid Interface Sci. 2007, 1, 28-35.
28. Yukselen, M. A.; Gregory, J. Int. J. Miner. Process. 2004, 2-4, 251-259.
29. Rasteiro, M. G.; Garcia, F. A. P.; Ferreira, P.; Blanco, A.; Negro, C.; Antunes, E. Chemical Engineering and Processing: Process Intensification 2008, 8, 1323-1332
30. Lindquist, G. M.; Stratton, R. A. J. Colloid Interface Sci. 1976, 1, 45-59.
31. Alince, B.; Bednar, F.; van de Ven, T. G. M. Colloids Surf. Physicochem. Eng. Aspects 2001, 1-2, 71-80.
32. Ersoy, B. Int. J. Miner. Process. 2005, 3-4, 207-216.
33. Dixon, J. K.; fLa Mer, V. K.; Li, C.; Messinger, S.; Linford, H. B. J. Colloid Interface Sci. 1967, 4, 465-473.
34. Franks, G. V.; Sepulveda, C. V.; Jameson, G. J. AIChE J. 2006, 8, 2774-2782.
35. Li, T.; Zhu, Z.; Wang, D.; Yao, C.; Tang, H. Int. J. Miner. Process. 2007, 1, 23-29.
36. Vanerek, A.; van de Ven, T. G. M. Colloids Surf. Physicochem. Eng. Aspects 2006, 1-3, 55-62.
37. Nasser, M. S.; James, A. E. Separation and Purification Technology 2006, 2, 241-252.
38. Mittal, A.; Scott, G. M.; Amidon, T. E.; Kiemle, D. J.; Stipanovic, A. J. Bioresour. Technol. 2009, 24, 6398-6406.
39. Alves, E. F.; Bose, S. K.; Francis, R. C.; Colodette, J. L.; Iakovlev, M.; Van Heiningen, A. Carbohydr. Polym. 2010, 4, 1097-1101.
40. Duarte, G. V.; Ramarao, B. V.; Amidon, T. E.; Ferreira, P. T. Ind. Eng. Chem. Res. 2011, 50, 17, 9949-9959.
41. Duan, J.; Gregory, J. Adv. Coll. Int. Sci. 2003, 100-102, 475-502.
42. Adachi, Y. Adv. Coll. Int. Sci. 1995, 56, 1-31.
43. Gregory, J.; Barany, S. Adv. Coll. Int. Sci. 2011, 169, 1-12.
44. Nasser, M.; James, A. E. Sep. Pur. Tech. 2006, 52, 241-252.
45. Yu, J.; Wang, D; Ge, X; Yan, M; Yang, M. Coll. Surf. A Physicochem. Asp. 2006, 290, 288-294.
46. Runkana, V.; Somasundaran, P.; Kapur, P. C. J. Coll. Interf. Sci. 2004, 270, 347-358.
47. Amidon, T. E. & Liu, S. 2009, "Water-based woody biorefinery", Biotechnology Advances, vol. 27, no. 5, pp. 542-550.
48. Burke, D. R., Anderson, J., Gilcrease, P. C. & Menkhaus, T. J. 2011, "Enhanced solid-liquid clarification of lignocellulosic slurries using polyelectrolyte flocculating agents", Biomass and Bioenergy, vol. 35, no. 1, pp. 391-401.
49. Duarte, G. V., Ramarao, B. V. & Amidon, T. E. 2010, "Polymer induced flocculation and separation of particulates from extracts of lignocellulosic materials", Bioresource technology, vol. 101, no. 22, pp. 8526-8534.
50. Gaudreault, R., van de Ven, T. G. M. & Whitehead, M. A. 2005, "Mechanisms of flocculation with poly(ethylene oxide) and novel cofactors", Colloids and Surfaces A: Physicochemical and Engineering Aspects, vol. 268, no. 1-3, pp. 131-146.
51. Liu, Z., Fatehi, P., Jahan, M. S. & Ni, Y. 2011, "Separation of lignocellulosic materials by combined processes of pre-hydrolysis and ethanol extraction", Bioresource technology, vol. 102, no. 2, pp. 1264-1269.
52. Mittal, A., Scott, G. M., Amidon, T. E., Kiemle, D. J. & Stipanovic, A. J. 2009, "Quantitative analysis of sugars in wood hydrolyzates with 1H NMR during the autohydrolysis of hardwoods", Bioresource technology, vol. 100, no. 24, pp. 6398-6406.
53. Mpofu, P., Addai-Mensah, J. & Ralston, J. 2004, "Temperature influence of nonionic polyethylene oxide and anionic polyacrylamide on flocculation and dewatering behavior of kaolinite dispersions", Journal of colloid and interface science, vol. 271, no. 1, pp. 145-156.
54. Negro, C., Fuente, E., Blanco, A. & Tijero, J. 2005, "Flocculation mechanism induced by phenolic resin/PEO and floc properties", AICHE Journal, vol. 51, no. 3, pp. 1022-1031.
55. Negro, C., Fuente, E., Sánchez, L. M., Blanco, Á. & Tijero, J. 2006, "Evaluation of an alternative flocculation system for manufacture of fiber-cement composites", Industrial and Engineering Chemistry Research, vol. 45, no. 20, pp. 6672-6678.
56. Xiao, H., Pelton, R. & Hamielec, A. 1995, "The association of aqueous phenolic resin with polyethylene oxide and poly(acrylamide-co-ethylene glycol)", Journal of Polymer Science Part A: Polymer Chemistry, vol 33, 2605-2612
57. Kusch S., Morar M. V., 2009. Integration of lignocellulosic biomass into renewable energy generation concepts. ProEnvironment 2 (2009) 32-37.
58. Tunc, M. S., van Heiningen, A. R. P., 2008. Hemicellulose Extraction of Mixed Southern Hardwood with Water at 150° C.: Effect of Time., Ind. Eng. Chem. Res., 47, 7031-7037.
59. Jonsson A. S, Wallberg O. 2007 Cost estimation of kraft lignin recovery by ultrafiltration. Desalination 237 (2009) 254-267.
60. Grzenia L D, Schell D. J., Wickramasinghe S. R. 2009. Detoxification of biomass hydrolystes by reactive membranes. J. Mem Sci. 348, (2010), 6-12.
61. Grzenia L D, Wickramasinghe S. R. 2007. Adsorptive membranes and resins for acetic acid removal from biomass hydrolyzates, Desalination, 234, (2008), 144-151.
62. Huang, H. J., Ramaswamy, S., Tschirner, U. W., Ramarao, B. V. A review of separation technologies in current and future biorefineries. Sep. Pur. Tech. 62 (2008) 1-21.
63. Negro, C., Fuente, E., Sánchez, L. M., Blanco, Á. & Tijero, J. 2006, "Evaluation of an alternative flocculation system for manufacture of fiber-cement composites", Industrial and Engineering Chemistry Research, vol. 45, no. 20, pp. 6672-6678.
64. Biorefining Process, "Fermentation of Lignocellulosic Biomass", Wisconsin Biorefining Development Initiative, www.biorefine.org/proc/fermlig.pdf

What is claimed is:

1. A method of separating a lignin-rich solid phase from an aqueous suspension comprising a lignocellulosic biomass having an acidic pH and aromatic components, the method comprising:

dividing the aqueous suspension comprising the lignocellulosic biomass having the acidic pH and the aromatic components into a residual lignocellulosic biomass and a suspension comprising soluble components having colloidal material and primarily lignin containing particles, said suspension having a pH less than about 4, using a pretreatment fluid;

flocculating said suspension using a sufficient amount of polyethylene oxide (PEO) as a flocculating agent, substantially without added cofactors;

adding to said suspension a precipitated calcium carbonate to raise the pH to between about 5 to 7.5; and separating the flocculated suspension to remove agglomerates to achieve a reduction in turbidity of about 99.5%.

2. The method according to claim 1, wherein said dividing comprises at least one method selected from the group consisting of sedimentation, centrifugation, and microfiltration.

3. The method according to claim 1, wherein said pretreatment fluid comprises a hot water extraction fluid.

4. The method according to claim 1, wherein said flocculating is conducted at a temperature of about 21.5° C. to about 25° C.

5. The method according to claim 1, further comprising fermenting a solution resulting after separating the flocculated suspension to remove agglomerates.

6. The method according to claim 1, wherein said separating comprises filtering through a filter having a pore size of less than about 10 microns.

7. The method according to claim 1, wherein said separating comprises filtering through at least one of a ceramic filter and a cloth filter.

8. The method according to claim 1, wherein the flocculating is performed for a sufficient time of less than about 2 hours to form agglomerates separable from the flocculated suspension to achieve the reduction in turbidity of about 99.5%.

9. The method according to claim 1, wherein the precipitated calcium carbonate is limited to an amount that does not substantially increase turbidity of the suspension.

10. A method for treating lignocellulosic biomass comprising:
    treating the lignocellulosic biomass with an extractant to extract a suspension comprising soluble components having colloidal material and primarily lignin containing particles from the lignocellulosic biomass, yielding a residual biomass and the suspension having a pH less than about 4;
    separating the suspension from the residual biomass;
    adding a flocculating agent to the suspension to form a flocculated suspension, wherein the flocculating agent comprises polyethylene oxide (PEO) in an amount sufficient to achieve a 99.5% reduction in turbidity after separation;
    adding to the suspension a precipitated calcium carbonate to raise the pH between about 5 and 7.5; and
    separating a flocculated portion of the flocculated suspension from a non-flocculated portion of the flocculated suspension to produce a fermentable solution from the lignocellulosic biomass.

11. The method according to claim 10, wherein the extractant comprises hot water.

12. The method according to claim 10, wherein the suspension is separated from the residual biomass with a separation device which comprises at least one of a filter, a sedimentation tank, and a centrifuge.

13. A method of separating a lignin-rich solid phase from a suspension comprising:
    dividing a lignocellulosic biomass into a residual lignocellulosic biomass and a suspension comprising soluble components having colloidal material and primarily lignin containing particles, the suspension having a pH less than about 4, using a pretreatment fluid;
    treating the suspension with a polymer flocculating agent comprising a sufficient amount of polyethylene oxide (PEO) and precipitated calcium carbonate to raise the pH to between about 5 and 7.5 and said polymer flocculating agent, being substantially without additional cofactors; and
    separating the flocculated suspension to remove agglomerates to achieve a reduction in turbidity of about 99.5%.

14. The method according to claim 13, wherein said dividing comprises at least one method selected from the group consisting of sedimentation, centrifugation, and microfiltration.

15. The method according to claim 13, wherein said suspension comprises an aqueous suspension.

16. The method according to claim 13, wherein said treating is conducted at a temperature of about 21.5° C. to about 25° C.

17. The method according to claim 13, further comprising microbially processing a non-agglomerated portion of the flocculated suspension.

18. The method according to claim 17, wherein said microbially processing comprises fermenting.

19. The method according to claim 13, wherein said separating comprises filtering through a filter having a pore size of less than about 10 microns.

20. The method according to claim 13, wherein said separating comprises filtering through at least one of a ceramic filter and a cloth filter.

21. The method according to claim 13, wherein the treating is performed for less than about 2 hours.

22. The method according to claim 13, wherein said pretreatment fluid comprises a hot water extraction fluid and said treating is conducted at a temperature of about 21.5° C. to about 25° C.

23. The method according to claim 13, wherein the precipitated calcium carbonate is limited to an amount that does not substantially increase turbidity of the suspension.

* * * * *